(12) United States Patent
Betley et al.

(10) Patent No.: US 11,918,984 B2
(45) Date of Patent: Mar. 5, 2024

(54) ANNULATION CATALYSTS VIA DIRECT C—H BOND AMINATION

(71) Applicant: President and Fellows of Harvard College, Cambridge, MA (US)

(72) Inventors: Theodore Alexander Betley, Cambridge, MA (US); Alexandre Mikhailine, Cambridge, MA (US); Claudia Kleinlein, Cambridge, MA (US); Yuyang Dong, Cambridge, MA (US); Yunjung Baek, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 266 days.

(21) Appl. No.: 17/276,855

(22) PCT Filed: Sep. 19, 2019

(86) PCT No.: PCT/US2019/051915
§ 371 (c)(1),
(2) Date: Mar. 17, 2021

(87) PCT Pub. No.: WO2020/061300
PCT Pub. Date: Mar. 26, 2020

(65) Prior Publication Data
US 2022/0016613 A1    Jan. 20, 2022

Related U.S. Application Data

(60) Provisional application No. 62/733,480, filed on Sep. 19, 2018.

(51) Int. Cl.
B01J 31/18    (2006.01)
B01J 31/22    (2006.01)
(Continued)

(52) U.S. Cl.
CPC ....... B01J 31/1815 (2013.01); B01J 31/2243 (2013.01); C07D 207/06 (2013.01);
(Continued)

(58) Field of Classification Search
CPC ............... B01J 31/1815; B01J 31/2243; B01J 2231/4283; B01J 2531/0216;
(Continued)

(56) References Cited

U.S. PATENT DOCUMENTS

2017/0072390 A1    3/2017 Betley et al.

FOREIGN PATENT DOCUMENTS

CN    107987095 A    5/2018

OTHER PUBLICATIONS

Carsch, K.M. et al., 2019, "Supplementary Materials for Synthesis of a copper-supported triplet nitrene complex pertinent to copper-catalyzed amination," in Science, 365, 6458, 145 pp. <10.1126/science.aax4423> (Year: 2019).*
(Continued)

*Primary Examiner* — Brian A McCaig
(74) *Attorney, Agent, or Firm* — Wolf, Greenfield & Sacks, P.C.

(57) ABSTRACT

Disclosed are compounds, methods, reagents, systems, and kits for the preparation and utilization of monomeric or polymeric metal-based compounds. These metal-based compounds are organometallic catalysts composed of substituted dipyrrin ligands bound to transition metals. C—H bond functionalization catalysis can be performed with the disclosed organometallic catalysts to yield C—N bonds to generate substituted bicyclic, spiro, and fused nitrogen-containing heterocycles, all common motifs in various pharmaceutical and bioactive molecules.

20 Claims, 14 Drawing Sheets

(51) Int. Cl.

| | |
|---|---|
| C07D 207/06 | (2006.01) |
| C07D 209/04 | (2006.01) |
| C07D 209/44 | (2006.01) |
| C07D 209/54 | (2006.01) |
| C07D 211/70 | (2006.01) |
| C07D 263/04 | (2006.01) |
| C07D 401/04 | (2006.01) |
| C07D 403/04 | (2006.01) |
| C07D 471/04 | (2006.01) |
| C07D 471/08 | (2006.01) |
| C07D 487/08 | (2006.01) |

(52) U.S. Cl.
CPC ......... *C07D 209/04* (2013.01); *C07D 209/44* (2013.01); *C07D 209/54* (2013.01); *C07D 211/70* (2013.01); *C07D 263/04* (2013.01); *C07D 401/04* (2013.01); *C07D 403/04* (2013.01); *C07D 471/04* (2013.01); *C07D 471/08* (2013.01); *C07D 487/08* (2013.01); *B01J 2231/4283* (2013.01); *B01J 2531/0216* (2013.01); *B01J 2531/842* (2013.01); *B01J 2531/845* (2013.01); *B01J 2531/847* (2013.01); *B01J 2540/66* (2013.01)

(58) Field of Classification Search
CPC ............ B01J 2531/842; B01J 2531/845; B01J 2531/847; B01J 2540/66; C07B 43/04; C07D 207/06; C07D 207/08; C07D 207/44; C07D 209/04; C07D 209/44; C07D 209/54; C07D 211/70; C07D 263/04; C07D 401/04; C07D 403/04; C07D 471/04; C07D 471/08; C07F 15/025; C07F 15/06; C07F 15/065; C07F 17/00; C07J 41/0055
See application file for complete search history.

(56) References Cited

OTHER PUBLICATIONS

Baek, J. et al., 2019, J. Am. Chem. Soc., 141, 7797-7806. <10.1021.jacs.9b01262> (Year: 2019).*
Chisholm, M.H. et al., 2012, : Chem. Sci., 2012, 3, 3445-3457. <10.1039/c2sc21017g> (Year: 2012).*
Aguila et al., Mechanistic insights into C—H amination via dicopper nitrenes. J Am Chem Soc. Jun. 26, 2013;135(25):9399-406. doi: 10.1021/ja400879m. Epub Jun. 13, 2013.
Groves, High-valent iron-porphyrin complexes related to peroxidase and cytochrome P-450. J Am Chem Soc. 1981; 103(10): 2884-86.
Liu et al., Oxidative aliphatic C—H fluorination with fluoride ion catalyzed by a manganese porphyrin. Science. Sep. 14, 2012;337(6100):1322-5. doi: 10.1126/science.1222327.
Lyaskovskyy et al., Mechanism of cobalt(II) porphyrin-catalyzed C—H amination with organic azides: radical nature and H-atom abstraction ability of the key cobalt(III)-nitrene intermediates. J Am Chem Soc. Aug. 10, 2011;133(31):12264-73. doi: 10.1021/ja204800a. Epub Jul. 18, 2011.
Varela-Alvarez et al., Rh2(II,III) Catalysts with Chelating Carboxylate and Carboxamidate Supports: Electronic Structure and Nitrene Transfer Reactivity. J Am Chem Soc. Feb. 24, 2016;138(7):2327-41. doi: 10.1021/jacs.5b12790. Epub Feb. 15, 2016.
Invitation to Pay Additional Fees for Application No. PCT/US2019/051915, mailed Nov. 6, 2019.
International Search Report and Written Opinion for Application No. PCT/US2019/051915, dated Jan. 24, 2020.
International Preliminary Report on Patentability for Application No. PCT/US2019/051915, dated Apr. 1, 2021.
Bagh et al., Catalytic Synthesis of N-Heterocycles via Direct C(sp3)-H Amination Using an Air-Stable Iron(III) Species with a Redox-Active Ligand. J Am Chem Soc. Apr. 12, 2017;139(14):5117-5124. doi: 10.1021/jacs.7b00270. Epub Mar. 28, 2017.
Carruthers, Some Modern Methods of Organic Synthesis. 4th Edition. 2004. Cambridge University Press, Eds.
Chen et al., A predictably selective aliphatic C—H oxidation reaction for complex molecule synthesis. Science. Nov. 2, 2007;318(5851):783-7. doi: 10.1126/science.1148597.
Chen et al., Combined effects on selectivity in Fe-catalyzed methylene oxidation. Science. Jan. 29, 2010;327(5965):566-71. doi: 10.1126/science.1183602.
Davies et al., Catalytic C—H functionalization by metal carbenoid and nitrenoid insertion Nature. Jan. 24, 2008;451(7177):417-24. doi: 10.1038/nature06485.
Davies et al., Recent Advances in C—H Functionalization. J Org Chem. Jan. 15, 2016;81(2):343-50. doi: 10.1021/acs.joc.5b02818.
Dixneuf et al., C—H Bond Activation and Catalytic Functionalization I. 2016. First Edition. vol. 55. Springer International Publishing, Eds. 269 pages.
Dryzhakov et al., Nitro-Assisted Brønsted Acid Catalysis: Application to a Challenging Catalytic Azidation. J Am Chem Soc. Aug. 5, 2015;137(30):9555-8. doi: 10.1021/jacs.5b06055. Epub Jul. 27, 2015.
Galonic et al., Two interconverting Fe(IV) intermediates in aliphatic chlorination by the halogenase CytC3. Nat Chem Biol. Feb. 2007;3(2):113-6. doi: 10.1038/nchembio856. Epub Jan. 14, 2007.
Gephart III et al., Reaction of Cu(I) with dialkyl peroxides: Cu(II)-alkoxides, alkoxy radicals, and catalytic C—H etherification. J Am Chem Soc. Oct. 24, 2012;134(42):17350-3. doi: 10.1021/ja3053688. Epub Oct. 16, 2012.
Goldberg et al., Chemical genetic screen identifies lithocholic acid as an anti-aging compound that extends yeast chronological life span in a TOR-independent manner, by modulating housekeeping longevity assurance processes. Aging (Albany NY). Jul. 2010;2(7):393-414. doi: 10.18632/aging.100168.
Groves, High-valent iron in chemical and biological oxidations. J Inorg Biochem. Apr. 2006;100(4):434-47. doi: 10.1016/j.jinorgbio.2006.01.012. Epub Mar. 3, 2006.
Grynkiewiscz et al., Tropane alkaloids as medicinally useful natural products and their synthetic derivatives as new drugs Pharmacol Rep. Jul.-Aug. 2008;60(4):439-63.
Hartwig et al., Undirected, Homogeneous C—H Bond Functionalization: Challenges and Opportunities. ACS Cent Sci. May 25, 2016;2(5):281-92. doi: 10.1021/acscentsci.6b00032. Epub May 2, 2016.
Hartwig, Evolution of C—H Bond Functionalization from Methane to Methodology. J Am Chem Soc. Jan. 13, 2016;138(1):2-24. doi: 10.1021/jacs.5b08707. Epub Dec. 15, 2015.
Harvey et al., A diruthenium catalyst for selective, intramolecular allylic C—H amination: reaction development and mechanistic insight gained through experiment and theory. J Am Chem Soc. Nov. 2, 2011;133(43):17207-16. doi: 10.1021/ja203576p. Epub Oct. 7, 2011.
Hennessey et al., Complex N-heterocycle synthesis via iron-catalyzed, direct C—H bond amination. Science. May 3, 2013;340(6132):591-5. doi: 10.1126/science.1233701.
Iovan et al., Diastereoselective C—H Bond Amination for Disubstituted Pyrrolidines. Angew Chem Int Ed Engl. Dec. 4, 2017;56(49):15599-15602. doi: 10.1002/anie.201708519. Epub Nov. 8, 2017.
Iovan et al., Characterization of Iron-Imido Species Relevant for N-Group Transfer Chemistry. J Am Chem Soc. Feb. 17, 2016;138(6):1983-93. doi: 10.1021/jacs.5b12582. Epub Feb. 4, 2016.
King et al., Review of the Defensive Chemistry of Coccinellids. Chem Rev. May 9, 1996;96(3):1105-1122. doi: 10.1021/cr950242v.
King et al., Co(III) imidos exhibiting spin crossover and C—H bond activation. J Am Chem Soc. Oct. 31, 2012;134(43):17858-61. doi: 10.1021/ja307699u. Epub Oct. 18, 2012.
King et al., Co(III) imidos exhibiting spin crossover and C—H bond activation. Supplemental Information. Harvard University. 2012. pp. SI-1 to SI-24.
Kleinlein et al., Ground State and Excited State Tuning in Ferric Dipyrrin Complexes Promoted by Ancillary Ligand Exchange.

(56) References Cited

OTHER PUBLICATIONS

Inorg Chem. May 15, 2017;56(10):5892-5901. doi: 10.1021/acs.inorgchem.7b00525. Epub Apr. 24, 2017.

Kong et al., Control of the Chemoselectivity of Metal N-Aryl Nitrene Reactivity: C—H Bond Amination versus Electrocyclization. J Am Chem Soc. Oct. 12, 2016;138(40):13271-13280. doi: 10.1021/jacs.6b07026. Epub Oct. 4, 2016.

Liu et al., Silver-Catalyzed Decarboxylative Radical Azidation of Aliphatic Carboxylic Acids in Aqueous Solution. J Am Chem Soc. Aug. 12, 2015;137(31):9820-3. doi: 10.1021/jacs.5b06821. Epub Jul. 30, 2015.

Mack et al., Ruthenium-Catalyzed C—H Hydroxylation in Aqueous Acid Enables Selective Functionalization of Amine Derivatives. J Am Chem Soc. Jul. 19, 2017;139(28):9503-9506. doi: 10.1021/jacs.7b05469. Epub Jun. 29, 2017.

Matsuoka et al., Functional Supramolecular Architectures of Dipyrrin Complexes. Front Chem. Aug. 15, 2018;6:349. doi: 10.3389/fchem.2018.00349. eCollection 2018.

Moriya, XV.—Contributions from the Laboratory of the University of Tokyo, Japan. No. IV. On menthol or peppermint camphor. J Chem Soc Trans. 1881;39:77-83.

O'Hagan, Pyrrole, pyrrolidine, pyridine, piperidine and tropane alkaloids. Nat Prod Rep. Oct. 2000;17(5):435-46. doi: 10.1039/a707613d.

Read, Recent Progress in the Menthone Chemistry. Chem Rev. 1930;7(1):1-50.

Shang et al., Iron-Catalyzed C—H Bond Activation. Chem Rev. Jul. 12, 2017;117(13):9086-9139. doi: 10.1021/acs.chemrev.6b00772. Epub Apr. 5, 2017.

Sharma et al., Metal-catalysed azidation of tertiary C—H bonds suitable for late-stage functionalization. Nature. Jan. 29, 2015;517(7536):600-4. doi: 10.1038/nature14127.

Wiese et al., Catalytic C—H amination with unactivated amines through copper(II) amides. Angew Chem Int Ed Engl. Nov. 15, 2010;49(47):8850-5. doi: 10.1002/anie.201003676.

Zhang et al., Enantioselective cyanation of benzylic C—H bonds via copper-catalyzed radical relay. Science. Sep. 2, 2016;353(6303):1014-1018. doi: 10.1126/science.aaf7783.

Zhao et al., [((H)L)2Fe6(NCMe)m]n+ (m= 0, 2, 4, 6; n=-1, 0, 1, 2, 3, 4, 6): an electron-transfer series featuring octahedral Fe6 clusters supported by a hexaamide ligand platform. J Am Chem Soc. Jun. 1, 2011;133(21):8293-306. doi: 10.1021/ja2015845. Epub May 11, 2011.

Zhao et al., [((H)L)2Fe6(NCMe)m]n+ (m=0, 2, 4, 6; n=-1, 0, 1, 2, 3, 4, 6): an electron-transfer series featuring octahedral Fe6 clusters supported by a hexaamide ligand platform. Supplemental Information. Harvard University. 2011. pp. S1-S9.

PCT/US2019/051915, Nov. 6, 2019, Invitation to Pay Additional Fees.

PCT/US2019/051915, Jan. 24, 2020, International Search Report and Written Opinion.

PCT/US2019/051915, Apr. 1, 2021, International Preliminary Report on Patentability.

\* cited by examiner (2-IIa, R = H; 2-IIb, R = $^t$Bu; 2-IIc, R = NMe$_2$)

(2-III)

(3-III)

ANNULATION CATALYSTS VIA DIRECT C—H BOND AMINATION

RELATED APPLICATIONS

This application is a national stage filing under 35 U.S.C. § 371 of International PCT Application No. PCT/US2019/051915, filed Sep. 19, 2019, which claims priority under 35 U.S.C. § 119(e) to U.S. Provisional Application No. 62/733,480, filed Sep. 19, 2018, each of which is incorporated herein by reference.

GOVERNMENT SUPPORT

This invention was made with government support under GM-115815 awarded by the National Institutes of Health. The government has certain rights in the invention.

BACKGROUND OF THE INVENTION

Direct carbon-hydrogen (C—H) bond functionalization has become an increasingly more important transformation in designing synthetic strategies (1-5). Carbon-hydrogen bonds comprise the most ubiquitous functional groups found in organic molecules. Thus, methods that convert C—H bonds into new C-heteroatom bearing functionalities are highly desirable. Carbon-heteroatom bond forming reactions are critical in the chemical and pharmaceutical industry to convert readily available substrates into value added commodity chemicals, though the majority of these transformations must be achieved through functional group interconversions. A prominent example is the prevalence of carbon-nitrogen (C—N) bond forming reactions in the pharmaceutical industry, which account for nearly one out of every six reactions performed (6). Chemical transformations that enable direct C—H bond conversion into the more valuable C—N bond, therefore, hold enormous potential to streamline syntheses and reduce chemical waste production.

The difficulty in developing reactions to convert aliphatic C—H bonds into heteroatom functionalities is twofold: the inherent large C—H bond dissociation energy (93-105 kcal/mol) and the spatial inaccessibility of the C—H bonding and antibonding orbitals. Inspired by biological precedent (i.e., cytochrome P450 (7-8), halogenase (9)), chemists have circumvented these barriers by developing radical mediated protocols to separate functionalization into distinct C—H bond-breaking and C-heteroatom bond-making events. A number of exciting developments have recently appeared that utilize this common strategy to effect C—H bond etherification (10), fluorination (11), azidation (12), cyanation (13), hydroxylation (14-16), and amination (16-22) among others. The main challenges associated with these reactions relate to both substrate composition and catalyst performance: substrate chemoselectivity is typically governed by substrate C—H bond strengths; whereas catalyst stability is impacted by product inhibition and functional group tolerance.

An iron-dipyrrin catalyst has been previously reported that cyclized linear, aliphatic azides to furnish N-heterocyclic products (23). Transient formation of an iminyl radical stabilized by the high-spin iron center facilitated nitrene insertion into proximal C—H bonds (24-25). The electron deficient catalyst bound the secondary amine product and precluded catalysis. However, heating the reaction mixture to induce product dissociation in the presence of di-tert-butyl dicarbonate ($Boc_2O$) led to in situ amine protection to give the carboxamide product with concomitant evolution of $CO_2$ and $^tBuOH$. While this permitted catalytic turnover to be realized by preventing product inhibition of the catalyst, turnover numbers were limited (i.e., 5-10) as accumulation of the alcohol byproduct, also a potent Lewis base, resulted in catalyst decomposition. Thus, new catalyst permutations are required to increase thermal stability (giving access to stronger C—H bonds) and compatibility with a greater range of chemical functionalities, in addition to eliminating the requirement for directing or protecting groups to facilitate efficient catalysis.

SUMMARY OF THE INVENTION

Given the critical importance of C—N bond forming reactions in synthesis, general amination strategies utilizing direct C—H bond functionalization can radically change synthetic methodology. The present disclosure is based on, at least in part, the discovery of metal-based compounds that can be used as catalysts to effectively mediate C—H bond amination, furnishing polycyclic N-heterocycle products ideal for late-stage product functionalization. These metal-based compounds permit amination of a full suite of C—H bond types without requiring activating or protecting groups, and some of these metal-based compounds are capable of being recycled to improve overall catalyst performance. Thermally induced catalyst aggregation leads to facile product separation and catalyst recovery, enabling catalyst recycling. Substituted bicyclic, spiro, and fused heterocycles, all common motifs in various pharmaceutical and bioactive molecules, can be constructed using these catalysts.

Compounds, methods, reagents, systems, and kits that allow for the preparation and utilization of metal-based compounds capable of C—H bond amination are disclosed herein.

The metal-based compounds described herein contain organic ligands coordinated to a metal. In certain embodiments, the metal-based compounds are organometallic catalysts. In certain embodiments, the organic ligand is a compound of Formula (I-a):

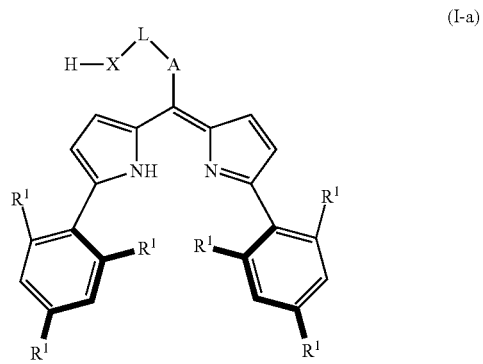

or salt thereof,
wherein:
  each $R^1$ independently is branched or unbranched, substituted or unsubstituted, cyclic or acyclic aliphatic; branched or unbranched, substituted or unsubstituted, cyclic or acyclic heteroaliphatic; substituted or unsubstituted aryl; or substituted or unsubstituted heteroaryl;
  A is substituted or unsubstituted arylene; or substituted or unsubstituted heteroarylene;

L is branched or unbranched, substituted or unsubstituted, cyclic or acyclic aliphatic; or branched or unbranched, substituted or unsubstituted, cyclic or acyclic heteroaliphatic; and X is S, O, or $NR_X$, wherein $R_X$ is hydrogen; nitrogen protecting group; branched or unbranched, substituted or unsubstituted, cyclic or acyclic aliphatic; branched or unbranched, substituted or unsubstituted, cyclic or acyclic heteroaliphatic; substituted or unsubstituted arylene; or substituted or unsubstituted heteroarylene.

The metal-based compounds described herein can be cyclic alternating copolymers composed of metals coordinated to ligands. In certain embodiments, the metal-based compounds are organometallic catalysts. In certain embodiments, the organometallic catalyst is a compound of Formula (I):

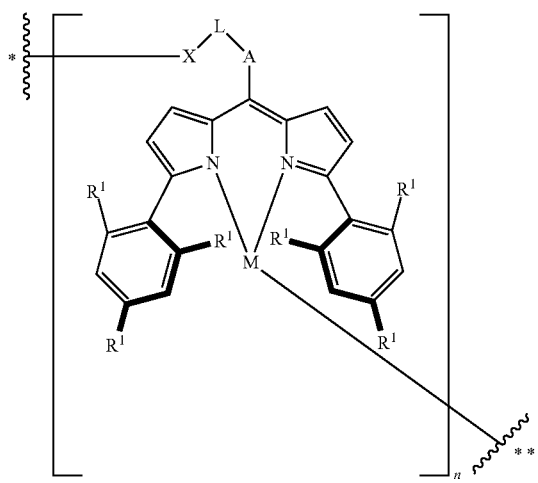

(I)

or a salt thereof,
wherein:
  each $R^1$ independently is branched or unbranched, substituted or unsubstituted, cyclic or acyclic aliphatic; branched or unbranched, substituted or unsubstituted, cyclic or acyclic heteroaliphatic; substituted or unsubstituted aryl; or substituted or unsubstituted heteroaryl;
  A is substituted or unsubstituted arylene; or substituted or unsubstituted heteroarylene;
  L is branched or unbranched, substituted or unsubstituted, cyclic or acyclic aliphatic; or branched or unbranched, substituted or unsubstituted, cyclic or acyclic heteroaliphatic;
  X is S, O, or $NR_X$, wherein $R_X$ is hydrogen; nitrogen protecting group; branched or unbranched, substituted or unsubstituted, cyclic or acyclic aliphatic; branched or unbranched, substituted or unsubstituted, cyclic or acyclic heteroaliphatic; substituted or unsubstituted arylene; or substituted or unsubstituted heteroarylene;
  M is a transition metal; and
  n is an integer between 2 and 10, inclusive;
wherein the atom X labeled "*" of one monomer is bonded to the transition metal M labeled "**" of another monomer.

The metal-based compounds described herein can be monomeric organometallic compounds. In certain embodiments, the organometallic compounds are catalysts. In certain embodiments, the metal-based catalyst is a compound of Formula (II):

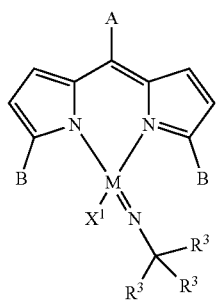

(II)

or a salt thereof,
wherein:
  each $R^3$ independently is hydrogen; branched or unbranched, substituted or unsubstituted, cyclic or acyclic aliphatic; branched or unbranched, substituted or unsubstituted, cyclic or acyclic heteroaliphatic; substituted or unsubstituted aryl; substituted or unsubstituted heteroaryl; $—SR_X$ or $—OR_X$, wherein $R_X$ is hydrogen; oxygen protecting group; sulfur protecting group; branched or unbranched, substituted or unsubstituted, cyclic or acyclic aliphatic; branched or unbranched, substituted or unsubstituted, cyclic or acyclic heteroaliphatic; substituted or unsubstituted aryl; or substituted or unsubstituted heteroaryl; or $—N(R_X)_2$, wherein each $R_X$ independently is hydrogen; nitrogen protecting group; branched or unbranched, substituted or unsubstituted, cyclic or acyclic aliphatic; branched or unbranched, substituted or unsubstituted, cyclic or acyclic heteroaliphatic; substituted or unsubstituted aryl; or substituted or unsubstituted heteroaryl;
  A is substituted or unsubstituted aryl; or substituted or unsubstituted heteroaryl;
  each B independently is branched or unbranched, substituted or unsubstituted, cyclic or acyclic aliphatic; branched or unbranched, substituted or unsubstituted, cyclic or acyclic heteroaliphatic; substituted or unsubstituted aryl; or substituted or unsubstituted heteroaryl;
  $X^1$ is a substituted or unsubstituted, cyclic or acyclic heteroaliphatic; or substituted or unsubstituted heteroarylene; and
  M is a transition metal.

In certain embodiments, the metal-based catalyst is a compound of Formula (III):

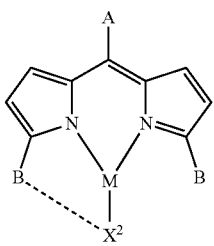

(III)

or a salt thereof,
wherein:
  A is substituted or unsubstituted aryl; or substituted or unsubstituted heteroaryl;
  each B independently is branched or unbranched, substituted or unsubstituted, cyclic or acyclic aliphatic;

branched or unbranched, substituted or unsubstituted, cyclic or acyclic heteroaliphatic; substituted or unsubstituted aryl; or substituted or unsubstituted heteroaryl;

$X^2$ is branched or unbranched, substituted or unsubstituted, cyclic or acyclic heteroaliphatic; substituted or unsubstituted aryl; or substituted or unsubstituted heteroaryl;

--- is a bond or absent; and

M is a transition metal.

In one aspect, the present disclosure provides methods of performing C—H bond amination to prepare compounds of Formula (IV):

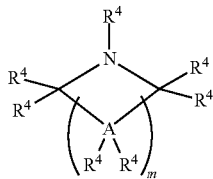

(IV)

or salt thereof, comprising:
  reacting an azide of Formula (IV-a) with a compound of Formula (I), Formula (II), or Formula (III) to produce a cyclic amine of Formula (IV);
wherein:
an azide of Formula (IV-a) is of formula

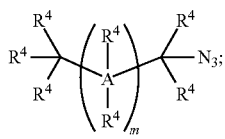

(IV-a)

each $R^4$ independently is hydrogen; branched or unbranched, substituted or unsubstituted, cyclic or acyclic aliphatic; branched or unbranched, substituted or unsubstituted, cyclic or acyclic heteroaliphatic; substituted or unsubstituted aryl; substituted or unsubstituted heteroaryl; two $R^4$ bonded to the same atom are taken together to form an oxo group or a cyclic aliphatic or cyclic heteroaliphatic moiety; two $R^4$ bonded to different atoms are taken together to form a cyclic aliphatic, cyclic heteroaliphatic, arylene, or heteroarylene moiety; two $R^4$ bonded to two adjacent atoms are replaced with a π bond between the two adjacent atoms; or absent;

m is an integer between 2 and 8, inclusive;

each A independently is C, S, O, or N.

In another aspect, the present disclosure provides methods of preparing a compound of Formula (I), or salt thereof, comprising:
  reacting a compound of Formula (I-a) with an organometallic iron compound to produce a compound of Formula (I).

In yet another aspect, the present disclosure provides kits for the preparation of a compound of Formula (I). In certain embodiments, the kits are comprised of: a) a compound of Formula (I-a) within a first container; b) an organometallic compound within a second container; c) optionally, one more solvents; and d) optionally, instructions for use.

In yet another aspect, the present disclosure provides kits for the preparation of a compound of Formula (IV). In certain embodiments, the kits are comprised of:
  a) a compound of a compound of Formula (I), Formula (II), or Formula (III) in a first container;
  b) an azide of Formula (IV-a) in a second container,

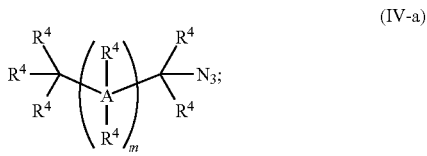

(IV-a)

each $R^4$ independently is hydrogen; branched or unbranched, substituted or unsubstituted, cyclic or acyclic aliphatic; branched or unbranched, substituted or unsubstituted, cyclic or acyclic heteroaliphatic; substituted or unsubstituted aryl; substituted or unsubstituted heteroaryl; two $R^4$ bonded to the same atom are taken together to form an oxo group or a cyclic aliphatic or cyclic heteroaliphatic moiety; two $R^4$ bonded to different atoms are taken together to form a cyclic aliphatic, cyclic heteroaliphatic, arylene, or heteroarylene moiety; two $R^4$ bonded to two adjacent atoms are replaced with a π bond between the two atom; or absent; m is an integer between 2 and 8, inclusive; each A independently is C, S, O, or N;
  c) optionally, one more solvents; and
  d) optionally, instructions for use.

The details of certain embodiments of the invention are set forth in the Detailed Description of Certain Embodiments, as described below. Other features, objects, and advantages of the invention will be apparent from the Definitions, Figures, Examples, and Claims.

DEFINITIONS

Figure 1:
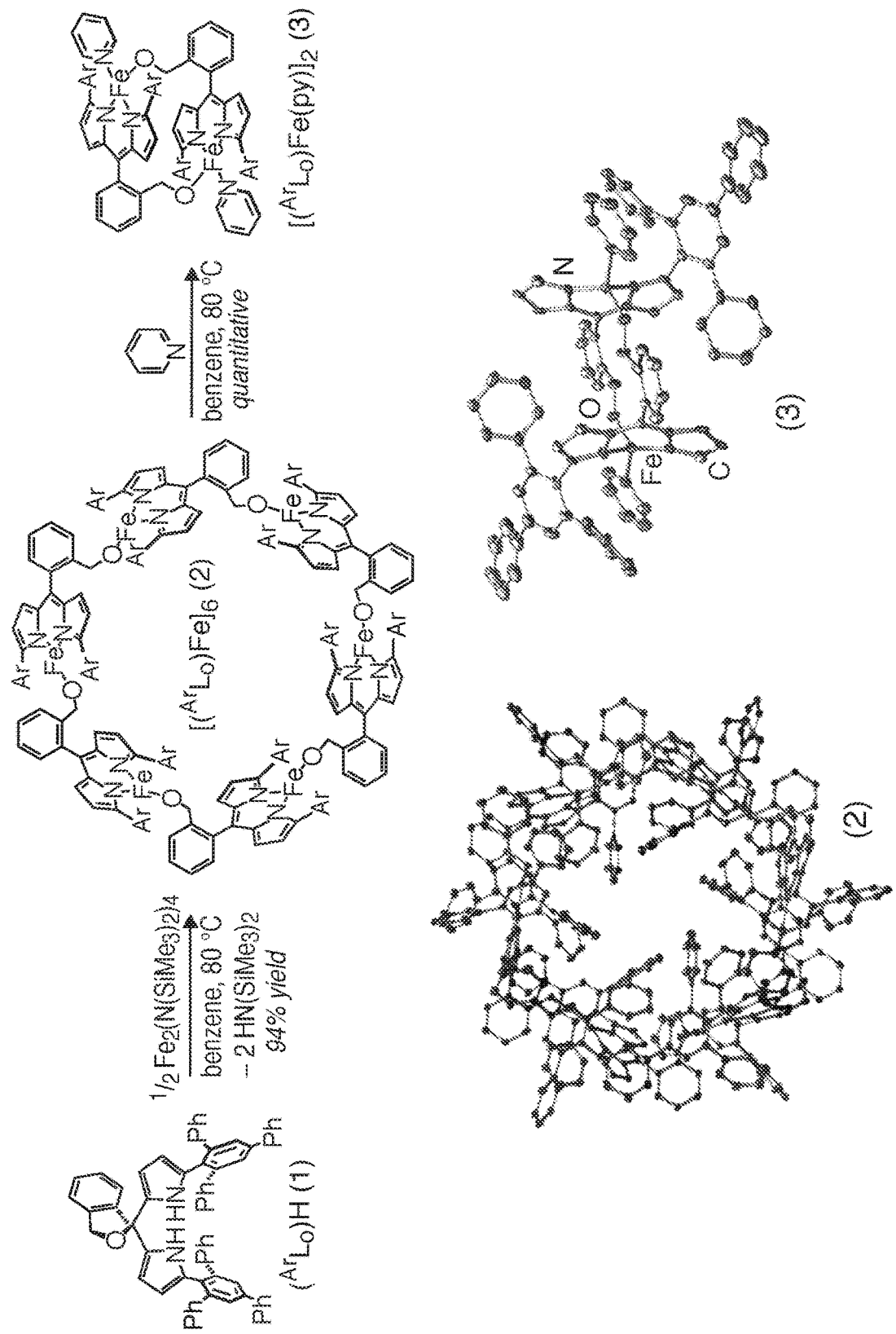
FIG. 1 shows the synthesis of hexameric ferrous wheel precatalyst $[(^{Ar}L_O)Fe]_6$ (2) from dipyrrin alkoxide $(^{Ar}L_O)H$ (1) and formation of pyridine adduct $[(^{Ar}L_O)Fe(py)]_2$ (3) shown as a truncated structure.
Figure 2:
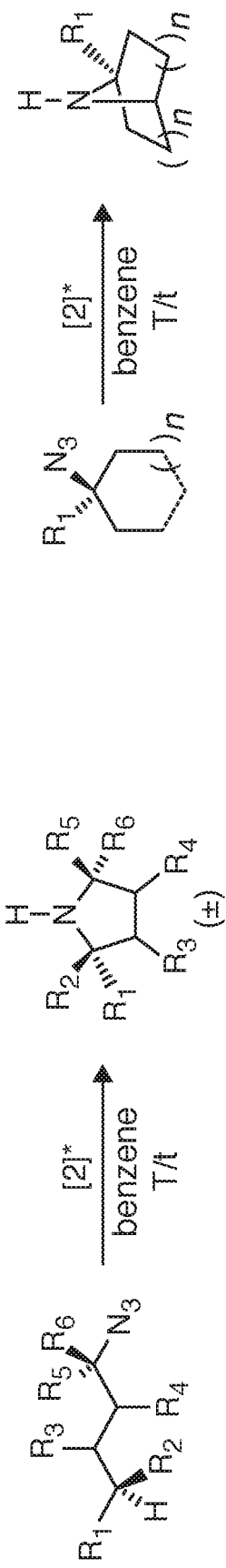
FIG. 2 shows the general annulation reactions to form mono- and polycyclic N-heterocycles.

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987. The disclosure is not intended to be limited in any manner by the exemplary listing of substituents described herein.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, IN 1972). The disclosure additionally encompasses compounds described herein as individual isomers substantially free of other isomers, and alternatively, as mixtures of various isomers.

In a formula, ⁓ is a single bond where the stereochemistry of the moieties immediately attached thereto is not specified, --- is absent or a single bond, and === or $\equiv$ is a single or double bond.

When a range of values is listed, it is intended to encompass each value and sub-range within the range. For example, "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The term "aliphatic" includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, the term "alkyl" includes straight, branched and cyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups. In certain embodiments, "lower alkyl" is used to indicate those alkyl groups (cyclic, acyclic, substituted, unsubstituted, branched or unbranched) having 1-6 carbon atoms.

The term "heteroaliphatic" refers to heteroalkyl, heteroalkenyl, heteroalkynyl, and heterocyclic groups.

In certain embodiments, the alkyl, alkenyl, and alkynyl groups employed in the disclosure contain 1-20 aliphatic carbon atoms. In certain other embodiments, the alkyl, alkenyl, and alkynyl groups employed in the disclosure contain 1-10 aliphatic carbon atoms. In yet other embodiments, the alkyl, alkenyl, and alkynyl groups employed in the disclosure contain 1-8 aliphatic carbon atoms. In still other embodiments, the alkyl, alkenyl, and alkynyl groups employed in the disclosure contain 1-6 aliphatic carbon atoms. In yet other embodiments, the alkyl, alkenyl, and alkynyl groups employed in the disclosure contain 1-4 carbon atoms. Illustrative aliphatic groups thus include, but are not limited to, for example, methyl, ethyl, npropyl, isopropyl, cyclopropyl, —$CH_2$-cyclopropyl, vinyl, allyl, n-butyl, sec-butyl, isobutyl, tertbutyl, cyclobutyl, —$CH_2$-cyclobutyl, n-pentyl, sec-pentyl, isopentyl, tert-pentyl, cyclopentyl, —$CH_2$-cyclopentyl, n-hexyl, sec-hexyl, cyclohexyl, —$CH_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl (C4) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F, or —OH). In certain embodiments, the alkyl group is an unsubstituted $C_{1-10}$ alkyl (such as unsubstituted $C_{1-6}$ alkyl or $C_{1-3}$ alkyl, e.g., —$CH_3$). In certain embodiments, the alkyl group is a substituted $C_{1-10}$ alkyl (such as substituted $C_{1-6}$ alkyl or $C_{1-3}$ alkyl, e.g., —$CF_3$ or $CH_2OH$).

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl. In an alkenyl group, a C=C double bond for which the stereochemistry is not specified (e.g., —CH=$CHCH_3$ or

)

may be an (E)- or (Z)-double bond.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 20 carbon atoms and 1 or more heteroatoms within the parent chain ("hetero$C_{1-20}$ alkyl" or "$C_{1-20}$ heteroalkyl"). In certain embodiments, a heteroalkyl group refers to a saturated group having from 1 to 12 carbon atoms and 1 or more heteroatoms within the parent chain ("hetero$C_{1-12}$ alkyl"). In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and for 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 20 carbon atoms, at least one double bond, and 1 or more heteroatoms within the parent chain ("hetero$C_{2-20}$ alkenyl" or "$C_{2-20}$ heteroalkenyl"). In certain embodiments, a heteroalkenyl group refers to a group having from 2 to 12 carbon atoms, at least one double bond, and 1 or more heteroatoms within the parent chain ("hetero$C_{2-12}$ alkenyl"). In certain embodiments, a heteroalkenyl group refers to a group having from 2 to 10 carbon atoms, at least one double bond, and 1 or more heteroatoms within the parent chain ("hetero$C_{2-10}$ alkenyl"). In some embodiments, a heteroalkenyl group has 2 to 9 carbon atoms at least one double bond, and 1 or more heteroatoms within the parent chain ("hetero$C_{2-9}$ alkenyl"). In some embodiments, a heteroalkenyl group has 2 to 8 carbon atoms, at least one double bond, and 1 or more heteroatoms within the parent chain ("hetero$C_{2-8}$ alkenyl"). In some embodiments, a heteroalkenyl group has 2 to 7 carbon atoms, at least one double bond, and 1 or more heteroatoms within the parent chain ("hetero$C_{2-7}$ alkenyl"). In some embodiments, a heteroalkenyl group has 2 to 6 carbon atoms, at least one double bond, and 1 or more heteroatoms within the parent chain ("hetero$C_{2-6}$ alkenyl"). In some embodiments, a heteroalkenyl group has 2 to 5 carbon atoms, at least one double bond, and 1 or 2 heteroatoms within the parent chain ("hetero$C_{2-5}$ alkenyl"). In some embodiments, a heteroalkenyl group has 2 to 4 carbon atoms, at least one double bond, and for 2 heteroatoms within the parent chain ("hetero$C_{2-4}$ alkenyl"). In some embodiments, a heteroalkenyl group has 2 to 3 carbon atoms, at least one double bond, and 1 heteroatom within the parent chain ("hetero$C_{2-3}$ alkenyl"). In some embodiments, a heteroalkenyl group has 2 to 6 carbon atoms, at least one double bond, and 1 or 2 heteroatoms within the parent chain ("hetero$C_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted hetero$C_{2-10}$ alkenyl. In certain embodiments, the heteroalkenyl group is a substituted hetero$C_{2-10}$ alkenyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 20 carbon atoms, at least one triple bond, and 1 or more heteroatoms within the parent chain ("hetero$C_{2-20}$ alkynyl" or "$C_{2-20}$ heteroalkynyl"). In certain embodiments, a heteroalkynyl group refers to a group having from 2 to 12 carbon atoms, at least one triple bond, and 1 or more heteroatoms within the parent chain ("hetero$C_{2-12}$ alkynyl"). In certain embodiments, a heteroalkynyl group refers to a group having from 2 to 10 carbon atoms, at least one triple bond, and 1 or more heteroatoms within the parent chain ("hetero$C_{2-10}$ alkynyl"). In some embodiments, a heteroalkynyl group has 2 to 9 carbon atoms, at least one triple bond, and 1 or more heteroatoms within the parent chain ("hetero$C_{2-9}$ alkynyl"). In some embodiments, a heteroalkynyl group has 2 to 8 carbon atoms, at least one triple bond, and 1 or more heteroatoms within the parent chain ("hetero$C_{2-8}$ alkynyl"). In some embodiments, a heteroalkynyl group has 2 to 7 carbon atoms, at least one triple bond, and 1 or more heteroatoms within the parent chain ("hetero$C_{2-7}$ alkynyl"). In some embodiments, a heteroalkynyl group has 2 to 6 carbon atoms, at least one triple bond, and 1 or more heteroatoms within the parent chain ("hetero$C_{2-6}$ alkynyl").

In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and for 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

The term "carbocyclyl" or "carbocyclic" refers to a radical of a non-aromatic cyclic hydrocarbon group having from 3 to 14 ring carbon atoms ("C$_{3-14}$ carbocyclyl") and zero heteroatoms in the non-aromatic ring system. In some embodiments, a carbocyclyl group has 3 to 10 ring carbon atoms ("C$_{3-10}$ carbocyclyl"). In some embodiments, a carbocyclyl group has 3 to 8 ring carbon atoms ("C$_{3-8}$ carbocyclyl"). In some embodiments, a carbocyclyl group has 3 to 7 ring carbon atoms ("C$_{3-7}$ carbocyclyl"). In some embodiments, a carbocyclyl group has 3 to 6 ring carbon atoms ("C$_{3-6}$ carbocyclyl"). In some embodiments, a carbocyclyl group has 4 to 6 ring carbon atoms ("C$_{4-6}$ carbocyclyl"). In some embodiments, a carbocyclyl group has 5 to 6 ring carbon atoms ("C$_{5-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include the aforementioned C$_{3-8}$ carbocyclyl groups as well as cyclononyl (C$_9$), cyclononenyl (C$_9$), cyclodecyl (Cm), cyclodecenyl (Cm), octahydro-1H-indenyl (C$_9$), decahydronaphthalenyl (Cm), spiro[4.5]decanyl (Cm), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted C$_{3-14}$ carbocyclyl. In certain embodiments, the carbocyclyl group is a substituted C$_{3-14}$ carbocyclyl.

In some embodiments, "carbocyclyl" is a monocyclic, saturated carbocyclyl group having from 3 to 14 ring carbon atoms ("C$_{3-14}$ cycloalkyl"). In some embodiments, a cycloalkyl group has 3 to 10 ring carbon atoms ("C$_{3-10}$ cycloalkyl"). In some embodiments, a cycloalkyl group has 3 to 8 ring carbon atoms ("C$_{3-8}$ cycloalkyl"). In some embodiments, a cycloalkyl group has 3 to 6 ring carbon atoms ("C$_{3-6}$ cycloalkyl"). In some embodiments, a cycloalkyl group has 4 to 6 ring carbon atoms ("C$_{4-6}$ cycloalkyl"). In some embodiments, a cycloalkyl group has 5 to 6 ring carbon atoms ("C$_{5-6}$ cycloalkyl"). In some embodiments, a cycloalkyl group has 5 to 10 ring carbon atoms ("C$_{5-10}$ cycloalkyl"). Examples of C$_{5-6}$ cycloalkyl groups include cyclopentyl (C$_5$) and cyclohexyl (C$_5$). Examples of C$_{3-6}$ cycloalkyl groups include the aforementioned C$_{5-6}$ cycloalkyl groups as well as cyclopropyl (C$_3$) and cyclobutyl (C$_4$). Examples of C$_{3-8}$ cycloalkyl groups include the aforementioned C$_{3-6}$ cycloalkyl groups as well as cycloheptyl (C$_7$) and cyclooctyl (C$_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted C$_{3-14}$ cycloalkyl. In certain embodiments, the cycloalkyl group is a substituted C$_{3-14}$ cycloalkyl. In certain embodiments, the carbocyclyl includes 0, 1, or 2 C=C double bonds in the carbocyclic ring system, as valency permits.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl. In certain embodiments, the heterocyclyl is substituted or unsubstituted, 3- to 7-membered, monocyclic heterocyclyl, wherein 1, 2, or 3 atoms in the heterocyclic ring system are independently oxygen, nitrogen, or sulfur, as valency permits.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include azirdinyl, oxiranyl, and thiiranyl. Exemplary 4-membered heterocyclyl groups containing 1 heteroatom include azetidinyl, oxetanyl, and thietanyl. Exemplary 5-membered heterocyclyl groups containing 1 heteroatom include tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include dioxolanyl, oxathiolanyl and dithiolanyl. Exemplary 5-membered heterocyclyl groups containing 3 heteroatoms include triazolinyl, oxadiazolinyl, and thiadiazolinyl. Exemplary 6-membered heterocyclyl groups containing 1 heteroatom include piperidinyl, tetrahydropyranyl, dihydropyridinyl, and thianyl. Exemplary 6-membered heterocyclyl groups containing 2 heteroatoms include piperazinyl, morpholinyl, dithianyl, and dioxanyl. Exemplary 6-membered heterocyclyl groups containing 3 heteroatoms include triazinyl. Exemplary 7-membered heterocyclyl groups containing 1 heteroatom include azepanyl, oxepanyl and thiepanyl. Exemplary 8-membered heterocyclyl groups containing 1 heteroatom include azocanyl, oxecanyl and thiocanyl. Exemplary bicyclic heterocyclyl groups include indolinyl, isoindolinyl, dihydrobenzofuranyl, dihydrobenzothienyl, tetra-hydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Heteroaryl" refers to a radical of a 5-14 membered monocyclic or polycyclic 4n+2 aromatic ring system (e.g., having 6, 10, or 14 pi electrons shared in a cyclic array) having ring carbon atoms and 1-4 ring heteroatoms provided in the aromatic ring system, wherein each heteroatom is independently selected from nitrogen, oxygen and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). Polycyclic heteroaryl groups wherein two or three rings independently contain a heteroatom (e.g., furopyrrolyl, thienopyrrolyl, and the like) are also included.

In some embodiments, a heteroaryl group is a 5-14 membered aromatic ring system having ring carbon atoms and 1-4 ring heteroatoms provided in the aromatic ring system, wherein each heteroatom is independently selected from nitrogen, oxygen, and sulfur ("5-14 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridyl. Exemplary 6-membered heteroaryl groups containing two heteroatoms include, without limitation, pyridazinyl, pyrimidyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

An atom, moiety, or group described herein may be unsubstituted or substituted, as valency permits, unless otherwise provided expressly. The term "optionally substituted" refers to substituted or unsubstituted.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. The term "optionally substituted" refers to being substituted or unsubstituted. In certain embodiments, alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety. In certain embodiments, the substituent is a carbon atom substituent. In certain embodiments, the substituent is a nitrogen atom substituent. In certain embodiments, the substituent is an oxygen atom substituent. In certain embodiments, the substituent is a sulfur atom substituent.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups; wherein X$^-$ is a counterion, or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O) R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$) OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N (R$^{ff}$)$_2$, —SO$_2$R$^{ee}$, —SO$_2$OR$^{ee}$, —OSO$_2$R$^{ee}$, —S(=O) R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S; wherein X$^-$ is a counterion;

each instance of $R^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$ X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$ (C$_{1-6}$ alkyl), —NHC(=O)N(C$_{1-6}$ alkyl)$_2$, —NHC (=O)NH(C$_{1-6}$ alkyl), —NHC(=O)NH$_2$, —C(=NH) O(C$_{1-6}$ alkyl), —OC(=NH)(C$_{1-6}$ alkyl), —OC(=NH) OC$_{1-6}$ alkyl, —C(=NH)N(C$_{1-6}$ alkyl)$_2$, —C(=NH) NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH (C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP (=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal $R^{gg}$ substituents can be joined to form =O or =S; wherein X$^-$ is a counterion.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4$$^-$, PF$_4$$^-$, PF$_6$$^-$, AsF$_6$$^-$, SbF$_6$$^-$, B[3,5-(CF$_3$)$_2$C$_6$H$_3$]$_4$]$^-$, BPh$_4$$^-$, Al(OC(CF$_3$)$_3$)$_4$$^-$, and a carborane anion (e.g., CB$_{11}$H$_{12}$$^-$ or (HCB$_{11}$Me$_5$Br$_6$)$^-$). Exemplary counterions which may be multivalent include CO$_3$$^{2-}$, HPO$_4$$^{2-}$, PO$_4$$^{3-}$, B$_4$O$_7$$^{2-}$, SO$_4$$^{2-}$, S$_2$O$_3$$^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

"Halo" or "halogen" refers to fluorine (fluoro, —F), chlorine (chloro, —Cl), bromine (bromo, —Br), or iodine (iodo, —I).

"Acyl" refers to a moiety selected from the group consisting of —C(=O)R$^{aa}$, —CHO, —CO$_2$R$^{aa}$, —C(=O)N (R$^{bb}$)$_2$, —C(=NR$^{bb}$)R$^{aa}$, —C(=NR$^{bb}$)OR$^{aa}$, —C(=NR$^{bb}$) N(R$^{bb}$)$_2$, —C(=O)NR$^{bb}$SO$_2$R$^{aa}$, —C(=S)N(R$^{bb}$)$_2$, —C(=O)SR$^{aa}$, or —C(=S)SR$^{aa}$, wherein R$^{aa}$ and R$^{bb}$ are as defined herein.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N (R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$, and R$^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N (R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)O$R^{aa}$) include, but are not limited to, methyl carbamate, ethylcarbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-climethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$$R^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), (3-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-cliphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

Exemplary oxygen atom substituents include, but are not limited to, —R$^{aa}$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$$^+$X$^-$, —P(OR$^{cc}$)$_2$, —P(OR$^{cc}$)$_3$$^+$X$^-$, —P(=O)(R$^{aa}$)$_2$, —P(=O)(OR$^{cc}$)$_2$, and —P(=O)(N(R$^{bb}$)$_2$)$_2$, wherein X$^-$, R$^{aa}$, R$^{bb}$, and R$_{cc}$ are as defined herein. In certain embodiments, the oxygen atom substituent present on an oxygen atom is an oxygen protecting group (also referred to as a hydroxyl protecting group). Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference. Exemplary oxygen protecting groups include, but are not limited to, methyl, t-butyloxycarbonyl (BOC or Boc), methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris (levulinoyloxyphenyl)methyl, 4,4',4''-tris(benzoyloxyphenyl)methyl, 3-(imidazol-1-yl)bis(4',4''-climethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-naphthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a thiol protecting group). Sulfur protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$) R$^{aa}$, —C(=NR$^{bb}$)OR$^{aa}$, —C(=NR$^{bb}$)N(R$^{bb}$)$_2$, —S(=O) R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

As used herein, the term "salt" refers to any and all salts.

The term "monomer" refers to a molecule that may be covalently joined to other monomers to form a polymer. The process by which the monomers are combined to form a polymer is called polymerization. Molecules made of a small number of monomer units (up to a few dozen) are called oligomers. Monomers can be a small molecule or a large molecule. Monomers can be organic compounds, inorganic compounds, or metals.

The term "polymer" refers to a molecule including two or more (e.g., 3 or more, 4 or more, 5 or more, 10 or more) repeating units which are covalently bound together. In certain embodiments, a polymer comprises 2 or more, 3 or more, 4 or more, 5 or more, 6 or more, 7 or more, 8 or more, 9 or more, or 10 or more repeating units. The repeating units of a polymer are referred to as "monomers." A "homopolymer" is a polymer that consists of a single repeating monomer. A "copolymer" is a polymer that comprises two or more different monomer subunits. Copolymers include, but are not limited to, random, block, alternating, segmented, linear, branched, grafted, and tapered copolymers. Polymers can also be cyclic.

The term "solvent" refers to a substance that dissolves one or more solutes, resulting in a solution. A solvent may serve as a medium for any reaction or transformation described herein. The solvent may dissolve one or more reactants or reagents in a reaction mixture. The solvent may facilitate the mixing of one or more reagents or reactants in a reaction mixture. The solvent may also serve to increase or decrease the rate of a reaction relative to the reaction in a different solvent. Solvents can be polar or non-polar, protic or aprotic. Common solvents useful in the methods described herein include, but are not limited to, acetone, acetonitrile, benzene, benzonitrile, 1-butanol, 2-butanone, butyl acetate, tert-butyl methyl ether, carbon disulfide carbon tetrachloride, chlorobenzene, 1-chlorobutane, chloroform, cyclohexane, cyclopentane, 1,2-dichlorobenzene, 1,2-dichloroethane, dichloromethane (DCM), N,N-dimethylacetamide N,N-dimethylformamide (DMF), 1,3-dimethyl-3,4,5,6-tetrahydro-2-pyrimidinone (DMPU), 1,4-dioxane, 1,3-dioxane, diethylether, 2-ethoxyethyl ether, ethyl acetate, ethyl alcohol, ethylene glycol, dimethyl ether, heptane, n-hexane, hexanes, hexamethylphosphoramide (HMPA), 2-methoxyethanol, 2-methoxyethyl acetate, methyl alcohol, 2-methylbutane, 4-methyl-2-pentanone, 2-methyl-1-propanol, 2-methyl-2-propanol, 1-methyl-2-pyrrolidinone, dimethylsulfoxide (DMSO), nitromethane, 1-octanol, pentane, 3-pentanone, 1-propanol, 2-propanol, pyridine, tetrachloroethylene, tetrahyrdofuran (THF), 2-methyltetrahydrofuran, toluene, trichlorobenzene, 1,1,2-trichlorotrifluoroethane, 2,2,4-trimethylpentane, trimethylamine, triethylamine, N,N-diisopropylethylamine, diisopropylamine, water, o-xylene, and p-xylene.

The term "small molecule" refers to molecules, whether naturally-occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is not more than about 1,000 g/mol, not more than about 900 g/mol, not more than about 800 g/mol, not more than about 700 g/mol, not more than about 600 g/mol, not more than about 500 g/mol, not more than about 400 g/mol, not more than about 300 g/mol, not more than about 200 g/mol, or not more than about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 200 g/mol and not more than about 500 g/mol) are also possible.

A "large organic molecule" or "large molecule" refers to an organic compound that is not a small molecule. In certain embodiments, the molecular weight of a large molecule is greater than about 2,000 g/mol, greater than about 3,000 g/mol, greater than about 4,000 g/mol, or greater than about 5,000 g/mol. In certain embodiments, the molecular weight of a large molecule is at most about 100,000 g/mol, at most about 30,000 g/mol, at most about 10,000 g/mol, at most about 5,000 g/mol, or at most about 2,000 g/mol. Combinations of the above ranges (e.g., greater than about 2,000 g/mol and at most about 10,000 g/mol) are also possible.

The term "haptic bonding" or "hapticity" refers to the coordination of a ligand to a metal center via an uninterrupted and contiguous series of atoms. The hapticity of a ligand is described with the Greek letter η ('eta'). $η^2$ describes a ligand that coordinates through 2 contiguous atoms. $η^3$ describes a ligand that coordinates through 3 contiguous atoms. $η^4$ describes a ligand that coordinates through 4 contiguous atoms. $η^5$ describes a ligand that coordinates through 5 contiguous atoms. $η^6$ describes a ligand that coordinates through 6 contiguous atoms. In general, the η-notation only applies when multiple atoms are coordinated.

The details of one or more embodiments of the disclosure are set forth herein. Other features, objects, and advantages of the disclosure will be apparent from the Detailed Description, the Examples, and the Claims.

DETAILED DESCRIPTION OF CERTAIN EMBODIMENTS

Before the disclosed systems, compositions, methods, reagents, and kits are described in more detail, it should be understood that the aspects described herein are not limited to specific embodiments, methods, apparati, or configurations, and as such can, of course, vary. It is also to be understood that the terminology used herein is for the purpose of describing particular aspects only and, unless specifically defined herein, is not intended to be limiting.

Described herein are synthetic methods for metal-based compounds containing organic ligands. The metals are transition metals and the organic ligands are small molecules coordinated to the transition metals. In certain embodiments, the metal-based compound is a catalyst. In certain embodiments, the catalyst is a iron-based catalyst, cobalt-based catalyst, or nickel-based catalyst. The catalyst can perform annulation reactions via direct C—H bond functionalization. The key amination reactivity does not require activating groups for the targeted C—H bond functionalities, as the full suite of aliphatic C—H bonds reacts cleanly in the protocol established (primary, secondary, tertiary, benzylic, allylic); nor does the catalyst necessitate protecting group strategies to sequester the product to prevent catalyst poisoning. In certain embodiments, the catalyst is thermally robust and undergoes reversible aggregation allowing for facile product isolation, catalyst recovery and recycling, capturing attractive features of both homogeneous and heterogeneous catalysis. In addition, the C—H bond amination described in this disclosure allows for the generation of polycyclic N-heterocycle products ideal for late-stage product functionalization.

Monomeric Organometallic Compounds

Compounds in this disclosure include monomeric organometallic compounds, which contain at least one organic compound as a ligand coordinated to one or more metal atoms.

The present disclosure encompasses compounds of Formula (II):

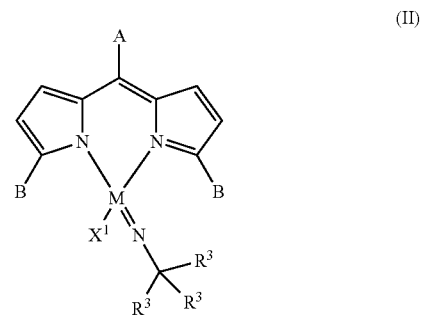

or a salt thereof,
wherein:
each $R^3$ independently is hydrogen; branched or unbranched, substituted or unsubstituted, cyclic or acyclic aliphatic; branched or unbranched, substituted or unsubstituted, cyclic or acyclic heteroaliphatic; substituted or unsubstituted aryl; substituted or unsubstituted heteroaryl; —SR$_X$ or —OR$_X$, wherein R$_X$ is hydrogen; oxygen protecting group; sulfur protecting group; branched or unbranched, substituted or unsubstituted, cyclic or acyclic aliphatic; branched or unbranched, substituted or unsubstituted, cyclic or acyclic heteroaliphatic; substituted or unsubstituted aryl; or substituted or unsubstituted heteroaryl; or —N(R$_X$)$_2$, wherein each R$_X$ independently is hydrogen; nitrogen protecting group; branched or unbranched, substituted or unsubstituted, cyclic or acyclic aliphatic; branched or unbranched, substituted or unsubstituted, cyclic or acyclic heteroaliphatic; substituted or unsubstituted aryl; or substituted or unsubstituted heteroaryl;

A is substituted or unsubstituted aryl; or substituted or unsubstituted heteroaryl;

each B independently is branched or unbranched, substituted or unsubstituted, cyclic or acyclic aliphatic; branched or unbranched, substituted or unsubstituted, cyclic or acyclic heteroaliphatic; substituted or unsubstituted aryl; or substituted or unsubstituted heteroaryl;

X$^1$ is a substituted or unsubstituted, cyclic or acyclic heteroaliphatic; or substituted or unsubstituted heteroarylene; and M is a transition metal.

In certain embodiments, each R$^3$ independently is hydrogen; branched or unbranched, substituted or unsubstituted, cyclic or acyclic aliphatic; or —N(R$_X$)$_2$, wherein each R$_X$ independently is hydrogen; nitrogen protecting group; branched or unbranched, substituted or unsubstituted, cyclic or acyclic aliphatic; branched or unbranched, substituted or unsubstituted, cyclic or acyclic heteroaliphatic; substituted or unsubstituted aryl; or substituted or unsubstituted heteroaryl. In certain embodiments, at least two R$^3$ are unbranched, unsubstituted, acyclic aliphatic. In certain embodiments, at least two R$^3$ are —CH$_3$. In certain embodiments, at least one R$^3$ is hydrogen. In certain embodiments, at least one R$^3$ is a branched or unbranched, substituted or unsubstituted, cyclic or acyclic aliphatic. In certain embodiments, at least one R$^3$ is —CH$_3$. In certain embodiments, at least one R$^3$ is —CF$_3$. In certain embodiments, at least one R$^3$ is —C(CH$_3$)$_3$. In certain embodiments, at least one R$^3$ is a —N(R$_X$)$_2$, wherein each R$_X$ independently is hydrogen; nitrogen protecting group; branched or unbranched, substituted or unsubstituted, cyclic or acyclic aliphatic; branched or unbranched, substituted or unsubstituted, cyclic or acyclic heteroaliphatic; substituted or unsubstituted aryl; or substituted or unsubstituted heteroaryl. In certain embodiments, at least one R$^3$ is a —N(CH$_3$)$_2$.

In certain embodiments,

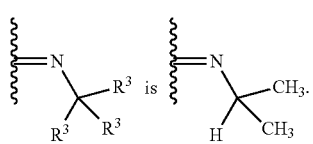

In certain embodiments,

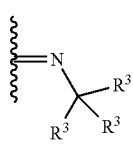

is

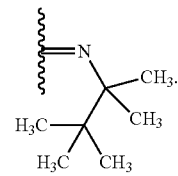

In certain embodiments,

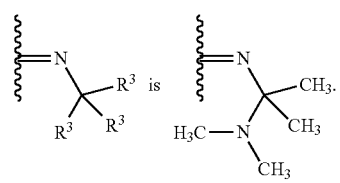

In certain embodiments, A is substituted or unsubstituted aryl. In certain embodiments, A is an unsubstituted aryl. In certain embodiments, A is a substituted phenyl. In certain embodiments, A is mesityl.

In certain embodiments, each B independently is substituted or unsubstituted aryl. In certain embodiments, each B is independently unsubstituted aryl. In certain embodiments, each B is independently substituted aryl. In certain embodiments, each B is the same. In certain embodiments, each B is different. In certain embodiments, each B is a substituted phenyl. In certain embodiments, each B is

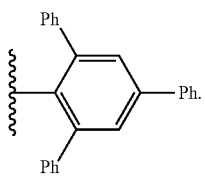

In certain embodiments, X$^1$ is substituted or unsubstituted heteroaryl. In certain embodiments, X$^1$ is unsubstituted 6-membered heteroaryl. In certain embodiments, X$^1$ is substituted 6-membered heteroaryl. In certain embodiments, X$^1$ is a substituted or unsubstituted pyridine, pyridazine, pyrimidine, pyrazine, triazine, or tetrazine. In certain embodiments, X$^1$ is a substituted or unsubstituted pyridine. In certain embodiments, X$^1$ is

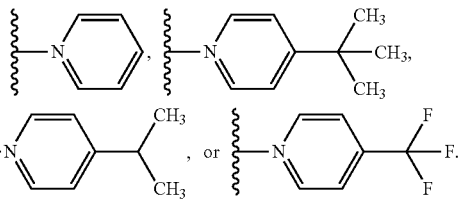

In certain embodiments, M is a transition metal selected from the group consisting of scandium, titanium, vanadium, chromium, manganese, iron, cobalt, nickel, copper, zinc, yttrium, zirconium, niobium, molybdenum, technetium, ruthenium, rhodium, palladium, silver, cadmium, lanthanum, hafnium, tantalum, tungsten, rhenium, osmium, iridium, platinum, gold, mercury, actinium, rutherfordium, seaborgium, bohrium, hassium, meitnerium, darmstadtium, and roentgenium. In certain embodiments, M is a transition metal selected from the group consisting of iron, cobalt, and nickel. In certain embodiments, M is iron. In certain embodiments, M is cobalt. In certain embodiments, M is nickel. In certain embodiments, the oxidation state of the metal is +1 (i.e., M(I)). In certain embodiments, the oxidation state of the metal is +2 (i.e., M(II)). In certain embodiments, the oxidation state of the metal is +3 (i.e., M(III)).

In certain embodiments, the compound of Formula (II) is selected from the group consisting of:

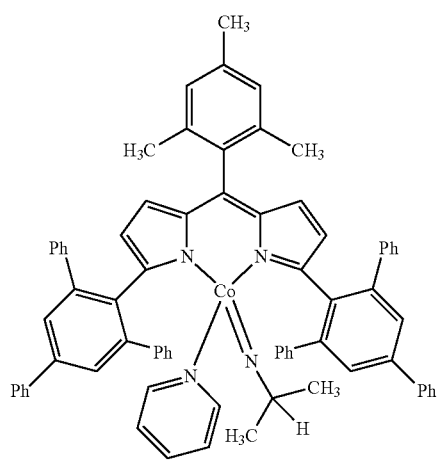

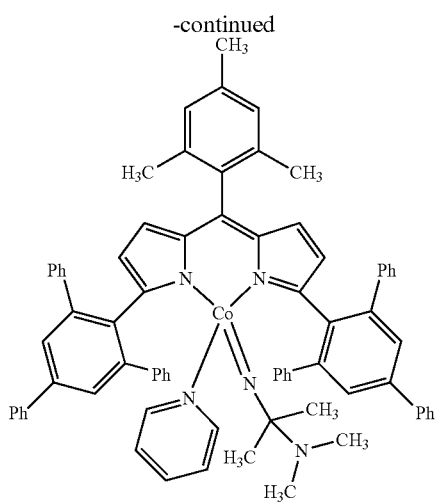

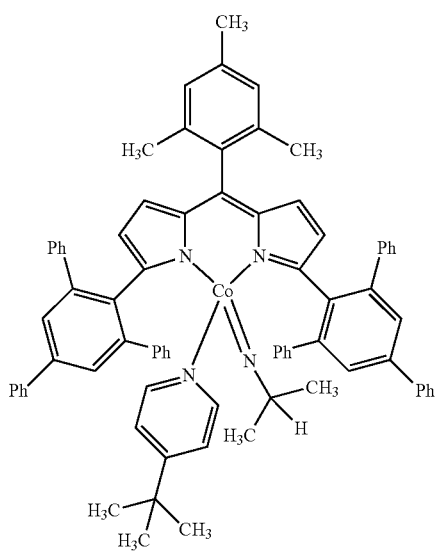

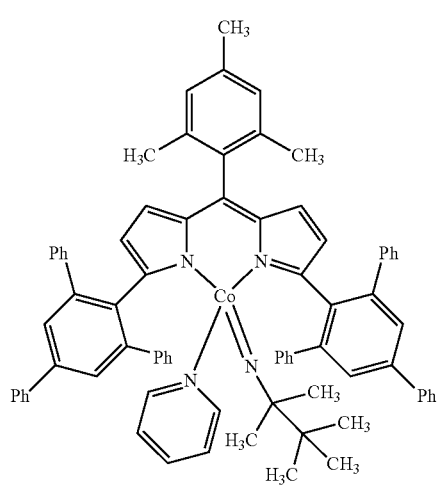

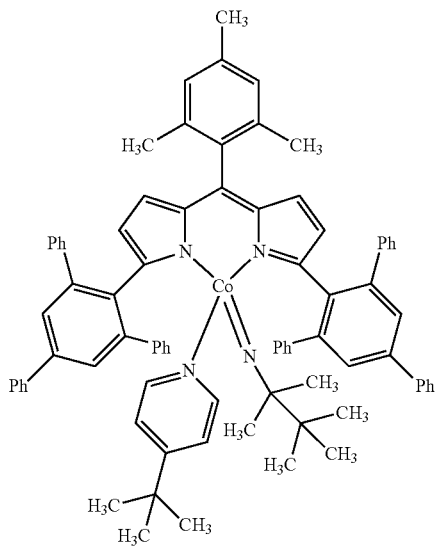

31
-continued
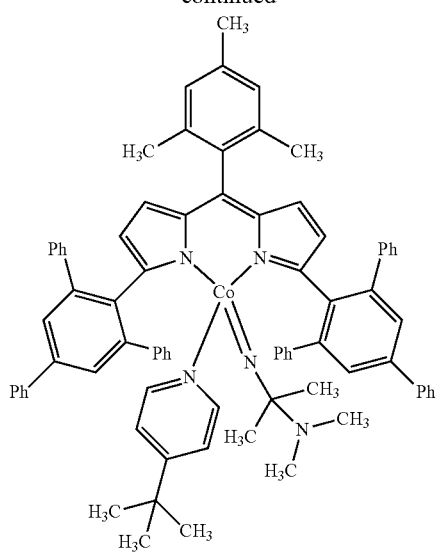
32
-continued
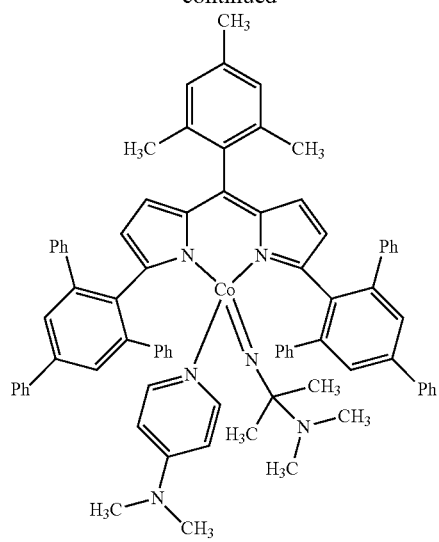
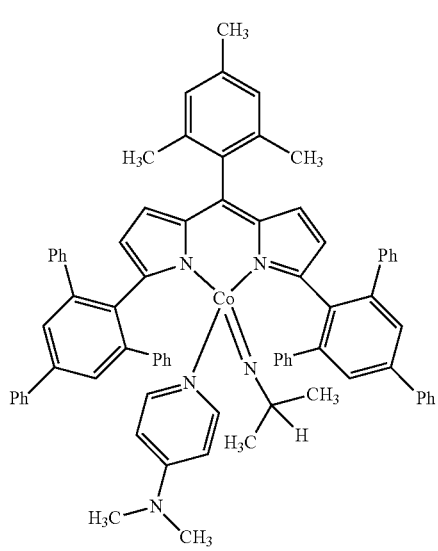
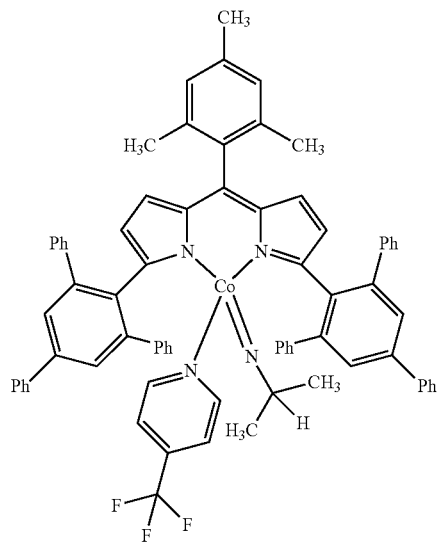
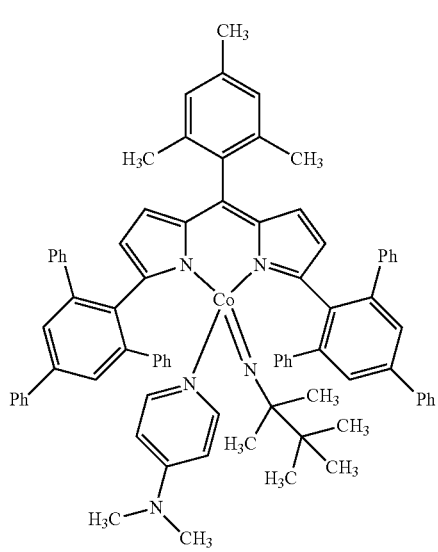
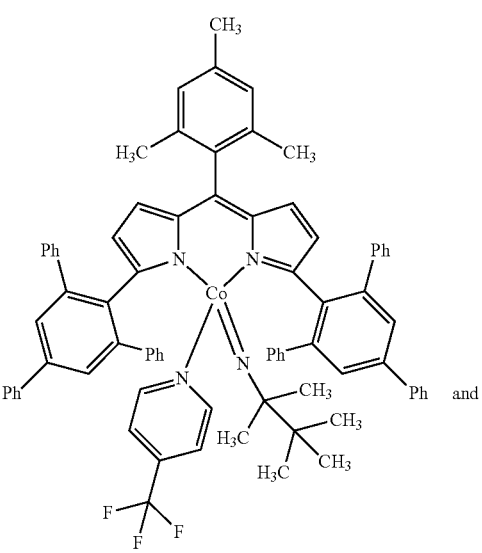
and -continued

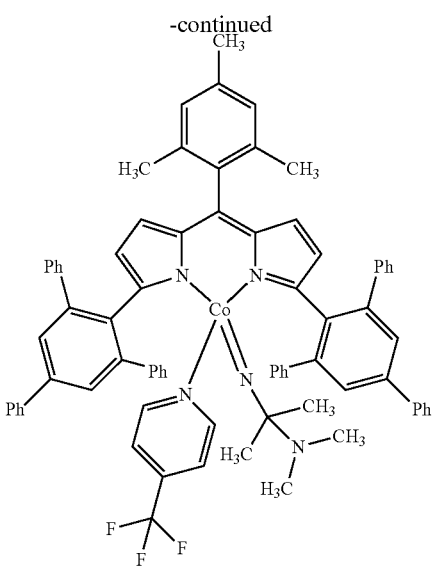

or a salt thereof.

The present disclosure encompasses compounds of Formula (III):

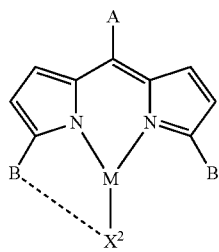

(III)

or a salt thereof,
wherein:

A is substituted or unsubstituted aryl; or substituted or unsubstituted heteroaryl;

each B independently is branched or unbranched, substituted or unsubstituted, cyclic or acyclic aliphatic; branched or unbranched, substituted or unsubstituted, cyclic or acyclic heteroaliphatic; substituted or unsubstituted aryl; or substituted or unsubstituted heteroaryl;

$X^2$ is branched or unbranched, substituted or unsubstituted, cyclic or acyclic heteroaliphatic; substituted or unsubstituted aryl; or substituted or unsubstituted heteroaryl;

⋯ is a bond or absent; and

M is a transition metal.

In certain embodiments, A is substituted or unsubstituted aryl. In certain embodiments, A is an unsubstituted aryl. In certain embodiments, A is a substituted phenyl. In certain embodiments, A is mesityl. In certain embodiments, A is

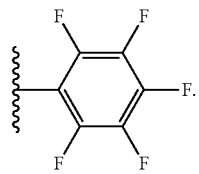 [SMILES: *c1c(F)c(F)c(F)c(F)c1F]

In certain embodiments, each B independently is branched or unbranched aliphatic. In certain embodiments, each B independently is substituted or unsubstituted aliphatic. In certain embodiments, each B independently is cyclic or acyclic aliphatic. In certain embodiments, each B independently is branched, substituted, and cyclic aliphatic. In certain embodiments, each B is different. In certain embodiments, each B is the same. In certain embodiments, B is

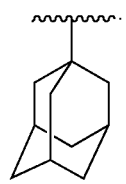 [SMILES: *C12CC3CC(CC(C3)C1)C2]

In certain embodiments, B is a substituted and acyclic aliphatic. In certain embodiments, B is

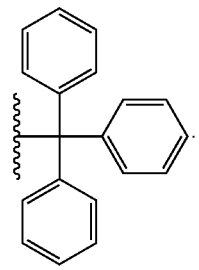 [SMILES: *C(c1ccccc1)(c1ccccc1)c1ccccc1]

In certain embodiments, B is

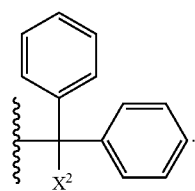

In certain embodiments, $X^2$ is substituted or unsubstituted aryl. In certain embodiments, $X^2$ is a substituted phenyl. In certain embodiments, $X^2$ is phenyl. In certain embodiments, $X^2$ is bonded to M via haptic bonding.

In certain embodiments, ⋯ is absent. In certain embodiments, $X^2$ is substituted or unsubstituted heteroaryl. In certain embodiments, $X^2$ is unsubstituted 6-membered heteroaryl. In certain embodiments, $X^2$ is substituted 6-membered heteroaryl. In certain embodiments, $X^2$ is substituted or unsubstituted pyridine, pyridazine, pyrimidine, pyrazine, triazine, or tetrazine. In certain embodiments, $X^2$ is unsubstituted 5-membered heteroaryl. In certain embodiments, $X^2$ is substituted 5-membered heteroaryl. In certain embodiments, $X^2$ is a substituted or unsubstituted pyrrole, furan, thiophene, imidazole, pyrazole, oxazole, isoxazole, thiazole, isothiazole, triazole, oxadiazole, thiadiazole, and tetrazole. In certain embodiments, $X^2$ is pyridine.

In certain embodiments, M is a transition metal selected from the group consisting of scandium, titanium, vanadium, chromium, manganese, iron, cobalt, nickel, copper, zinc, yttrium, zirconium, niobium, molybdenum, technetium, ruthenium, rhodium, palladium, silver, cadmium, lanthanum, hafnium, tantalum, tungsten, rhenium, osmium, iridium, platinum, gold, mercury, actinium, rutherfordium, seaborgium, bohrium, hassium, meitnerium, darmstadtium, and roentgenium. In certain embodiments, M is a transition metal selected from the group consisting of iron, cobalt, and nickel. In certain embodiments, M is iron. In certain embodiments, M is cobalt. In certain embodiments, M is nickel. In certain embodiments, the oxidation state of the metal is +1 (i.e., M(I)). In certain embodiments, the oxidation state of the metal is +2 (i.e., M(II)). In certain embodiments, the oxidation state of the metal is +3 (i.e., M(III)).

In certain embodiments, the compound of Formula (III) is

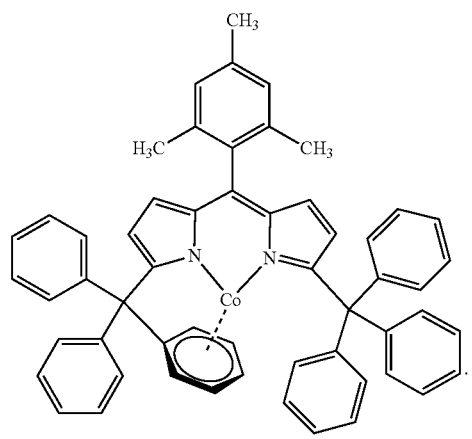

In certain embodiments, the compound of Formula (III) is

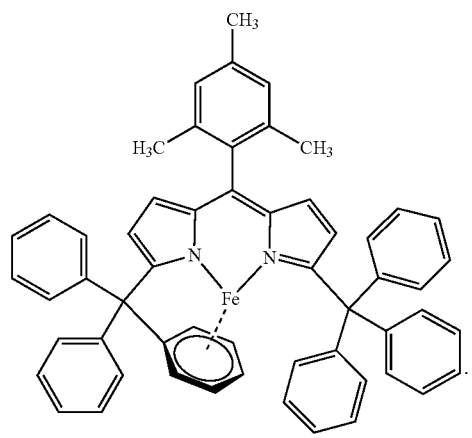

In certain embodiments, the compound of Formula (III) is

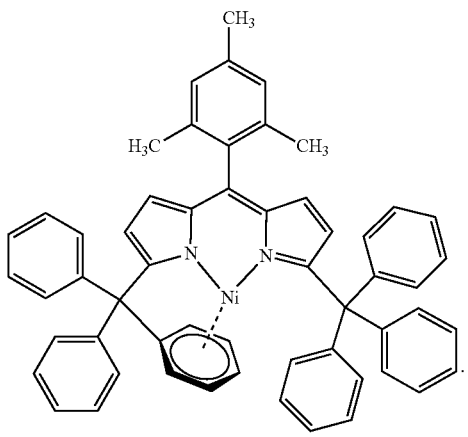

In certain embodiments, the compound of Formula (III) is

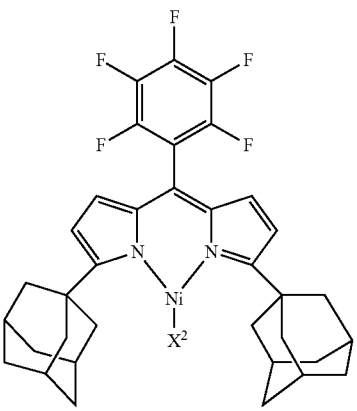

In certain embodiments, the compound of Formula (III) is

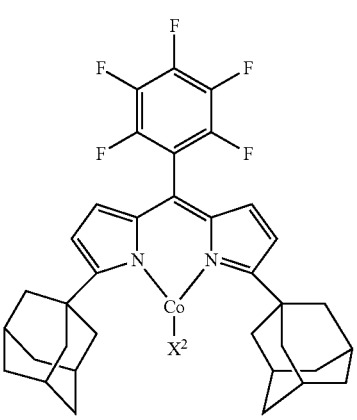

In certain embodiments, the compound of Formula (III) is

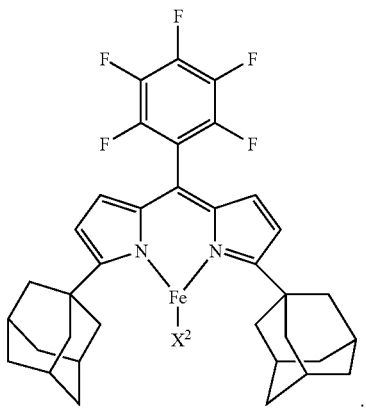

Polymeric Organometallic Compounds

Compounds in this disclosure are polymeric organometallic compounds, which contain at least one organic compound as a ligand coordinated to at least two metal atoms in a repeating fashion. In certain embodiments, the polymeric organometallic compound is a cyclic polymer.

The present disclosure describes compounds of Formula (I):

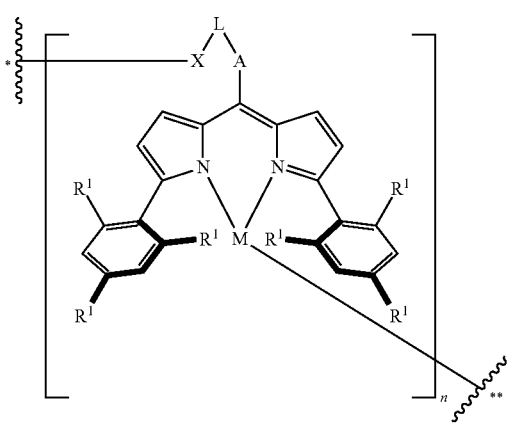

or a salt thereof,
wherein:
  each $R^1$ independently is branched or unbranched, substituted or unsubstituted, cyclic or acyclic aliphatic; branched or unbranched, substituted or unsubstituted, cyclic or acyclic heteroaliphatic; substituted or unsubstituted aryl; or substituted or unsubstituted heteroaryl;
  A is substituted or unsubstituted arylene; or substituted or unsubstituted heteroarylene;
  L is branched or unbranched, substituted or unsubstituted, cyclic or acyclic aliphatic; or branched or unbranched, substituted or unsubstituted, cyclic or acyclic heteroaliphatic;
  X is S, O, or $NR_X$, wherein $R_X$ is hydrogen; nitrogen protecting group; branched or unbranched, substituted or unsubstituted, cyclic or acyclic aliphatic; branched or unbranched, substituted or unsubstituted, cyclic or acyclic heteroaliphatic; substituted or unsubstituted arylene; or substituted or unsubstituted heteroarylene;
  M is a transition metal; and
  n is an integer between 2 and 10, inclusive;
  wherein the atom X labeled "*" of one monomer is bonded to the transition metal M labeled "**" of another monomer.

In certain embodiments, at least two $R^1$ are the same. In certain embodiments, each $R^1$ is the same. In certain embodiments, each $R^1$ independently is branched or unbranched aliphatic. In certain embodiments, each $R^1$ independently is substituted or unsubstituted aliphatic. In certain embodiments, each $R^1$ independently is cyclic or acyclic aliphatic. In certain embodiments, at least one $R^1$ is branched or unbranched aliphatic. In certain embodiments, at least one $R^1$ is substituted or unsubstituted aliphatic. In certain embodiments, at least one $R^1$ is cyclic or acyclic aliphatic. In certain embodiments, each $R^1$ independently is branched or unbranched heteroaliphatic. In certain embodiments, each $R^1$ independently is substituted or unsubstituted heteroaliphatic. In certain embodiments, each $R^1$ independently is cyclic or acyclic heteroaliphatic. In certain embodiments, at least one $R^1$ is branched or unbranched heteroaliphatic. In certain embodiments, at least one $R^1$ is substituted or unsubstituted heteroaliphatic. In certain embodiments, at least one $R^1$ is cyclic or acyclic heteroaliphatic. In certain embodiments, each $R^1$ independently is a substituted or unsubstituted aryl. In certain embodiments, each $R^1$ independently is a substituted or unsubstituted phenyl. In certain embodiments, each $R^1$ is phenyl.

In certain embodiments, A is substituted heteroarylene. In certain embodiments, A is unsubstituted heteroarylene. In certain embodiments, A is substituted heteroarylene. In certain embodiments, A is unsubstituted arylene. In certain embodiments, A is substituted phenylene. In certain embodiments, A is unsubstituted phenylene.

In certain embodiments, L is branched or unbranched aliphatic. In certain embodiments, L is substituted or unsubstituted aliphatic. In certain embodiments, L is cyclic or acyclic aliphatic. In certain embodiments, L is branched or unbranched heteroaliphatic. In certain embodiments, L is substituted or unsubstituted heteroaliphatic. In certain embodiments, L is cyclic or acyclic heteroaliphatic. In certain embodiments, L is unbranched, unsubstituted, acyclic aliphatic. In certain embodiments, L is unbranched, unsubstituted, acyclic $C_{1-6}$ aliphatic. In certain embodiments, L is —$CH_2$—.

In certain embodiments, X is S. In certain embodiments, X is $NR_X$, wherein $R_X$ is hydrogen; nitrogen protecting group; branched or unbranched, substituted or unsubstituted, cyclic or acyclic aliphatic; branched or unbranched, substituted or unsubstituted, cyclic or acyclic heteroaliphatic; substituted or unsubstituted arylene; or substituted or unsubstituted heteroarylene In certain embodiments, X is O.

In certain embodiments, M is a transition metal selected from the group consisting of scandium, titanium, vanadium, chromium, manganese, iron, cobalt, nickel, copper, zinc, yttrium, zirconium, niobium, molybdenum, technetium, ruthenium, rhodium, palladium, silver, cadmium, lanthanum, hafnium, tantalum, tungsten, rhenium, osmium, iridium, platinum, gold, mercury, actinium, rutherfordium, seaborgium, bohrium, hassium, meitnerium, darmstadtium, and roentgenium. In certain embodiments, M is a transition metal selected from the group consisting of iron, cobalt, and nickel. In certain embodiments, M is iron. In certain embodiments, M is cobalt. In certain embodiments, M is nickel. In certain embodiments, the oxidation state of the metal is +1 (i.e., M(I)). In certain embodiments, the oxidation state of the metal is +2 (i.e., M(II)). In certain embodiments, the oxidation state of the metal is +3 (i.e., M(III)).

In certain embodiments, n is an integer between 2 and 20, inclusive. In certain embodiments, n is an integer between 2 and 5, inclusive. In certain embodiments, n is an integer between 6 and 10, inclusive. In certain embodiments, n is an integer between 11 and 15, inclusive. In certain embodiments, n is an integer between 16 and 20, inclusive. In certain embodiments, n is an integer between 4 and 10, inclusive. In certain embodiments, n is an integer between 4 and 8, inclusive. In certain embodiments, n is an integer between 4 and 6, inclusive. In certain embodiments, n is 2. In certain embodiments, n is 6.

In certain embodiments, the compound of Formula (I) is of formula:

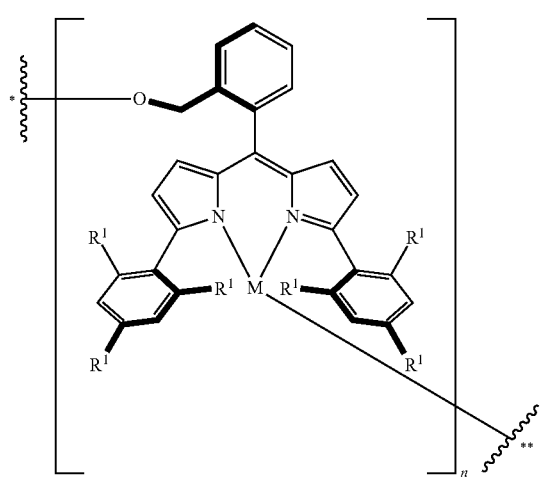

wherein:
- each $R^1$ independently is branched or unbranched, substituted or unsubstituted, cyclic or acyclic aliphatic; branched or unbranched, substituted or unsubstituted, cyclic or acyclic heteroaliphatic; substituted or unsubstituted aryl; or substituted or unsubstituted heteroaryl;
- M is a transition metal selected from the group consisting of iron, cobalt, and nickel; and
- n is an integer between 2 and 10, inclusive;

wherein the oxygen atom labeled "*" of one monomer is attached to the transition metal M labeled "**" of another monomer.

In certain embodiments, the compound of Formula (I) is of formula:

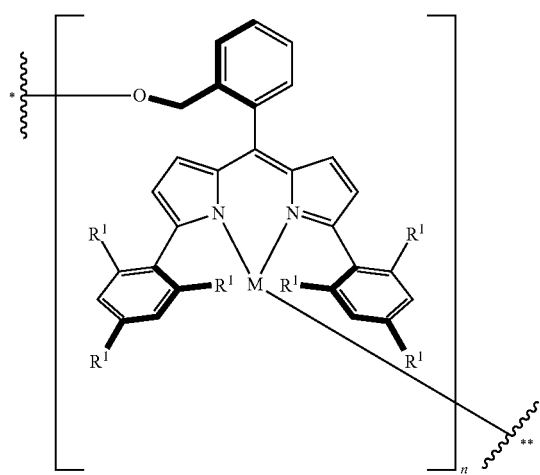

wherein:
- each $R^1$ independently is substituted or unsubstituted aryl; or substituted or unsubstituted heteroaryl;
- M is a transition metal selected from the group consisting of iron, cobalt, and nickel; and
- n is an integer between 2 and 10, inclusive;

wherein the oxygen atom labeled "*" of one monomer is attached to the transition metal M labeled "**" of another monomer.

In certain embodiments, the compound of Formula (I) is of formula:

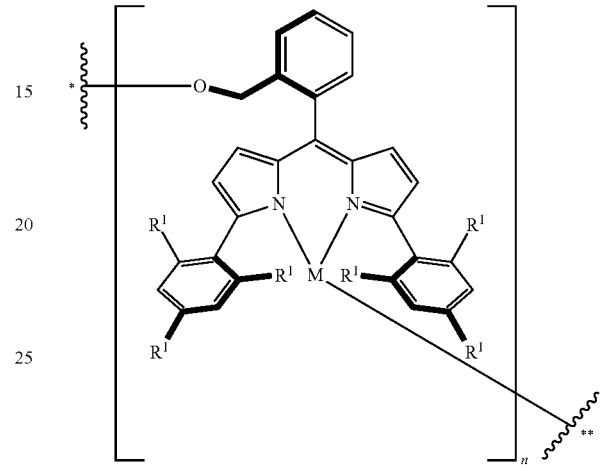

wherein:
- each $R^1$ independently is substituted or unsubstituted aryl; or substituted or unsubstituted heteroaryl;
- M is a transition metal selected from the group consisting of iron, cobalt, and nickel; and
- n is 6;

wherein the oxygen atom labeled "*" of one monomer is attached to the transition metal M labeled "**" of another monomer.

In certain embodiments, the compound of Formula (I) is of formula:

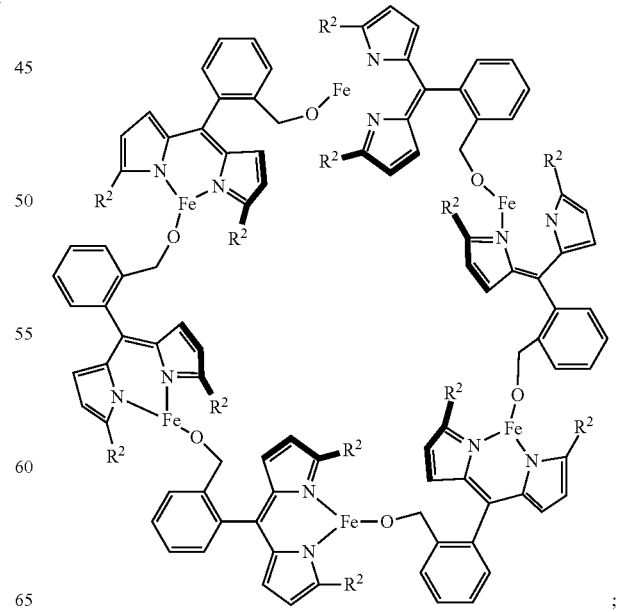

;

and each R² is of the formula

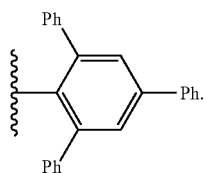 [SMILES: *c1c(-c2ccccc2)cc(-c2ccccc2)cc1-c1ccccc1]

In certain embodiments, the compound of Formula (I) is of formula:

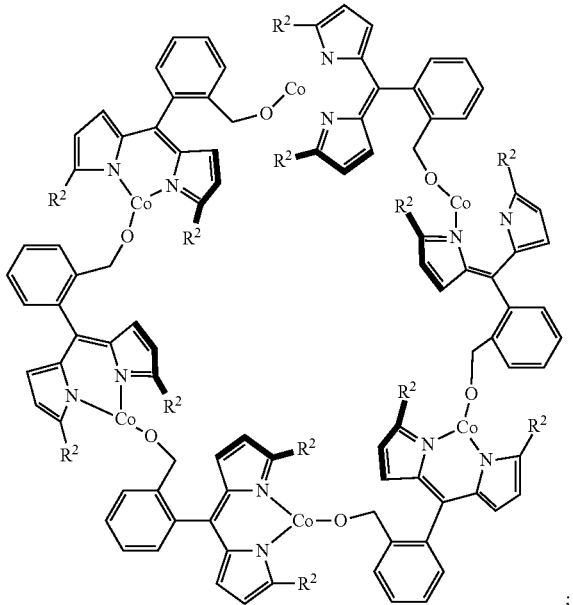

and each R² is of the formula

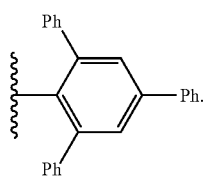 [SMILES: *c1c(-c2ccccc2)cc(-c2ccccc2)cc1-c1ccccc1]

In certain embodiments, the compound of Formula (I) is of formula:

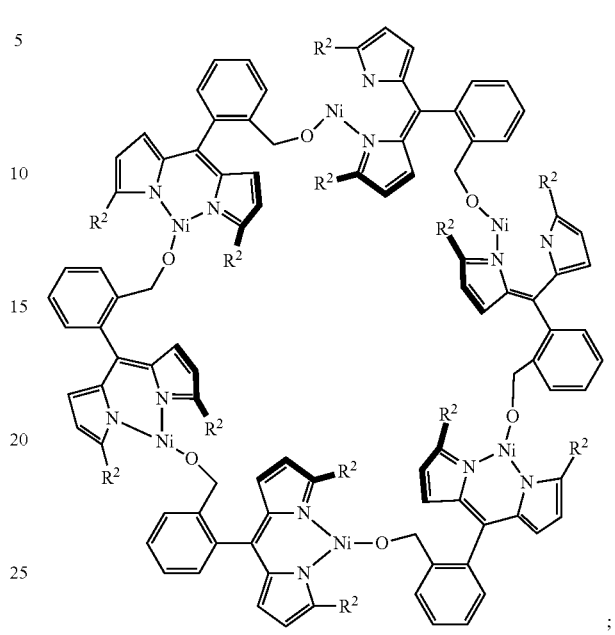

and each R² is of the formula

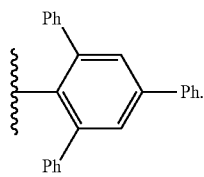

Methods of Preparation of Organometallic Compounds

In one aspect, the disclosure describes methods for the preparation of compounds of Formula (I), or salt thereof, comprising: reacting an compound of Formula (I-a) with an organometallic iron compound to produce a compound of Formula (I). In certain embodiments, the organometallic iron compound is $Fe_2(N(SiMe_3)_2)_4$.

In certain embodiments, the present disclosure encompasses compounds of Formula (I-a):

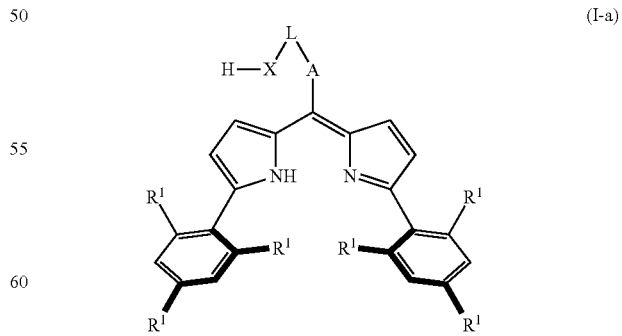

(I-a)

or a salt thereof,
wherein:
each $R^1$ independently is branched or unbranched, substituted or unsubstituted, cyclic or acyclic aliphatic;

branched or unbranched, substituted or unsubstituted, cyclic or acyclic heteroaliphatic; substituted or unsubstituted aryl; or substituted or unsubstituted heteroaryl;

A is substituted or unsubstituted arylene; or substituted or unsubstituted heteroarylene;

L is branched or unbranched, substituted or unsubstituted, cyclic or acyclic aliphatic; or branched or unbranched, substituted or unsubstituted, cyclic or acyclic heteroaliphatic; and X is S, O, or $NR_X$, wherein $R_X$ is hydrogen; nitrogen protecting group; branched or unbranched, substituted or unsubstituted, cyclic or acyclic aliphatic; branched or unbranched, substituted or unsubstituted, cyclic or acyclic heteroaliphatic; substituted or unsubstituted arylene; or substituted or unsubstituted heteroarylene.

In certain embodiments, $R^1$, A, L, and X are described herein with the same definitions as Formula (I).

In certain embodiments, the compound of Formula (I-a) is of formula:

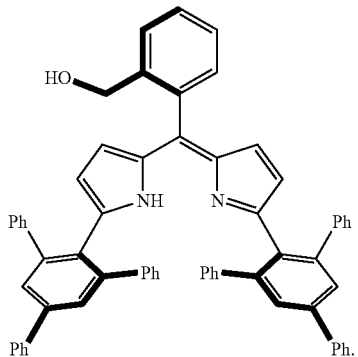

Methods of Utilizing Organometallic Compounds

In another aspect, the disclosure describes methods for the preparation of compounds of Formula (IV):

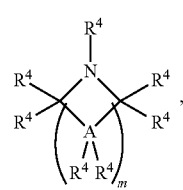

(IV)

or a salt thereof, comprising:
reacting an azide of Formula (IV-a) with a compound of Formula (I), Formula (II), or Formula (III) to produce a cyclic amine of Formula (IV);
wherein:
an azide of Formula (IV-a) is of formula

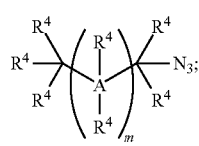

(IV-a)

each $R^4$ independently is hydrogen; branched or unbranched, substituted or unsubstituted, cyclic or acyclic aliphatic; branched or unbranched, substituted or unsubstituted, cyclic or acyclic heteroaliphatic; substituted or unsubstituted aryl; substituted or unsubstituted heteroaryl; two $R^4$ bonded to the same atom are taken together to form an oxo group or a cyclic aliphatic or cyclic heteroaliphatic moiety; two $R^4$ bonded to different atoms are taken together to form a cyclic aliphatic, cyclic heteroaliphatic, arylene, or heteroarylene moiety; two $R^4$ bonded to two adjacent atoms are replaced with a π bond between the two adjacent atoms; or absent;

m is an integer between 2 and 8, inclusive;

each A independently is C, S, O, or N.

In certain embodiments, at least two $R^4$ of an azide of Formula (IV-a) is hydrogen. In certain embodiments, all $R^4$ bonded to A are hydrogen. In certain embodiments, at least one $R^4$ is a branched or unbranched, substituted or unsubstituted, cyclic or acyclic $C_{1-6}$ aliphatic. In certain embodiments, $R^4$ is selected from a group consisting of —$CH_3$, —$CH_2CH_3$, —$CH_2CH_2CH_3$, —$CH_2(CH_2)_2CH_3$, —$CH(CH_3)_2$, —$CH_2CH(CH_3)_2$, or —$CH_2CH_2CH(CH_3)_2$. In certain embodiments, $R^4$ is —$CH_3$. In certain embodiments, at least one $R^4$ of

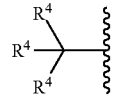

is substituted or unsubstituted aryl. In certain embodiments, two $R^4$ of

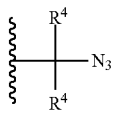

are taken together to form a cyclic aliphatic moiety. In certain embodiments, two $R^4$ of

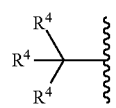

are taken together to form a cyclic aliphatic moiety.

In certain embodiments, one $R^4$ of

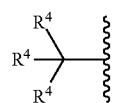

and one R⁴ of

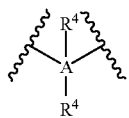

are taken together to form a cyclic aliphatic moiety. In certain embodiments, one R⁴ of

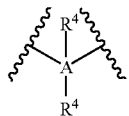

and one R⁴ of

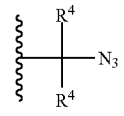

are taken together to form a cyclic aliphatic moiety. In certain embodiments, one R⁴ of

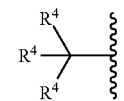

and one R⁴ of

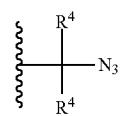

of an azide of Formula (IV-a) are taken together to form a cyclic aliphatic moiety. In certain embodiments, one R⁴ of

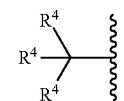

and one R⁴ of

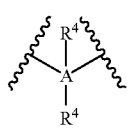

of an azide of Formula (IV-a) are taken together to form a cyclic heteroaliphatic moiety. In certain embodiments, one R⁴ of

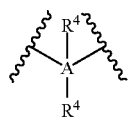

and one R⁴ of

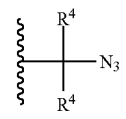

of an azide of Formula (IV-a) are taken together to form a cyclic heteroaliphatic moiety. In certain embodiments, one R⁴ of

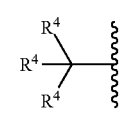

and one R⁴ of

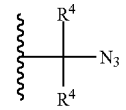

of an azide of Formula (IV-a) are taken together to form a cyclic heteroaliphatic moiety. In certain embodiments, one R⁴ of

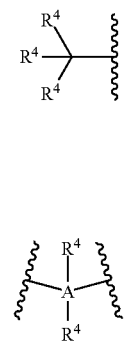

and one R⁴ of

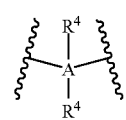

of an azide of Formula (IV-a) are taken together to form an arylene moiety. In certain embodiments, one R⁴ of and one R⁴ of

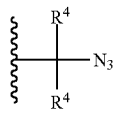

of an azide of Formula (IV-a) are taken together to form an arylene moiety. In certain embodiments, one R⁴ of

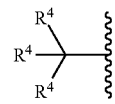

and one R⁴ of

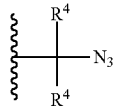

of an azide of Formula (IV-a) are taken together to form an arylene moiety. In certain embodiments, one R⁴ of

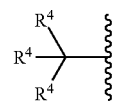

and one R⁴ of

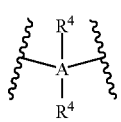

of an azide of Formula (IV-a) are taken together to form a heteroarylene moiety. In certain embodiments, one R⁴ of

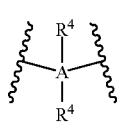

and one R⁴ of

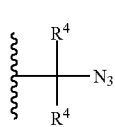

of an azide of Formula (IV-a) are taken together to form a heteroarylene moiety. In certain embodiments, one R⁴ of

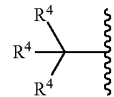

and one R⁴ of

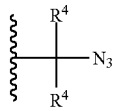

of an azide of Formula (IV-a) are taken together to form a heteroarylene moiety.

In certain embodiments, the azide of Formula (IV-a) is selected from the group consisting of:

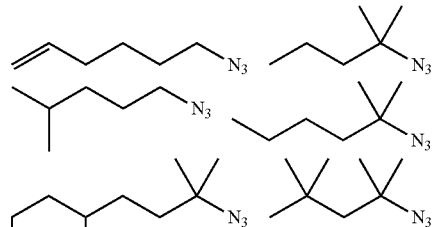

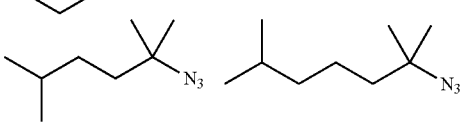

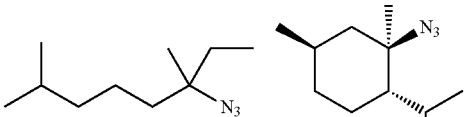

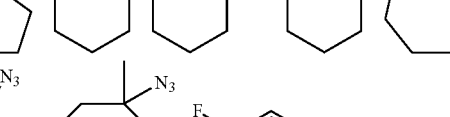

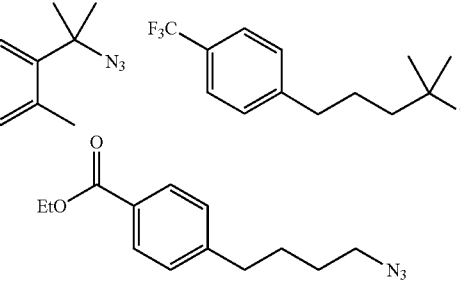

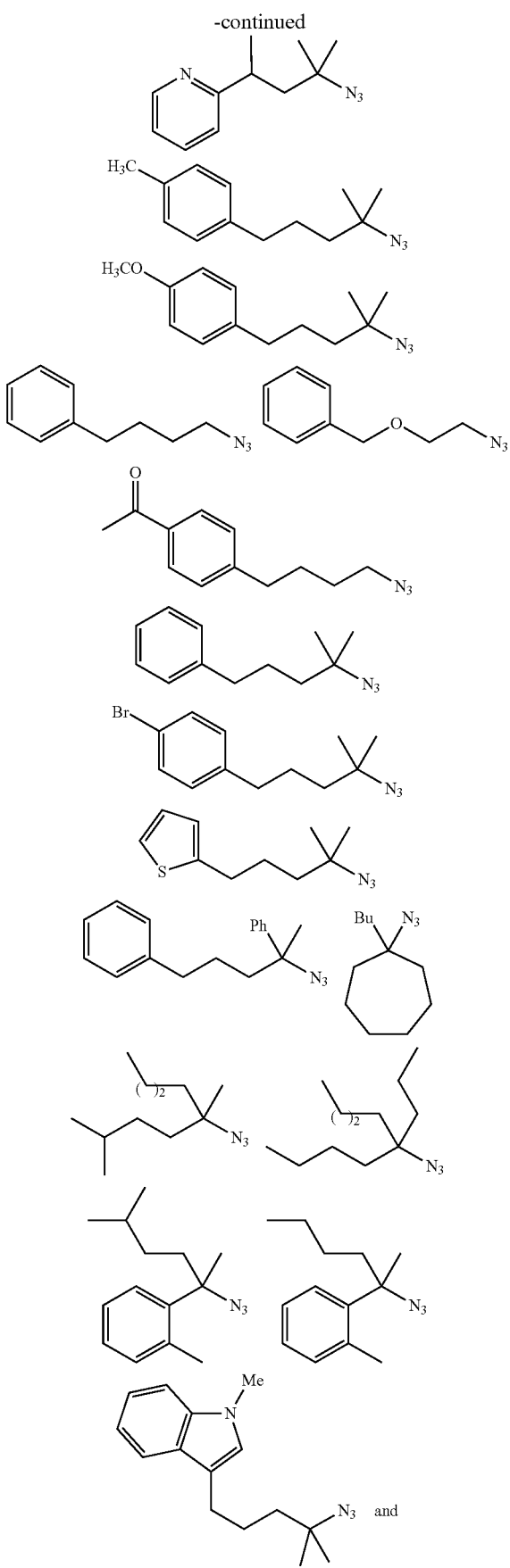

In certain embodiments, is prepared by reacting with a compound of Formula (I), (II), or (III). In certain embodiments, is prepared by reacting with a compound of Formula (I), (II), or (III).

In certain embodiments, the step of reacting an azide of Formula (IV-a) with a compound of Formula (I), Formula (II), or Formula (III) to produce a cyclic amine of Formula (IV) is performed in solvent. In certain embodiments, the step of reacting is performed in more than one solvent. In certain embodiments, the solvent is acetone, acetonitrile, benzene, benzonitrile, 1-butanol, 2-butanone, butyl acetate, tert-butyl methyl ether, carbon disulfide carbon tetrachloride, chlorobenzene, 1-chlorobutane, chloroform, cyclohexane, cyclopentane, 1,2-dichlorobenzene, 1,2-dichloroethane, dichloromethane (DCM), N,N-dimethylacetamide N,N-dimethylformamide (DMF), 1,3-dimethyl-3,4,5,6-tetrahydro-2-pyrimidinone (DMPU), 1,4-dioxane, 1,3-dioxane, diethylether, 2-ethoxyethyl ether, ethyl acetate, ethyl alcohol, ethylene glycol, dimethyl ether, heptane, n-hexane, hexanes, hexamethylphosphoramide (HMPA), 2-methoxyethanol, 2-methoxyethyl acetate, methyl alcohol, 2-methylbutane, 4-methyl-2-pentanone, 2-methyl-1-propanol, 2-methyl-2-propanol, 1-methyl-2-pyrrolidinone, dimethylsulfoxide (DMSO), nitromethane, 1-octanol, pentane, 3-pentanone, 1-propanol, 2-propanol, pyridine, tetrachloroethylene, tetrahyrdofuran (THF), 2-methyltetrahydrofuran, toluene, trichlorobenzene, 1,1,2-trichlorotrifluoroethane, 2,2,4-trimethylpentane, trimethylamine, triethylamine, N,N-diisopropylethylamine, diisopropylamine, water, o-xylene, or p-xylene. In certain embodiments, the solvent is benzene.

In certain embodiments, the step of reacting an azide of Formula (IV-a) with a compound of Formula (I), Formula (II), or Formula (III) to produce a cyclic amine of Formula (IV) is performed at a temperature between 10° C. and 150° C., inclusive. In certain embodiments, the temperature is between 10° C. and 50° C., inclusive. In certain embodiments, the temperature is between 10° C. and 20° C., inclusive. In certain embodiments, the temperature is between 20° C. and 30° C., inclusive. In certain embodiments, the temperature is between 30° C. and 40° C., inclusive. In certain embodiments, the temperature is between 40° C. and 50° C., inclusive. In certain embodiments, the temperature is between 50° C. and 100° C., inclusive. In certain embodiments, the temperature is between 50° C. and 60° C., inclusive. In certain embodiments, the temperature is between 60° C. and 70° C., inclusive. In certain embodiments, the temperature is between 70° C. and 80° C., inclusive. In certain embodiments, the temperature is between 80° C. and 90° C., inclusive. In certain embodiments, the temperature is between 90° C. and 100° C., inclusive. In certain embodiments, the temperature is between 100° C. and 150° C., inclusive. In certain embodiments, the temperature is between 100° C. and 110° C., inclusive. In certain embodiments, the temperature is between 110° C. and 120° C., inclusive. In certain embodiments, the temperature is between 120° C. and 130° C., inclusive. In certain embodiments, the temperature is between 130° C. and 140° C., inclusive. In certain embodiments, the temperature is between 140° C. and 150° C., inclusive. In certain embodiments, the temperature is about 25° C. In certain embodiments, the temperature is about 80° C. In certain embodiments, the temperature is about 100° C. In certain embodiments, the temperature is about 120° C.

In certain embodiments, a cyclic amine of Formula (IV) is produced by the reaction of azide of Formula (IV-a) with a compound of Formula (I).

In certain embodiments, a cyclic amine of Formula (IV) is produced by the reaction of azide of Formula (IV-a) with a compound of Formula (II).

In certain embodiments, a cyclic amine of Formula (IV) is produced by the reaction of azide of Formula (IV-a) with a compound of Formula (III).

Kits

In yet another aspect, the present disclosure provides kits for the preparation of a compound of Formula (I). In certain embodiments, the kits are comprised of: a) a compound of Formula (I-a) within a first container; b) an organometallic compound within a second container; c) optionally, one more solvents; and d) optionally, instructions for use.

In yet another aspect, the present disclosure provides kits for the preparation of a compound of Formula (IV). In certain embodiments, the kits are comprised of: a) a compound of a compound of Formula (I), Formula (II), or Formula (III) in a first container; b) an azide of Formula (IV-a) in a second container,

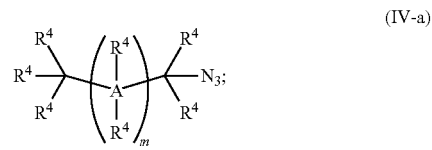

each $R^4$ independently is hydrogen; branched or unbranched, substituted or unsubstituted, cyclic or acyclic aliphatic; branched or unbranched, substituted or unsubstituted, cyclic or acyclic heteroaliphatic; substituted or unsubstituted aryl; substituted or unsubstituted heteroaryl; two $R^4$ bonded to the same atom are taken together to form an oxo group or a cyclic aliphatic or cyclic heteroaliphatic moiety; two $R^4$ bonded to different atoms are taken together to form a cyclic aliphatic, cyclic heteroaliphatic, arylene, or heteroarylene moiety; two $R^4$ bonded to two adjacent atoms are replaced with a π bond between the two atom; or absent; m is an integer between 2 and 8, inclusive; each A independently is C, S, O, or N; c) optionally, one more solvents; and d) optionally, instructions for use.

EXAMPLES

In order that the invention described herein may be more fully understood, the following examples are set forth. The synthetic examples described in this application are offered to illustrate the compounds and methods provided herein and are not to be construed in any way as limiting their scope.

Materials and Methods.

All manipulations involving metal complexes were carried out under a nitrogen atmosphere using standard Schlenk techniques, or an MBraun inert atmosphere drybox. Ligand and substrate syntheses were carried out under air unless specified otherwise. All glassware that was used in air and moisture free reactions was oven dried and cooled in an evacuated antechamber or under high vacuum prior to use. Solvents used in air and moisture free reactions were dried and deoxygenated on a Glass Contour System (SG Water USA, Nashua, NH) and stored over 4 Å molecular sieves (Strem) prior to use. Dimethylsulfoxide, hydrobromic acid (48%), pyridine (anhydrous), pentane (anhydrous) and dimethylformamide (anhydrous) were purchased from VWR and used as received. Chloroform-d was purchased from Cambridge Isotope Labs and used as received. Benzene-d6 was purchased from Cambridge Isotope Labs and was degassed and stored over 4 Å molecular sieves prior to use. 2-bromobenzaldehyde diethyl acetal, ethyl-5-bromo-valerate, benzyl-2-bromo ether, 4-phenyl-1-butanol, 4,4,2-trimethyl-2-pentanol, indole-3-butyric acid, 1-methylcyclohexanol, 2-phenyl-2-pentanol, 2-methyl-2-hexanol, 2-methyl-2-butanol, cycloheptanone, 4-methylbromopentane, 2-methyl-2-pentanol, 1-bromocyclohexane, (2S,5R)-2-isopropyl-5-methylcyclohexanone, litocholic acid, 2-bromopyridine were purchased from Sigma Aldrich and liquids were distilled under a nitrogen atmosphere. n-Butyl lithium (2.5 M in hexanes), pyridinium p-toluenesulfonate (PPTS) and 2,3-dichloro-5,6-dicyano-1,4-benzoquinone (DDQ) were purchased from Aldrich and used as received. Anhydrous iron (II) chloride, diethyl zinc (10% w/w in hexanes) and sodium borohydride were purchased from Strem and used as received. 2-(2,4,6-triphenylphenyl)pyrrole, iron bis-trimethylsilyl amide and tosyl azide were synthesized according to literature procedures. Celite® 545 (J. T. Baker) and 4 Å molecular sieves were dried in a Schlenk flask for 24 h under dynamic vacuum while heating to at least 200° C. prior to use in a drybox. Silica gel 32-63μ (AIC, Framingham, MA) was used as received.

$^1$H and $^{13}$C NMR spectra were recorded on Varian Mercury 400 MHz or Varian Unity/Inova 500 MHz spectrometers. $^1$H and $^{13}$C NMR chemical shifts are reported relative to a residual solvent peak as reference. Infrared (FTIR) spectra were recorded on a Varian 1000 Scimitar FT-IR spectrophotometer referenced to a polystyrene standard. Gas chromatography/mass spectrometry (GC/MS) was performed on a Shimadzu GCMS-QP2010S. High resolution mass spectrometry was carried out by Small Molecules Mass Spectrometry laboratories at Harvard division of science core facility (Cambridge, MA) Elemental analyses were carried out by Complete Analysis Laboratories, Inc. (Parsippany, NJ).

Zero-field $^{57}$Fe Mössbauer spectra were measured with a constant acceleration spectrometer (SEE Co, Minneapolis, MN) at 90 K. Isomer shifts are quoted relative to Fe foil at room temperature. Data was analyzed and simulated with Igor Pro 6 software (WaveMetrics, Portland, OR) using Lorentzian fitting functions. Samples were prepared by suspending 20-40 mg of compound in sufficient Paratone oil and immobilizing by rapid freezing in liquid nitrogen.

CAUTION: Caution has to be exercised during preparation and handling of organic azides since they are known to be potentially explosive compounds. All organic azides were stored at −35° C. in a glovebox.

Example 1: Ligand Synthesis

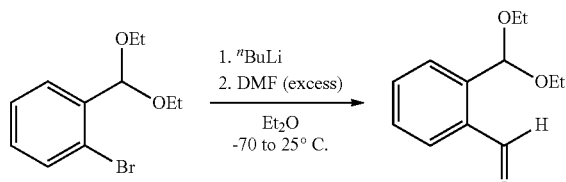

2-Diethoxymethyl Benzaldehyde

Freshly distilled 2-bromobenzaldehyde diethyl acetal (10.1 g, 39.0 mmol) was dissolved in dry diethyl ether under N$_2$ atmosphere. The reaction mixture was cooled to −78° C. using dry ice and acetone. A solution of n-BuLi in hexanes (2.5 M, 22.5 mL, 47 mmol) was added dropwise to the reaction mixture. The reaction mixture was allowed to warm to room temperature and stirred for additional 15 minutes to give a cloudy suspension with a white precipitate. The reaction mixture was cooled back to −78° C. and dry dimethylformamide (31.5 g, 0.43 mol) was added. The reaction was brought to room temperature and stirred for additional 12 hours and quenched with a saturated aqueous solution of ammonium chloride (4.21 g, 78 mmol). The product was extracted with diethyl ether (2×250 mL) and the combined organic phase was dried over MgSO$_4$ and concentrated on a rotary evaporator to yield the desired product as cloudy off-white oil (6.00 g, 73%) that was used in the following step without further purification. $^1$H NMR (500 MHz, C$_6$D$_6$): δ/ppm 10.60 (s, 1H), 7.87 (d, J=7.7 Hz, 1H), 7.55 (d, J=7.2 Hz, 1H), 7.24-7.11 (m, 1H), 7.10-6.96 (m, 1H), 5.75 (s, 1H), 3.55-3.39 (m, 2H), 3.39-3.17 (m, 2H), 1.02 (t, J=7.1 Hz, 6H). $^{13}$C{$^1$H} NMR (126 MHz, C$_6$D$_6$): δ/ppm 192.05, 141.82, 135.16, 133.3, 129.64, 129.18, 128.09, 109.13, 62.57, 15.64.

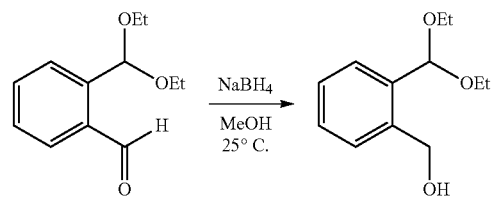 [SMILES: CCOC(OCC)c1ccccc1C=O ; "NaBH4" ; CCOC(OCC)c1ccccc1CO]

(2-(Diethoxymethyl)phenyl)methanol 2-(diethoxymethyl)-benzaldehyde (5.50 g, 26 mmol) was dissolved in MeOH (180 mL) and NaBH$_4$ (1.20 g, 32 mmol) was added in portions. The reaction mixture was stirred for 12 hours and quenched with a saturated aqueous solution of ammonium chloride (5.68 g, 0.11 mol). The organic phase was extracted with diethyl ether (2×250 mL), washed with brine (100 mL) followed by water (100 mL) and dried over MgSO$_4$. The solution was concentrated on a rotary evaporator to give the product as a colorless oil (4.50 g, 81%). $^1$H NMR (500 MHz, C$_6$D$_6$): δ/ppm 7.67-7.51 (m, 1H), 7.49-7.31 (m, 1H), 7.21-7.05 (m, 2H), 5.51 (s, 1H), 4.78 (s, J=6.5 Hz, 2H), 3.70 (s (br), 1H), 3.49-3.35 (m, 2H), 3.35-3.20 (m, 2H), 1.02 (t, J=7.1 Hz, 6H). $^{13}$C{$^1$H} NMR (126 MHz, C$_6$D$_6$): δ/ppm 140.53, 137.30, 129.76, 129.27, 127.80, 127.53, 101.49, 63.27, 61.85, 15.60.

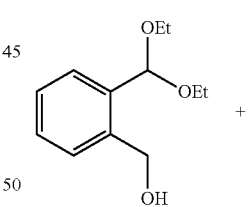

+

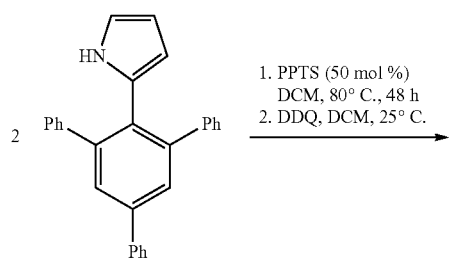

-continued

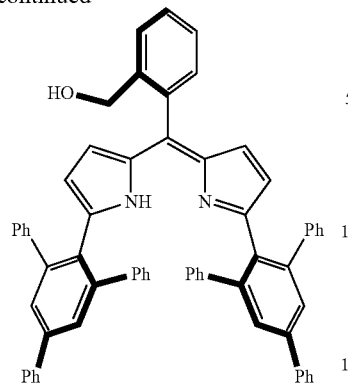

Step 1: Dipyrromethane

Under inert atmosphere, a 1 L pressure vessel was charged with 2-methoxybenzaldehyde diethyl acetal (1.5 g, 6.7 mmol), 2-(2,4,6-triphenylphenyl) pyrrole (5.0 g, 14 mmol) and PPTS (0.85 g, 3.4 mmol). The pressure vessel was tightly sealed and heated to 80° C. for 48 hours to give a bright purple solution. The reaction mixture was dry-loaded on to a silica gel column and the product was eluted using an ethyl acetate:hexanes (1:3, v/v) solvent mixture ($R_f$=0.2). The resulting yellow orange solid was washed with 20 mL of MeOH to give a yellow powder (1.21 g, 21%) that was used in the following step without further purification. $^1$H NMR (400 MHz, $C_6D_6$): δ/ppm 7.65 (s, 4H), 7.51-7.42 (m, 4H), 7.28-7.18 (m, 15H), 7.12-6.96 (m, 15H), 5.78-5.67 (m, 2H), 5.48-5.37 (m, 2H), 5.25 (s, 1H), 4.14 (d, J=5.8 Hz, 2H).

Step 2: ($^{Ar}L_O$)H (1)

Dipyrromethane (1.2 g, 1.4 mmol) was dissolved in 180 mL of dichloromethane in a 200 mL round bottom flask charged with a stir bar. DDQ (0.348 g, 1.5 mmol) was added as a solid to give an instantaneous change of color from orange to deep purple. The reaction was stirred at room temperature for additional 6 hours. The crude product was dry loaded on to a silica gel column and was eluted using ethyl acetate:hexanes (1:9, v/v) as a solvent mixture ($R_f$=0.7). The product was further purified by washing with MeOH (2×10 mL) to give a bright red-pink powder (0.874 g, 73%). $^1$H NMR (400 MHz, $C_6D_6$): δ/ppm 7.62 (s, 4H), 7.53 (s, 1H), 7.50-7.42 (m, 4H), 7.29-7.19 (m, 14H), 7.11-6.94 (m, 14H), 6.82 (d, J=7.5 Hz, 1H), 6.73 (d, J=7.5 Hz, 1H), 5.72 (t, J=3.0 Hz, 2H), 5.64-5.56 (t, J=3.1 Hz, 2H), 4.56 (s, 2H). $^{13}C\{^1H\}$NMR (126 MHz, $C_6D_6$): δ/ppm 143.97, 143.33, 142.67, 140.89, 140.70, 139.53, 133.20, 130.22, 129.56, 129.17, 128.78, 127.50, 127.44, 126.91, 123.27, 120.76, 112.10, 108.49, 85.39, 70.46. HRMS (ESI$^+$) m/z Calc. 859.3683 [$C_{64}H_{46}N_2O+H^+$], Found 859.3720 [M+H]$^+$.

Example 2: Synthesis of [($^{Ar}L_O$)Fe]$_6$ (2)

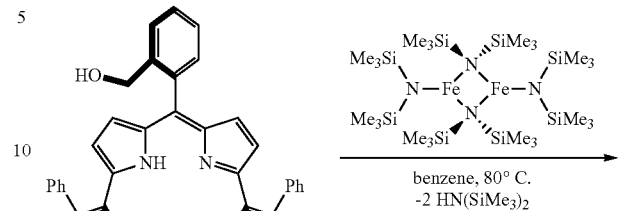

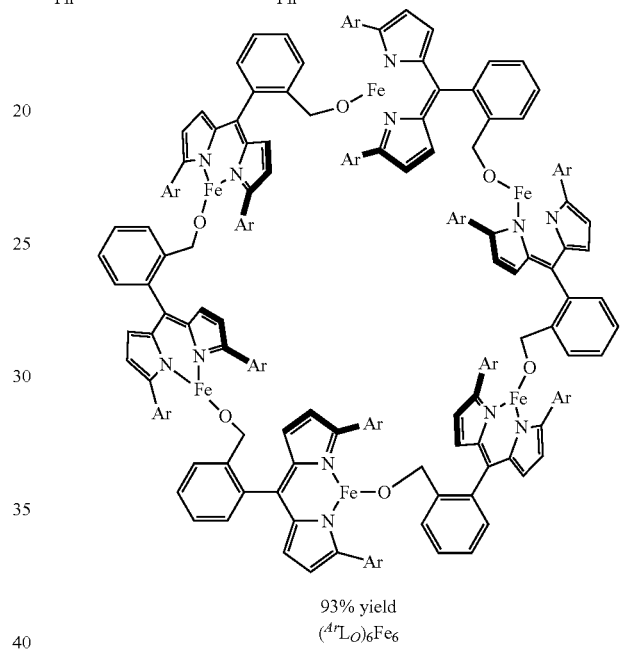

93% yield
($^{Ar}L_O$)$_6$Fe$_6$

Under an inert atmosphere, iron bis-trimethylsilyl amide (0.38 g, 0.5 mmol) was dissolved in dry benzene (20 mL) and transferred into a 150 mL pressure vessel to give a light green solution. ($^{Ar}L_O$)H (0.80 g, 0.90 mmol) was dissolved in benzene and added to the reaction mixture to give a bright purple-pink solution. The pressure vessel was sealed and heated at 80° C. for 24 hours to give a dark pink solution and a brown precipitate. In a nitrogen glove box, 20 mL of hexanes was added to the reaction mixture. The precipitate was filtered using a medium porosity glass frit and washed with hexanes (3×20 mL) to give a deep purple-pink powder (0.80 g, 94%). NMR analysis was not conclusive due to low solubility of the complex in common noncoordinating solvents like benzene-d6 and decomposition of the complex in dichloromethane-d2 and DMSO-d6. The structure of the complex was confirmed by preliminary X-diffraction analysis of microcrystals that were grown by slow cooling of a concentrated toluene solution of the complex (120° C. to room temperature). The poor quality of the crystals, due to solvent disorder and low resolution, does not allow us to report a full refinement, but allowed determination of the atom connectivity and relative coordination geometry around the metal center. Analysis of the bulk material by elemental analysis and $^{57}$Fe Mössbauer spectroscopy confirmed the proposed structure. Zero-field $^{57}$Fe Mössbauer (90 K): (δ, |ΔE$_Q$| (mm/s)): 0.7, 0.75. % CHN Calculated for C$_{384}$H$_{270}$Fe$_6$N$_{12}$O$_6$ C, 84.20, H, 4.86, N, 3.07, Found: C, 84.11, H, 5.06, N, 3.42.

Example 3: Synthesis of [($^{Ar}$L$_O$)Fe(py)]$_2$ (3)

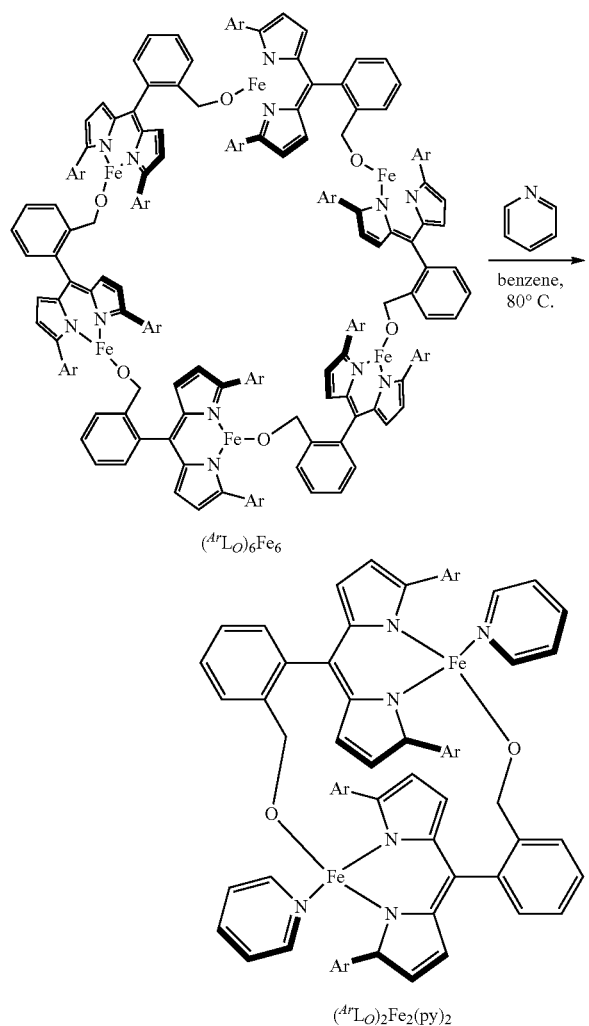

[($^{Ar}$L$_O$)Fe]$_6$ (0.050 g) was dissolved in 10 mL of benzene and transferred to a 50 mL pressure vessel charged with a stirring bar. Excess of dry pyridine was added to the solution and the reaction mixture was tightly sealed and heated at 80° C. for 2 hours and allowed to cool to the room temperature to give a pink solution with a dark precipitate. The precipitate was filtered and washed with hexanes (2×20 mL) to give a purple powder. Crystals suitable for X-ray diffraction analysis were grown by slow cooling of the concentrated benzene solution (100° C. to room temperature). Zero-field $^{57}$Fe Mössbauer (90 K): (δ, |ΔE$_Q$| (mm/s)): 0.9, 2.18.

Catalytic Amination Reactions.

1. General Procedure for the Catalytic Formation of N-Heterocyclic Amines

In a nitrogen-filled glovebox, the desired azide (1 equiv) and the catalyst [Fe] (0.01-0.05 equiv), where [Fe]=1/6 [($^{Ar}$L$_O$)Fe]$_6$ (2), were dissolved in 2 mL of benzene-d6 to give a bright pink-purple suspension. The reaction mixture was transferred into a J. Young tube and heated at the desired temperature. The progression of the reaction was monitored by $^1$H NMR.

2. Conversion Determination for the Catalytic Amination Reaction

Ferrocene was added to the mixture upon completion of the reaction. The ratio of the area under the ferrocene proton resonance and diagnostic protons of the product was used to calculate the yield of the reaction. The procedure was repeated at least two times and the average conversion yield is reported.

3. Product Isolation for the Catalytic Amination Reaction

The reaction was performed as described above. The reaction mixture was transferred into a round bottom flask that was attached to a vacuum transfer apparatus. The system was subjected to a static high vacuum and the receiving flask was cooled with liquid nitrogen. After the transfer was complete, the solvent was removed via lyophilization to give pure product that was further analyzed by various spectroscopic methods.

Procedures for the Catalytic Formation of N-Heterocyclic Amines

Example 4

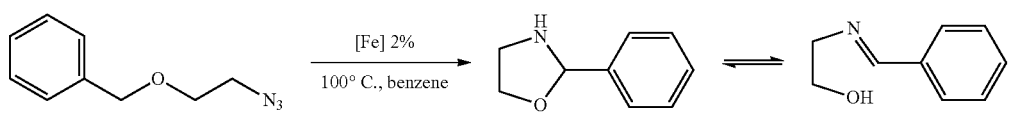 [SMILES: [N-]=[N+]=NCCOCc1ccccc1 ; c1ccc(C2NCCO2)cc1 ; OCC/N=C/c1ccccc1]

2-Phenyloxazolidine (6b): The general procedure for the catalytic formation of N-heterocyclic amines was followed. Temperature and time of the reaction were 100° C. and 48 hours, respectively. Run 1: Reagents: benzyl-2-azido ether (6a) (0.050 g, 1 equiv) and [Fe] (0.0052 g, 0.02 equiv). Ferrocene (0.0243 g, 13 mmol) was added to the reaction mixture. The $^1$H NMR spectrum of the resulting solution showed that the ratio of the area under the ferrocene proton resonance and the protons of CH$_2$ group of 2-phenyloxazolidine (6b) is 2.41 to 1.00, respectively. Calculated yield of 2-phenyloxazolidine is 96%. Run 2: Reagents: benzyl-2-azido ether (6a) (0.050 g, 0.28 mmol, 1 equiv) and [Fe] (0.0052 g, 0.02 equiv). Ferrocene (0.0096 g, 0.51 mmol) was added to the reaction mixture. The $^1$H NMR spectrum of the resulting solution showed that the ratio of the area under ferrocene proton resonance and the protons of CH$_2$ group of 2-phenyloxazolidine (6b) is 1.04 to 1.00, respectively. Calculated yield of 2-phenyloxazolidine is 91%. Product isolation: Isolation of the product was complicated due to instability of the oxazolidine to hydrolysis. A derivative of 2-phenyloxazolidine (6b) was prepared via reduction with NaBH$_4$ to confirm the identity of the product.

Example 5

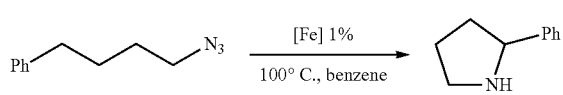

2-Phenylpyrrolidine (5b): The general procedure for the catalytic formation of N-heterocyclic amines was followed. Temperature and time of the reaction were 100° C. and 1.5 hours, respectively. Run 1: Reagents: 4-phenyl-1-azidobutane (5a) (0.043 g, 0.25 mmol, 1 equiv) and [Fe] (0.0020 g, 0.01 equiv). Ferrocene (0.0091 g, 0.049 mmol) was added to the reaction mixture. The $^1$H NMR spectrum of the resulting solution showed that the ratio of the area under ferrocene proton resonance and the protons of CH(Ph) group of 2-phenylpyrrolidine (5b) is 2.20 to 1.00, respectively. Calculated yield of 2-phenylpyrrolidine (5b) is 91%. Run 2: Reagents: 4-phenyl-1-azidobutane (5a) (0.046 g, 0.026 mmol, 1 equiv) and [Fe] (0.0020 g, 0.01 equiv). Ferrocene (0.0098 g, 0.049 mmol) was added to the reaction mixture. The $^1$H NMR spectrum of the resulting solution showed that the ratio of the area under the ferrocene proton resonance and the protons of CH(Ph) group of 2-phenylpyrrolidine (5b) is 2.27 to 1.00, respectively. Calculated yield of 2-phenylpyrrolidine (5b) is 88%. Product isolation: Reagents: 4-phenyl-1-azidobutane (5a) (0.100 g, 0.57 mmol, 1 equiv) and [Fe] (0.0052 g, 0.01 equiv). The product was isolated via vacuum transfer as described in the general isolation protocol to yield 2-phenyl pyrrolidine (5b) (0.066 g, 78%). Spectroscopic and physical characterization of 2-phenyl pyrrolidine (5b) were previously reported. $^1$H NMR (500 MHz, C$_6$D$_6$): δ/ppm 7.41 (d, J=7.2 Hz, 2H), 7.26-7.19 (m, 2H), 7.12 (t, J=7.4 Hz, 1H), 3.84 (t, J=7.6 Hz, 1H), 3.02-2.89 (m, 1H), 2.75-2.58 (m, 1H), 1.95-1.81 (m, 1H), 1.71-1.56 (m, 1H), 1.54-1.42 (m, 2H). $^{13}$C{$^1$H} NMR (126 MHz, C$_6$D$_6$): δ/ppm 128.50, 126.95, 126.85, 62.72, 47.00, 35.24, 25.68.

Example 6

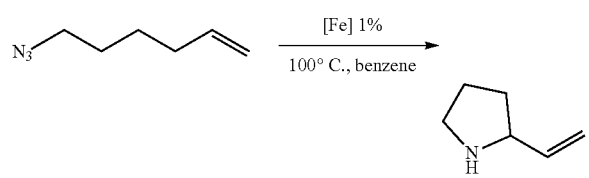

2-Vinylpyrrolidine (4b): The general procedure for the catalytic formation of N-heterocyclic amines was followed. Temperature and time of the reaction were 100° C. and 1.5 hours, respectively. Run 1: Reagents: 6-azido-1-hexene (4a) (0.038 g, 0.30 mmol, 1 equiv) and [Fe] (0.0029 g, 0.01 equiv). Ferrocene (0.011 g, 0.059 mmol) was added to the reaction mixture. The $^1$H NMR spectrum of the resulting solution showed that the ratio of the area under the ferrocene proton resonance and the protons of CH(CH—CH$_2$) group of 2-vinylpyrrolidine (4b) is 2.34 to 1.00, respectively. Calculated yield of 2-vinylpyrrolidine (4b) is 82%. Run 2: Reagents: 6-azido-1-hexene (4a) (0.030 g, 0.24 mmol, 1 equiv) and [Fe] (0.0029 g, 0.01 equiv). Ferrocene (0.0097 g, 0.052 mmol) was added to the reaction mixture. The $^1$H NMR spectrum of the resulting solution showed that the ratio of the area under the ferrocene proton resonance and the protons of CH(CH—CH$_2$) group of 2-vinylpyrrolidine (4b) is 2.8 to 1.00, respectively. Calculated yield of 2-vinylpyrrolidine (4b) is 78%. Product isolation: Reagents: 6-azido-1-hexene (4a) (0.100 g, 0.79 mmol, 1 equiv) and [Fe] (0.0073 g, 0.01 equiv). The product was isolated via vacuum transfer as described in the general isolation protocol to yield 2-vinylpyrrolidine (4b) (0.051 g, 66%). A lower isolated yield compared to the observed conversion yield is mostly due to high volatility of the product, which resulted in loss of the product during solvent evaporation. $^1$H NMR (500 MHz, C$_6$D$_6$): δ/ppm 5.89-5.70 (m, 1H), 5.22-5.08 (m, 1H), 5.01-4.89 (m, 1H), 3.39-3.24 (m, 1H), 2.92-2.73 (m, 1H), 2.68-2.55 (m, 1H), 1.76-1.60 (m, 1H), 1.59-1.47 (m, 1H), 1.47-1.36 (m, 1H), 1.37-1.18 (m, 2H). $^{13}$C{$^1$H} NMR (126 MHz, C$_6$D$_6$): δ/ppm 142.48, 128.25, 128.06, 127.87, 113.32, 61.58, 46.71, 32.49, 25.51.

Example 7

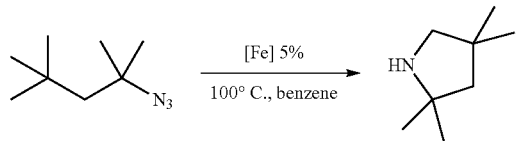

2,2,4,4-Tetramethylpyrrolidine (14b): The general procedure for the catalytic formation of N-heterocyclic amines was followed. Temperature and time of the reaction were 100° C. and 48 hours, respectively. Run 1: Reagents: 2,4,4-trimethyl-2-azidopentane (14a) (0.018 g, 0.13 mmol, 1 equiv) and [Fe] (0.0054 g, 0.05 equiv). Ferrocene (0.0152 g, 0.082 mmol) was added to the reaction mixture. The $^1$H NMR spectrum of the resulting solution showed that the ratio of the area under the ferrocene proton resonance and the protons of CH$_2$N group of 2,2,4,4-tetramethylpyrrolidine (14b) is 4.61 to 1.00, respectively. Calculated yield of 2,2,4,4-tetramethylpyrrolidine (14b) is 76%. Run 2: Reagents: 2,4,4-trimethyl-2-azidopentane (14a) (0.018 g, 0.13 mmol, 1 equiv) and [Fe] (0.0054 g, 0.05 equiv). Ferrocene (0.0161 g, 0.087 mmol) was added to the reaction mixture. The $^1$H NMR spectrum of the resulting solution showed that the ratio of the area under the ferrocene proton resonance and the protons of CH$_2$N group of 2,2,4,4-tetramethylpyrrolidine (14b) is 5.25 to 1.00, respectively. Calculated yield of 2,2,4,4-tetramethylpyrrolidine (14b) is 71%. Product isolation: Reagents: 2,4,4-trimethyl-2-azido pentane (14a) (0.040 g, 0.26 mmol, 1 equiv) and [Fe] (0.011 g, 0.05 equiv). Temperature and time of the reaction were 100° C. and 72 hours, respectively. The product was isolated via vacuum transfer as described in the general isolation protocol to yield 2,2,4,4-tetramethylpyrrolidine (14b) (0.019 g, 71%). A lower isolated yield compared to the observed conversion yield is mostly due to high volatility of the product, which resulted in loss of the product during solvent evaporation. Spectroscopic and physical characterization of 2,2,4,4-tetramethylpyrrolidine (14b) was previously reported. $^1$H NMR (500 MHz, $C_6D_6$): δ/ppm 2.61 (s, 2H), 1.30 (s, 2H), 1.29 (s, 1H), 1.11 (s, 6H), 0.96 (s, 6H). $^{13}C\{^1H\}$ NMR (126 MHz, $C_6D_6$): δ/ppm 60.29, 59.25, 54.57, 40.58, 30.39, 28.58.

Example 8

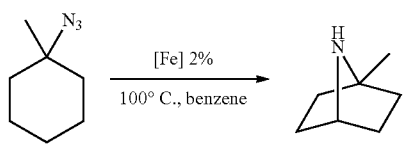

1-Methyl-7-azabicyclo[2.2.1]heptane (16b): The general procedure for the catalytic formation of N-heterocyclic amines was followed. Temperature and time of the reaction were 120° C. and 24 hours, respectively. Run 1: Reagents: 1-methyl-1-azidocyclohexane (16a) (0.022 g, 0.16 mmol, 1 equiv) and [Fe] (0.0029 g, 0.02 equiv). Ferrocene (0.011 g, 0.058 mmol) was added to the reaction mixture. The $^1$H NMR spectrum of the resulting solution showed that the ratio of the area under the ferrocene proton resonance and the CH group of 1-methyl-7-azabicyclo[2.2.1]heptane (16b) is 4.05 to 1.00, respectively. Calculated yield of 1-methyl-7-azabicyclo[2.2.1]heptane (16b) is 90%. Run 2: Reagents: 1-methyl-1-azidocyclohexane (16a) (0.041 g, 0.29 mmol, 1 equiv) and [Fe] (0.0053 g, 0.02 equiv). Temperature and time of the reaction were 100° C. and 36 hours, respectively. Ferrocene (0.011 g, 0.058 mmol) was added to the reaction mixture. The $^1$H NMR spectrum of the resulting solution showed that the ratio of the area under the ferrocene proton resonance and the CH group of 1-methyl-7-azabicyclo [2.2.1]heptane (16b) is 2.15 to 1.00, respectively. Calculated yield of 1-methyl-7-azabicyclo[2.2.1]heptane (16b) is 93%. Product isolation: Reagents: 1-methyl-1-azidocycloheptane (16a) (0.100 g, 0.72 mmol, 1 equiv) and [Fe] (0.013 g, 0.02 equiv). Temperature and time of the reaction were 100° C. and 36 hours, respectively. The product was isolated via vacuum transfer as described in the general isolation protocol to yield 1-methyl-7-azabicyclo[2.2.1]heptane (16b) (0.074 g, 92%). $^1$H NMR (500 MHz, $C_6D_6$): δ/ppm 3.36 (t, J=4.8 Hz, 1H, CHN), 1.58-1.46 (m, 2H, $CH_2$), 1.29 (s, 3H, $CH_3$), 1.28-1.20 (m, 4H, $CH_2$), 1.20-1.10 (m, 2H, $CH_2$). $^{13}C\{^1H\}$ NMR (126 MHz, $C_6D_6$): δ/ppm 63.16, 57.49, 37.13, 32.85, 21.28. HRMS (ESI$^+$) m/z Calc. 112.1121 $C_7H_{13}N+H^+$], Found 112.1118[M+H]$^+$.

Example 9

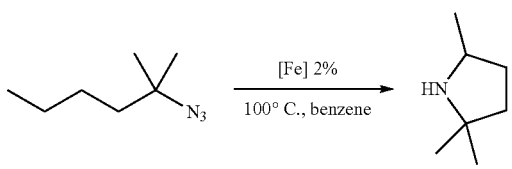

2,2,5-Trimethylpyrrolidine (12b): The general procedure for the catalytic formation of N-heterocyclic amines was followed. Run 1: Reagents: 2-methyl-2-azidohexane (12a) (0.020 g, 0.14 mmol, 1 equiv) and [Fe] (0.0026 g, 0.02 equiv). Temperature and time of the reaction were 100° C. and 72 hours, respectively. Ferrocene (0.018 g, 0.097 mmol) was added to the reaction mixture. The $^1$H NMR spectrum of the resulting solution showed that the ratio of the area under the ferrocene proton resonance and the protons of $CH(CH_3)$ group of 2,2,5-trimethylpyrrolidine (12b) is 7.1 to 1.00, respectively. Calculated yield of 2,2,5-trimethylpyrrolidine (12b) is 96%. Run 2: Reagents: 2-methyl-2-azidohexane (12a) (0.017 g, 0.12 mmol, 1 equiv) and [Fe] (0.0021 g, 0.02 equiv). Temperature and time of the reaction were 100° C. and 36 hours, respectively. Ferrocene (0.022 g, 0.12 mmol) was added to the reaction mixture. The $^1$H NMR spectrum of the resulting solution showed that the ratio of the area under the ferrocene proton resonance and the protons of $CH(CH_3)$ group of 2,2,5-trimethylpyrrolidine (12b) is 11.6 to 1.00, respectively. Calculated yield of 2,2,5-trimethylpyrrolidine (12b) is 85%. Product isolation: Reagents: 2-methyl-2-azidohexane (12a) (0.10 g, 0.70 mmol, 1 equiv) and [Fe] (0.013 g, 0.02 equiv). Temperature and time of the reaction were 100° C. and 36 hours, respectively. The product was isolated via vacuum transfer as described in the general isolation protocol to yield 2,2,5-trimethylpyrrolidine (12b) (0.073 g, 92%). Spectroscopic characterization of 2,2,5-trimethylpyrrolidine (12b) was previously reported. $^1$H NMR (500 MHz, $C_6D_6$): δ/ppm 5.89-5.70 (m, 1H), 5.22-5.08 (m, 1H), 5.01-4.89 (m, 1H), 3.39-3.24 (m, 1H), 2.92-2.73 (m, 1H), 2.68-2.55 (m, 1H), 1.76-1.60 (m, 1H), 1.59-1.47 (m, 1H), 1.47-1.36 (m, 1H), 1.37-1.18 (m, 2H). $^{13}C\{^1H\}$ NMR (126 MHz, $C_6D_6$): δ/ppm 142.48, 128.25, 128.06, 127.87, 113.32, 61.58, 46.71, 32.49, 25.51.

Example 10

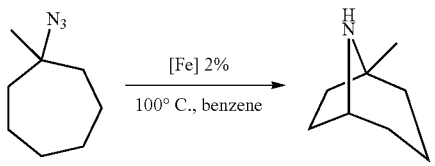

1-Methyl-8-azabicyclo[3.2.1]octane (17b): The general procedure for the catalytic formation of N-heterocyclic amines was followed. Temperature and time of the reaction were 100° C. and 36 hours, respectively. Run 1: Reagents: 1-methyl-1-azidocycloheptane (17a) (0.043 g, 0.28 mmol, 1 equiv) and [Fe] (0.0051 g, 0.02 equiv). Ferrocene (0.0119 g, 0.64 mmol) was added to the reaction mixture. The $^1$H NMR spectrum of the resulting solution showed that the ratio of the area under the ferrocene proton resonance and the CH protons of 1-methyl-8-azabicyclo[3.2.1]octane (17b) is 2.38 to 1.00, respectively. Calculated yield of 1-methyl-8-azabicyclo[3.2.1]octane (17b) is 96%. Run 2: 1-methyl-1-azidocycloheptane (17a) (0.046 g, 0.30 mmol, 1 equiv) and [Fe] (0.0060 g, 0.02 equiv). Ferrocene (0.0201 g, 1.08 mmol) was added to the reaction mixture. The $^1$H NMR spectrum of the resulting solution showed that the ratio of the area under the ferrocene proton resonance and the CH protons of 1-methyl-8-azabicyclo[3.2.1]octane (17b) is 3.87 to 1.00, respectively. Calculated yield of 1-methyl-8-azabicyclo[3.2.1]octane (17b) is 93%. Product isolation: Reagents: 1-methyl-1-azidocycloheptane (17a) (0.10 g, 0.65 mmol, 1 equiv.) and [Fe] (0.012 g, 0.02 equiv.). The product was isolated via vacuum transfer as described in the general isolation protocol to yield 1-methyl-8-azabicyclo[3.2.1]octane (17b) (0.074 g, 91%). $^1$H NMR (500 MHz, C$_6$D$_6$): δ/ppm 3.35-3.22 (m, 1H), 1.73-1.60 (m, 1H), 1.57-1.41 (m, 5H), 1.39-1.30 (m, 1H), 1.30-1.13 (m, 3H), 1.09 (s, 3H). $^{13}$C{$^1$H} NMR (126 MHz, C$_6$D$_6$): δ/ppm 59.48, 56.46, 39.57, 36.59, 32.52, 31.37, 27.87, 19.31. HRMS (ESI$^+$) m/z Calc. 126.1277[C$_8$H$_{15}$N+H$^+$], 126.1274 [M+H]$^+$. Crystallization: 1-methyl-8-azabicyclo[3.2.1]octane (17b) was reacted with an equimolar amount of L-(+)-tartaric acid in MeOH for 30 min at room temperature to give a colorless clear solution. The solvent was removed under vacuum and the resulting solid was washed with dichloromethane three times. Crystals suitable for diffraction analysis were obtained by slow evaporation of a MeOH solution of the tartrate salt of the amine. The solid-state molecular structure is shown in the crystallographic data and solid molecular structure section.

Example 11

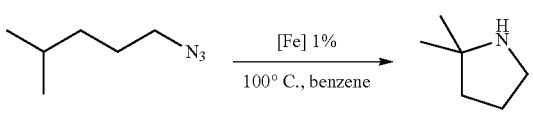

2,2-Dimethylpyrrolidine (9b): The general procedure for the catalytic formation of N-heterocyclic amines was followed. Temperature and time of the reaction were 100° C. and 12 hours, respectively. Run 1: Reagents: 1-azido-4-methylpentane (9a) (0.020 g, 0.16 mmol, 1 equiv) and [Fe] (0.0014 g, 0.01 equiv). Ferrocene (0.0080 g, 0.46 mmol) was added to the reaction mixture. The $^1$H NMR spectrum of the resulting solution showed that the ratio of the area under the ferrocene proton resonance and CH$_2$ protons of 2,2-dimethylpyrrolidine (9b) is 4.27 to 1.00, respectively. Calculated yield of 2,2-dimethylpyrrolidine (9b) is 34%. Run 2: Reagents: 1-azido-4-methylpentane (9a) (0.020 g, 0.16 mmol, 1 equiv). and [Fe] (0.0014 g, 0.01 equiv). Ferrocene (0.0093 g, 0.50 mmol) was added to the reaction mixture. The $^1$H NMR spectrum of the resulting solution showed that the ratio of the area under the ferrocene proton resonance and CH$_2$ protons of 2,2-dimethylpyrrolidine (9b) is 4.39 to 1.00, respectively. Calculated yield of 2,2-dimethylpyrrolidine (9b) is 36%. Product isolation: The product of the reaction was not isolated. The identity of the product was determined by comparing the NMR spectrum of the reaction mixture to the NMR spectrum of the product from the amination of 2-methyl-2-azidopentane (13b) that was fully characterized.

Example 12

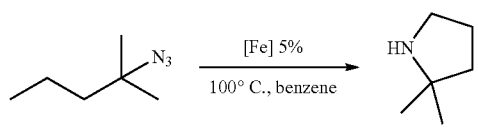

2,2-Dimethylpyrrolidine (13b): The general procedure for the catalytic formation of N-heterocyclic amines was followed. Run 1: Reagents: 2-methyl-2-azido-pentane (13a) (0.021 g, 0.17 mmol, 1 equiv) and [Fe] (0.0075 g, 0.05 equiv). Temperature and time of the reaction were 100° C. and 12 hours, respectively. Ferrocene (0.014 g, 0.075 mmol) was added to the reaction mixture. The $^1$H NMR spectrum of the resulting solution showed that the ratio of the area under the ferrocene proton resonance and the CH protons of N—CH$_2$ group of 2,2-dimethylpyrrolidine (13b) is 2.79 to 1.00, respectively. Calculated yield of 2,2-dimethylpyrrolidine (13b) is 82%. Run 2: Reagents: 2-methyl-2-azido-pentane (13a) (0.020 g, 0.16 mmol, 1 equiv) and [Fe] (0.0075 g, 0.05 equiv). Temperature and time of the reaction were 100° C. and 22 hours, respectively. Ferrocene (0.017 g, 0.091 mmol) was added to the reaction mixture. The $^1$H NMR spectrum of the resulting solution showed that the ratio of the area under the ferrocene proton resonance and the CH protons of N—CH$_2$ group of 2,2-dimethylpyrrolidine (13b) is 3.11 to 1.00, respectively. Calculated yield of 2,2-dimethylpyrrolidine (13b) is 91%. Product isolation: Reagents: 1-methyl-1-azidocycloheptane (13a) (0.100 g, 0.79 mmol, 1 equiv) and [Fe] (0.035 g, 0.05 equiv). Temperature and time of the reaction were 100° C. and 24 hours, respectively. The product was isolated via vacuum transfer as described in the general isolation protocol to yield 2,2-dimethylpyrrolidine (13b) (0.065 g, 83%). Spectroscopic characterization of 2,2-dimethyl pyrrolidine (13b) was previously reported. $^1$H NMR (500 MHz, C$_6$D$_6$): δ/ppm 2.82 (t, J=7.0 Hz, 2H), 1.64-1.50 (m, 2H), 1.37-1.27 (m, 2H), 1.05 (s, 6H). $^{13}$C{$^1$H} NMR (126 MHz, C$_6$D$_6$): δ/ppm 58.81, 46.45, 39.92, 29.10, 26.52.

Example 13

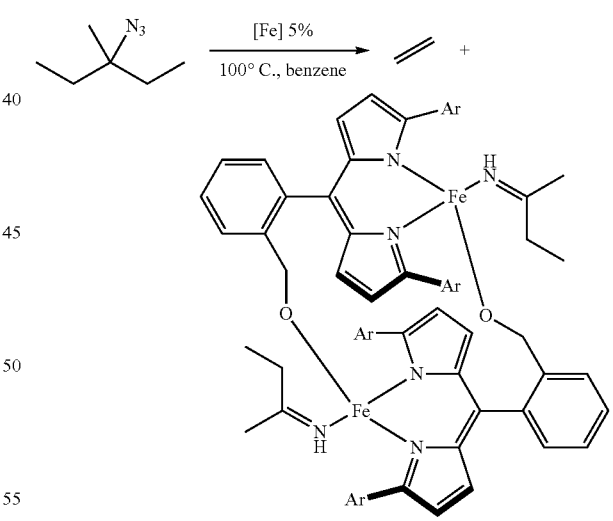

Catalytic cyclization of 3-methyl-3-azidopentane: The general procedure for the catalytic formation of N-heterocyclic amines was followed. Reagents: 3-methyl-3-azidopentane (0.02 g, 0.16 mmol, 1 equiv) and [Fe] (0.0071 g, 0.05 equiv). Temperature and time of the reaction were 100° C. and 26 hours, respectively. The formation of the desired N-heterocyclic amine was not observed during the course of the reaction. Instead, deactivation of the catalyst occurred via a radical disproportionation mechanism to give ethylene (observed by $^1$H NMR) and an iron(II) 2-butimine complex (characterized by X-ray diffraction) that precipitated out of the reaction mixture (0.0063 g, 80% based on [Fe]).

Example 14

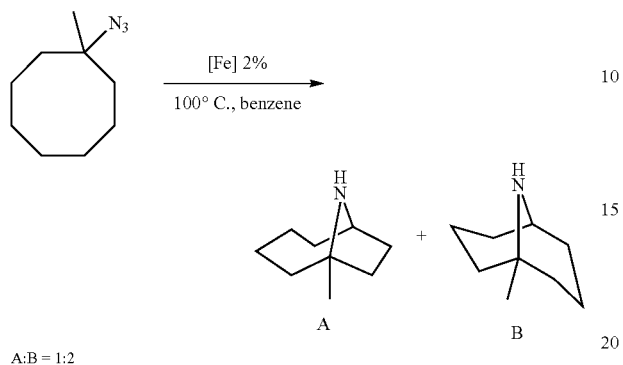

A:B = 1:2

1-Methyl-9-azabicyclo[4.2.1]nonane (20b) and 1-methyl-9-azabicyclo[3.3.1]nonane (20c): The general procedure for the catalytic formation of N-heterocyclic amines was followed. Temperature and time of the reaction were 120° C. and 24 hours, respectively. Run 1: Reagents: 1-methylazidocyclooctane (20a) (0.019 g, 0.11 mmol, 1 equiv) and [Fe] (0.0022 g, 0.02 equiv). Ferrocene (0.022 g, 0.12 mmol) was added to the reaction mixture. The $^1$H NMR spectrum of the resulting solution showed that the ratio of the area under the ferrocene proton resonance and the resonances of CH group of 1-methyl-9-azabicyclo[4.2.1]nonane (20b) and 1-methyl-9-azabicyclo[3.3.1]nonane (20c) is 40.1 to 2.22 and 1.00, respectively. Calculated yield of 1-methyl-9-azabicyclo[4.2.1]nonane (20b) and 1-methyl-9-azabicyclo[3.3.1]nonane (20c) was calculated to be 57% and 26%, respectively. Run 2: Reagents: 1-methylazidocyclooctane (13a) (0.050 g, 0.31 mmol, 1 equiv) and [Fe] (0.0055 g, 0.02 equiv). Ferrocene (0.0144 g, 0.077 mmol) was added to the reaction mixture. The $^1$H NMR spectrum of the resulting solution showed that the ratio of the area under the ferrocene proton resonance and the resonances of CH group of 1-methyl-9-azabicyclo[4.2.1]nonane (20b) and 1-methyl-9-azabicyclo[3.3.1]nonane (20c) is 9.859 to 2.00 and 1.00, respectively. The yield of 1-methyl-9-azabicyclo[4.2.1]nonane (20b) and 1-methyl-9-azabicyclo[3.3.1]nonane (20c) was calculated to be 54% and 27%, respectively. Product isolation: Reagents: 1-methylazidocyclooctane (13a) (0.50 g, 0.30 mmol, 1 equiv) and [Fe] (0.054 g, 0.02 equiv). The mixture of 1-methyl-9-azabicyclo[3.3.1]nonane (20c) and 1-methyl-9-azabicyclo[4.2.1]nonane (20b) was isolated via vacuum transfer as described in the general isolation protocol (0.33 g, 80%). 1-methyl-9-azabicyclo[4.2.1]nonane (20b)$^1$H NMR (500 MHz, C$_6$D$_6$): δ/ppm 3.48-3.38 (m, 1H), 2.12-1.25 (m, 12H), 1.12 (s, 3H). 1-methyl-9-azabicyclo[3.3.1]nonane (20c)$^1$H NMR (500 MHz, C$_6$D$_6$): δ/ppm 3.08-2.98 (m, 1H), 2.12-1.25 (m, 12H), 0.93 (s, 3H). HRMS (ESI$^+$) m/z Calc. 140.1434 [C$_9$H$_{17}$N+H$^+$], Found 140.1431 [M+H]$^+$. Crystallization: The mixture was added to a solution of L-(+)-tartaric acid (0.4 g, 2.7 mmol) in 3 mL of MeOH. The solvent was evaporated and the resulting solid was washed with dichloromethane (5×2 mL) and dried under high vacuum. Slow evaporation of MeOH resulted in formation of crystals suitable for X-ray diffraction analysis. Unfortunately, we were not able to separate 1-methyl-9-azabicyclo[3.3.1]nonane (20c) and 1-methyl-9-azabicyclo[4.2.1]nonane (20b) via recrystallization as was evident by both $^1$H NMR and X-ray diffraction. The crystal contained both heterocycles. The disorder model suggests that the symmetrical heterocycle, 1-methyl-9-azabicyclo[3.3.1]nonane (20c) is the minor species in the crystal. 1-methyl-9-azabicyclo[4.2.1]nonane (20b)$^1$H NMR (500 MHz, methanol-d4): δ/ppm 4.42 (s, 2H), 4.17-4.03 (m, 1H), 2.4-1.69 (m, 12H), 1.52 (s, 3H). 1-methyl-9-azabicyclo[3.3.1]nonane (20c)$^1$H NMR (500 MHz, methanol-d4): δ/ppm 4.42 (s, 2H) 3.69 (s, br, 1H), 2.4-1.69 (m, 12H), 1.32 (s, 3H). The solid-state molecular structure is shown in the crystallographic data and solid molecular structure section.

Example 15

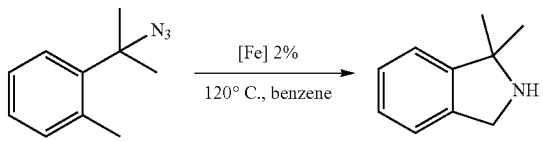

1,1-Dimethylisoindoline (23b): The general procedure for the catalytic formation of N-heterocyclic amines was followed. Temperature and time of the reaction were 120° C. and 48 hours, respectively. Run 1: Reagents: 1-(2-azidopropan-2-yl)-2-methylbenzene (23a) (0.045 g, 0.26 mmol, 1 equiv) and [Fe] (0.0047 g, 0.02 equiv). 1,3,5-trimethoxybenzene (0.0279 g, 0.17 mmol) was added to the reaction mixture. The $^1$H NMR spectrum of the resulting solution showed that the ratio of the area under CH$_3$ resonances of methoxy groups of trimethoxybenzene and the CH$_2$ group of 1,1-dimethylisoindoline (23b) is 5.10 to 1.00, respectively. Calculated yield of 1,1-dimethylisoindoline (23b) is 57%. Run 2: The general procedure for the catalytic formation of N-heterocyclic amines was followed. Reagents: 1-(2-azidopropan-2-yl)-2-methylbenzene (23a) (0.045 g, 0.26 mmol, 1 equiv) and [Fe] (0.0047 g, 0.02 equiv). 1,3,5-trimethoxybenzene (0.0200 g, 0.12 mmol) was added to the reaction mixture. The $^1$H NMR spectrum of the resulting solution showed that the ratio of the area under CH$_3$ resonances of the methoxy groups of trimethoxybenzene and the CH$_2$ group of 1,1-dimethylisoindoline (23b) is 4.18 to 1.00, respectively. Calculated yield of 1,1-dimethylisoindoline (23b) is 50%. Product isolation: Reagents: 1-(2-azidopropan-2-yl)-2-methylbenzene (23a) (0.05 g, 0.28 mmol, 1 equiv) and [Fe] (0.0052 g, 0.02 equiv). The product was separated from the catalyst via vacuum transfer as described in the general isolation protocol and was contaminated with 10% of an unidentified byproduct. Attempts to isolate clean material using column chromatography and distillation did not give satisfactory results. $^1$H NMR (500 MHz, C$_6$D$_6$): δ/ppm 7.08-7.03 (m, 2H), 7.02-6.96 (m, 1H), 6.96-6.91 (m, 1H), 3.95 (s, 2H), 1.27 (s, 6H). HRMS (ESI$^+$) m/z Calc. 148.1121 [C$_{10}$H$_{13}$N+H$^+$], Found 148.1128 [M+H]$^+$.

Example 16

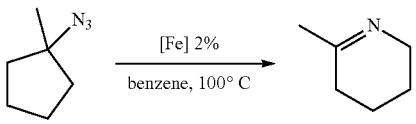

6-Methyl-2,3,4,5-tetrahydropyridine (21b): The general procedure for the catalytic formation of N-heterocyclic amines was followed. Temperature and time of the reaction were 120° C. and 24 hours, respectively. Run 1: Reagents: 1-methylazidocyclopentane (21a) (0.045 g, 0.36 mmol, 1 equiv) and [Fe] (0.0065 g, 0.02 equiv). Ferrocene (0.014 g, 0.074 mmol) was added to the reaction mixture. The $^1$H NMR spectrum of the resulting solution showed that the ratio of the area under the ferrocene proton resonance and the $CH_2$ group of 6-methyl-2,3,4,5-tetrahydropyridine (21b) is 1.13 to 1.00, respectively. Calculated yield of 6-methyl-2,3,4,5-tetrahydropyridine (21b) is 92%. Run 2: Reagents: 1-methylazidocyclopentane (21a) (0.043 g, 0.34 mmol, 1 equiv) and [Fe] (0.0063 g, 0.02 equiv). Ferrocene (0.0126 g, 0.067 mmol) was added to the reaction mixture. The $^1$H NMR spectrum of the resulting solution showed that the ratio of the area under the ferrocene proton resonance and the $CH_2$ group of 6-methyl-2,3,4,5-tetrahydropyridine (21b) is 1.08 to 1.00, respectively. Calculated yield of 6-methyl-2,3,4,5-tetrahydropyridine (21b) is 91%. Product isolation: Reagents: 1-methyl-azidocyclopentane (21a) (0.100 g, 0.80 mmol, 1 equiv) and [Fe] (0.015 g, 0.02 equiv). Temperature and time of the reaction were 120° C. and 48 hours, respectively. The product was isolated via vacuum transfer as described in the general isolation protocol to yield 6-methyl-2,3,4,5-tetrahydropyridine (21b) (0.068 g, 88%). Spectroscopic characterization of 6-methyl-2,3,4,5-tetrahydropyridine (21b) was previously reported. The product readily decomposes to a corresponding amino-aldehyde via hydrolysis. $^1$H NMR (500 MHz, $C_6D_6$): δ/ppm 3.66-3.41 (m, 2H), 1.78 (s, 3H), 1.68-1.54 (m, 2H), 1.34-1.13 (m, 4H). $^{13}C\{^1H\}$ NMR (126 MHz, $C_6D_6$): δ/ppm 165.59, 49.45, 29.98, 27.48, 22.13, 20.07.

Example 17

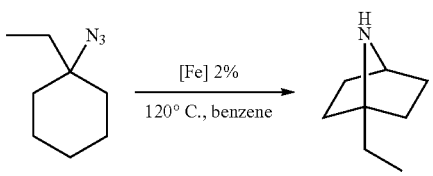

1-Ethyl-7-azabicyclo[2.2.1]heptane (18b): The general procedure for the catalytic formation of N-heterocyclic amines was followed. Temperature and time of the reaction were 120° C. and 48 hours, respectively. Run 1: Reagents: 1-ethylazidocyclohexane (18a) (0.019 g, 0.12 mmol, 1 equiv) and [Fe] (0.0023 g, 0.02 equiv). Ferrocene (0.0145 g, 0.078 mmol) was added to the reaction mixture. The $^1$H NMR spectrum of the resulting solution showed that the ratio of the area under the ferrocene proton resonance and the CH group of 1-ethyl-7-azabicyclo[2.2.1]heptane (18b) is 6.78 to 1.00, respectively. Calculated yield of 1-ethyl-7-azabicyclo[2.2.1]heptane (18b) is 93%. Run 2: Reagents: 1-ethylazidocyclohexane (18a) (0.045 g, 0.30 mmol, 1 equiv) and [Fe] (0.0054 g, 0.02 equiv). Ferrocene (0.0114 g, 0.061 mmol) was added to the reaction mixture. The $^1$H NMR spectrum of the resulting solution showed that the ratio of the area under the ferrocene proton resonance and the CH group of 1-ethyl-7-azabicyclo[2.2.1]heptane (18b) is 2.43 to 1.00, respectively. Calculated yield of 1-ethyl-7-azabicyclo[2.2.1]heptane (18b) is 96%. Product isolation: Reagents: 1-ethylazidocyclohexane (18a) (0.050 g, 0.33 mmol, 1 equiv) and [Fe] (0.0060 g, 0.02 equiv). The product was isolated via vacuum transfer as described in the general isolation protocol to yield 1-ethyl-7-azabicyclo[2.2.1]heptane (18b) (0.037 g, 92%). $^1$H NMR (500 MHz, $C_6D_6$): δ/ppm 3.34 (t, J=4.8 Hz, 1H), 1.65 (q, J=7.6 Hz, 2H), 1.58-1.38 (m, 2H), 1.31-1.09 (m, 8H), 0.90 (t, J=7.6 Hz, 3H). $^{13}C\{^1H\}$ NMR (126 MHz, $C_6D_6$): δ/ppm 67.12, 56.95, 34.48, 32.33, 28.70, 10.34. HRMS (ESI$^+$) m/z Calc. 126.12827 [$C_8H_{15}$N+H$^+$], Found 126.1276 [M+H]$^+$.

Example 18

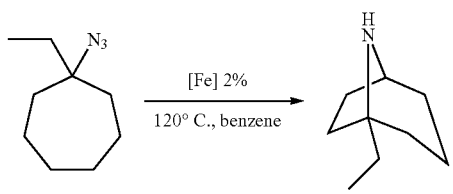

1-Ethyl-8-azabicyclo[3.2.1]octane (19b): The general procedure for the catalytic formation of N-heterocyclic amines was followed. Temperature and time of the reaction were 120° C. and 48 hours, respectively. Run 1: Reagents: 1-ethylazidocycloheptane (19a) (0.050 g, 0.30 mmol, 1 equiv) and [Fe] (0.0055 g, 0.02 equiv). Ferrocene (0.0151 g, 0.081 mmol) was added to the reaction mixture. The $^1$H NMR spectrum of the resulting solution showed that the ratio of the area under the ferrocene proton resonance and the CH group of 1-ethyl-8-azabicyclo[3.2.1]octane (19b) is 3.31 to 1.00, respectively. Calculated yield of 1-ethyl-8-azabicyclo[3.2.1]octane (19b) is 82%. Run 2: Reagents: 1-ethylazidocycloheptane (19a) (0.045 g, 0.27 mmol, 1 equiv) and [Fe] (0.0050 g, 0.02 equiv). Ferrocene (0.0179 g, 0.096 mmol) was added to the reaction mixture. The $^1$H NMR spectrum of the resulting solution showed that the ratio of the area under the ferrocene proton resonance and the CH group of 1-ethyl-8-azabicyclo[3.2.1]octane (19b) is 4.81 to 1.00, respectively. Calculated yield of 1-ethyl-8-azabicyclo[3.2.1]octane (19b) is 74%. Product isolation: Reagents: 1-ethylazidocycloheptane (19a) (0.050 g, 0.30 mmol, 1 equiv) and [Fe] (0.0054 g, 0.02 equiv). The product was separated from the catalytic mixture via vacuum transfer as described in the general isolation protocol. 1-ethyl-8-azabicyclo[3.2.1]octane (19b) was contaminated with <5% of unidentified byproduct. Attempts to isolate clean material using column chromatography and distillation did not give satisfactory results. $^1$H NMR (500 MHz, $C_6D_6$): δ/ppm 3.31 (m, 1H), 1.75-1.57 (m, 1H), 1.57-1.39 (m, 6H), 1.39-1.17 (m, 5H), 0.87 (t, J=7.6 Hz, 3H). $^{13}C\{^1H\}$ NMR (126 MHz, $C_6D_6$): δ/ppm 62.58, 56.14, 36.69, 34.27, 34.15, 33.01, 30.73, 19.13, 9.18. HRMS (ESI$^+$) m/z Calc. 140.1434 [$C_9H_{14}$N+H$^+$], Found 140.1438 [M+H]$^+$.

Example 19

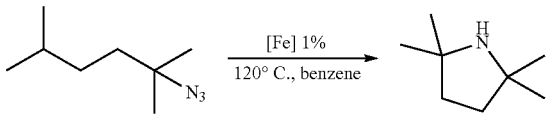

2,2,5,5-Tetramethylpyrrolidine (10b): The general procedure for the catalytic formation of N-heterocyclic amines was followed. Temperature and time of the reaction were 120° C. and 24 hours, respectively. Run 1: Reagents: 2,4-dimethyl-2-azidohexane (10a) (0.05 g, 0.3 mmol, 1 equiv) and [Fe] (0.0029 g, 0.01 equiv). Ferrocene (0.0124 g, 0.067 mmol) was added to the reaction mixture. The $^1$H NMR spectrum of the resulting solution showed that the ratio of the area under the ferrocene proton resonance and the CH$_2$ group of 2,2,5,5-tetramethylpyrrolidine (10b) is 0.527 to 1.00, respectively. Calculated yield of 2,2,5,5-tetramethylpyrrolidine (10b) is 98%. Run 2: Reagents: 2,4-dimethyl-2-azidohexane (10a) (0.017 g, 0.1 mmol, 1 equiv) and [Fe] (0.001 g, 0.01 equiv). Ferrocene (0.0107 g, 0.057 mmol) was added to the reaction mixture. The $^1$H NMR spectrum of the resulting solution showed that the ratio of the area under the ferrocene proton resonance and the CH$_2$ group of 2,2,5,5-tetramethylpyrrolidine (10b) is 1.39 to 1.00, respectively. Calculated yield of 2,2,5,5-tetramethylpyrrolidine (10b) is 95%. Product isolation: 2,4-dimethyl-2-azidohexane (10a) (0.05 g, 0.3 mmol, 1 equiv) and [Fe] (0.0029 g, 0.01 equiv). Temperature and time of the reaction were 120° C. and 24 hours, respectively. The product was isolated via vacuum transfer as described in the general isolation protocol to yield 2,2,5,5-tetramethylpyrrolidine (10b) (0.036 g, 92%). $^1$H NMR (500 MHz, C$_6$D$_6$): δ/ppm 3.34 (t, J=4.8 Hz, 1H), 1.65 (q, J=7.6 Hz, 2H), 1.58-1.38 (m, 2H), 1.31-1.09 (m, 8H), 0.90 (t, J=7.6 Hz, 3H).

Example 20

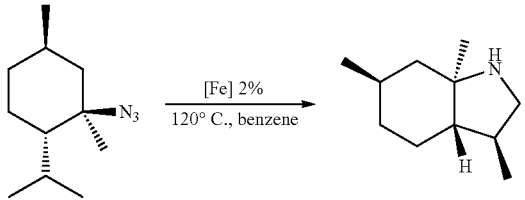

(3S,3aS,6R,7aR)-3,6,7a-Trimethyloctahydro-1H-indole (24b): The general procedure for the catalytic formation of N-heterocyclic amines was followed. Temperature and time of the reaction were 120° C. and 48 hours, respectively. Run 1: Reagents: (1R,2S,5R)-1-azido-2-isopropyl-1,5-dimethylcyclohexane (24a) (0.01 g, 0.05 mmol, 1 equiv) and [Fe] (0.001 g, 0.02 equiv). Ferrocene (0.0102 g, 0.055 mmol) was added to the reaction mixture. The $^1$H NMR spectrum of the resulting solution showed that the ratio of the area under the ferrocene proton resonance and the NCH group and CH group of (3S,3aS,6R,7aR)-3,6,7a-trimethyloctahydro-1Hindole (24b) is 12.58 to 1.00, respectively. The yield of (3S,3aS,6R,7aR)-3,6,7a-trimethyloctahydro-1H-indole (24b) was calculated to be 85%. Product isolation: Reagents: (1R,2S,5R)-1-azido-2-isopropyl-1,5-dimethylcyclohexane (24a) (0.1 g, 0.51 mmol, 1 equiv) and [Fe] (0.0093 g, 0.02 equiv). The product was isolated via vacuum transfer as described in the general isolation protocol to give (3S,3aS, 6R,7aR)-3,6,7a-trimethyloctahydro-1H-indole (24b) as a colorless oil in 77%, 0.066 g yield. $^1$H NMR (400 MHz, C$_6$D$_6$): δ/ppm 3.15 (dd, J=10.9, 9.1 Hz, 1H), 2.41 (dd, J=10.9, 9.1 Hz, 1H), 1.77-1.68 (m, 1H), 1.66-1.49 (m, 4H), 0.98-0.94 (m, 2H), 0.90 (d, J=6.5 Hz, 3H), 0.87 (d, J=6.4 Hz, 3H), 0.83 (s, 3H), 0.80-0.76 (m, 2H). Crystallization: The product was further purified by formation of a salt with L-(+)-tartaric acid to give indole L-tartrate in 63%, 0.102 g yield. (3S,3aS,6R,7aR)-3,6,7a-trimethyloctahydro-1H-indole L-tartrate (24b)$^1$H NMR (400 MHz, methanol-d4): δ/ppm 4.40 (s, 2H), 3.62 (dd, J=12.3, 9.5 Hz, 1H), 2.87 (dd, J=12.3, 7.8 Hz, 1H), 2.21-2.06 (m, 1H), 2.06-1.95 (m, 1H), 1.93-1.66 (m, 4H), 1.37-1.27 (m, 2H), 1.23 (s, 3H), 1.11 (d, J=6.5 Hz, 3H), 0.99 (d, J=6.7 Hz, 3H), 1.05-0.86 (m, 1H). $^{13}$C{$^1$H} NMR (126 MHz, methanol-d4): δ/ppm 176.93, 74.16, 67.55, 54.71, 50.77, 45.34, 35.36, 34.33, 29.92, 24.01, 22.41, 16.80, 16.65. HRMS (ESI$^+$) m/z Calc. 168.1747 [C$_{11}$H$_{21}$N+H$^+$], Found 168.1750 [M+H]$^+$. Crystals suitable for diffraction analysis were obtained by slow evaporation of a MeOH solution of the tartrate salt of the amine. The solid-state molecular structure is shown in the crystallographic data and solid molecular structure section.

Example 21

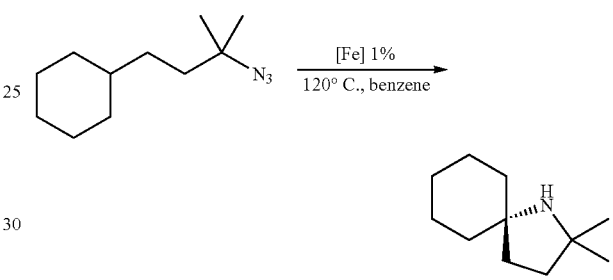

2,2-Dimethyl-1-azaspiro[4.5]decane (22b): The general procedure for the catalytic formation of N-heterocyclic amines was followed. Temperature and time of the reaction were 120° C. and 36 hours, respectively. Run 1: Reagents: 2-methyl-2-azido-4-cyclohexyl butane (22a) (0.022 g, 0.11 mmol, 1 equiv) and [Fe] (0.0010 g, 0.01 equiv). Ferrocene (0.0103 g, 0.055 mmol) was added to the reaction mixture. The $^1$H NMR spectrum of the resulting solution showed that the ratio of the area under the ferrocene proton resonance and the CH$_3$ group of 2,2-dimethyl-1-azaspiro[4.5]decane (22b) is 0.863 to 1.00 respectively. The yield of 2,2-dimethyl-1-azaspiro[4.5]decane (22b) was calculated to be 95%. Run 2: Reagents: 2-methyl-2-azido-4-cyclohexyl butane (22a) (0.020 g, 0.10 mmol, 1 equiv) and [Fe] (0.0009 g, 0.01 equiv). Ferrocene (0.0183 g, 0.10 mmol) was added to the reaction mixture. The $^1$H NMR spectrum of the resulting solution showed that the ratio of the area under the ferrocene proton resonance and the CH$_3$ group of 2,2-dimethyl-1-azaspiro[4.5]decane (22b) is 1.73 to 1.00 respectively. The yield of 2,2-dimethyl-1-azaspiro[4.5]decane (22b) was calculated to be 93%. Product isolation: Reagents: 2-methyl-2-azido-4-cyclohexyl butane (22a) (0.050 g, 0.26 mmol, 1 equiv) and [Fe] (0.0023 g, 0.01 equiv). Temperature and time of the reaction were 120° C. and 36 hours, respectively. The product was isolated via vacuum transfer as described in the general isolation protocol to yield 2,2-dimethyl-1-azaspiro[4.5]decane (22b) (0.039 g, 90%). $^1$H NMR (500 MHz, C$_6$D$_6$): δ/ppm 1.61-1.50 (m, 6H), 1.42-1.27 (m, 8H), 1.12 (s, 6H). $^{13}$C{$^1$H} NMR (126 MHz, C$_6$D$_6$): δ/ppm 61.68, 58.32, 40.72, 39.16, 31.37, 31.34, 25.95, 23.92. HRMS (ESI$^+$) in& Calc. 168.1752 [C$_{11}$H$_{21}$N+H$^+$], Found 168.1749 [M+H]$^+$.

Example 22

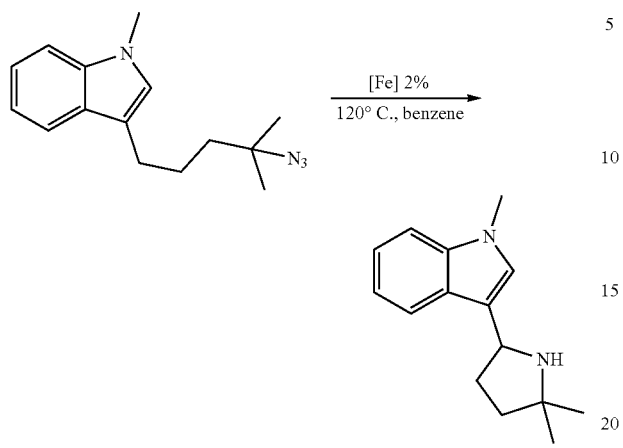

3-(5,5-Dimethylpyrrolidin-2-yl)-1-methyl-1H-indole (11b): The general procedure for the catalytic formation of N-heterocyclic amines was followed. Run 1: Reagents: 3-(4-azido-4-methylpentyl)-1-methyl-1H-indole (11a) (0.015 g, 0.058 mmol, 1 equiv) and [Fe] (0.0011 g, 0.02 equiv). Temperature and time of the reaction were 120° C. and 24 hours, respectively. Ferrocene (0.0077 g, 0.041 mmol) was added to the reaction mixture. The $^1$H NMR spectrum of the resulting solution showed that the ratio of the area under the ferrocene proton resonance and the CH group of 3-(5,5-dimethylpyrrolidin-2-yl)-1-methyl-1H-indole (11b) is 8.17 to 1.00, respectively. The yield of 3-(5,5-dimethylpyrrolidin-2-yl)-1-methyl-1H-indole (11b) was calculated to be 87%. Run 2: Reagents: 3-(4-azido-4-methylpentyl)-1-methyl-1H-indole (11a) (0.016 g, 0.062 mmol, 1 equiv) and [Fe] (0.0011 g, 0.02 equiv). Temperature and time of the reaction were 120° C. and 36 hours, respectively. Ferrocene (0.0087 g, 0.047 mmol) was added to the reaction mixture. The $^1$H NMR spectrum of the resulting solution showed that the ratio of the area under the ferrocene proton resonance and the CH group of 3-(5,5-dimethylpyrrolidin-2-yl)-1-methyl-1H-indole (11b) is 7.99 to 1.00 respectively. The yield of 3-(5,5-dimethylpyrrolidin-2-yl)-1-methyl-1H-indole (11b) was calculated to be 94%. Product isolation: Reagents: 3-(4-azido-4-methylpentyl)-1-methyl-1H-indole (11a) (0.030 g, 0.12 mmol, 1 equiv) and [Fe] (0.0021 g, 0.02 equiv). Temperature and time of the reaction were 120° C. and 36 hours, respectively. The product was isolated via vacuum transfer as described in the general isolation protocol to yield 3-(4-azido-4-methylpentyl)-1-methyl-1H-indole (11b) (0.022 g, 84%). $^1$H NMR (500 MHz, C$_6$D$_6$): δ/ppm 7.97 (d, J=7.8 Hz, 1H), 7.34-7.26 (m, 1H), 7.27-7.21 (m, 1H), 7.07 (d, J=7.8 Hz, 1H), 6.75 (s, 1H), 4.69-4.52 (m, 1H), 3.00 (s, 3H), 2.30-2.17 (m, 1H), 2.03-1.88 (m, 1H), 1.76-1.64 (m, 1H), 1.64-1.53 (m, 1H), 1.24 (s, 3H), 1.18 (s, 3H). $^{13}$C{$^1$H} NMR (126 MHz, C$_6$D$_6$): δ/ppm 138.14, 125.51, 125.48, 121.86, 120.59, 119.93, 119.13, 109.48, 58.62, 55.44, 40.27, 34.43, 31.91, 31.10, 29.75, 29.71. HRMS (ESI$^+$) m/z Calc. 229.1699 [C$_{15}$H$_{20}$N$_2$+H$^+$], Found 229.1700 [M+H]$^+$.

Example 23

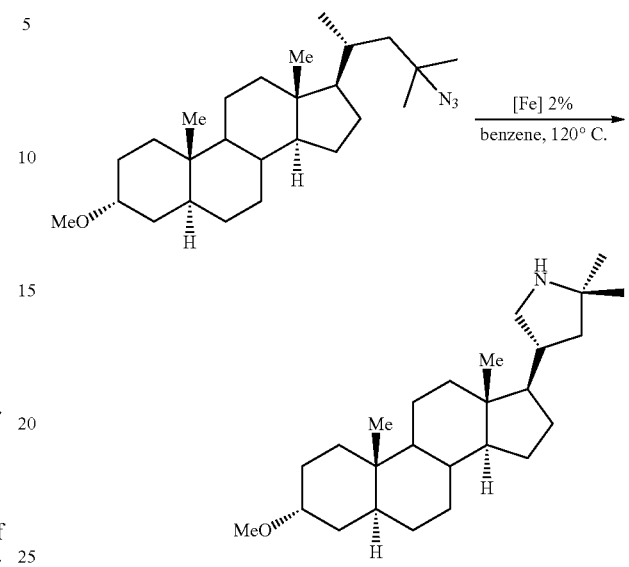

(4R)-4-((3R,5S,10S,13S,14S,17R)-3-Methoxy-10,13-dimethylhexadecahydro-1H-cyclopenta[a]phenanthren-17-yl)-2,2-dimethylpyrrolidine (25b): The general procedure for the catalytic formation of N-heterocyclic amines was followed. Product isolation: Reagents: (3R,5R,8R,9S,10S,13R,14S,17R)-17-((R)-4-azido-4-methylpentan-2-yl)-3-methoxy-10,13-dimethylhexadecahydro-1H-cyclopenta-[α]phenanthrene (25a) (0.10 g, 0.24 mmol, 1 equiv) and [Fe] (0.06 g, 0.02 equiv). Temperature and time of the reaction were 120° C. and 36 hours, respectively. The solvent was removed under vacuum to give a red solid, which was re-dissolved in 0.3 mL of MeOH/DCM solvent mixture (5% MeOH) and subjected to silica column chromatography (Re product=0.2, streaking spot). (4R)-4-((3R,5S,10S,13S,14S,17R)-3-methoxy-10,13-dimethylhexadecahydro-1H-cyclopenta[α]phenan-thren-17-yl)-2,2-dimethylpyrrolidine (25b) (0.068 g, 73%) was isolated as a white solid after removal of the solvent. $^1$H NMR (500 MHz, C$_6$D$_6$): δ/ppm 3.25 (s, 3H), 3.10 (m, 1H), 3.09-3.00 (m, 1H), 2.70-2.52 (m, 1H), 2.06-1.90 (m, 1H), 1.89-1.71 (m, 4H), 1.70-1.59 (m, 4H), 1.58-1.46 (m, 1H), 1.43-1.32 (m, 5H), 1.31-1.21 (m, 4H), 1.19 (s, 3H), 1.13 (s, 3H), 1.15-0.97 (m, 7H), 0.90 (s, 3H), 0.86-0.76 (m, 2H), 0.59 (s, 3H). $^{13}$C{$^1$H} NMR (126 MHz, C$_6$D$_6$): δ/ppm 80.65, 57.58, 56.48, 55.86, 55.49, 52.26, 47.53, 43.84, 43.00, 42.46, 40.90, 39.40, 36.14, 35.82, 35.19, 33.39, 30.92, 30.66, 28.61, 27.76, 27.41, 26.82, 24.87, 23.78, 21.02, 13.07. HRMS (ESI$^+$) m/z Calc. 388.3574 [C$_{26}$H$_{45}$NO+H$^+$], Found 388.3576 [M+H]$^+$.

Example 24

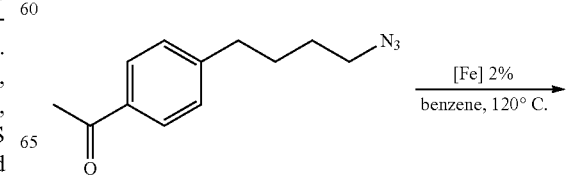

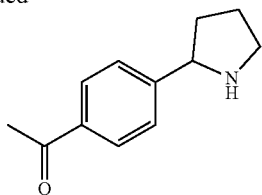

1-(4-(Pyrrolidin-2-yl)phenyl)ethenone (7b): The general procedure for the catalytic formation of N-heterocyclic amines was followed. Temperature and time of the reaction were 120° C. and 6 hours, respectively. Run 1: Reagents: 1-(4-(4-azidobutyl)phenyl)ethanone (7a) (0.013 g, 0.060 mmol, 1 equiv) and [Fe] (0.0011 g, 0.02 equiv). Ferrocene (0.0168 g, 0.090 mmol) was added to the reaction mixture. The $^1$H NMR spectrum of the resulting solution showed that the ratio of the area under the ferrocene proton resonance and the CH group of 1-(4-(pyrrolidin-2-yl)phenyl)ethanone (7b) is 18.5 to 1.00 respectively. The yield of 1-(4-(pyrrolidin-2-yl)phenyl)ethanone (7b) was calculated to be 82%. Run 2: Reagents: 1-(4-(4-azidobutyl)phenyl)ethanone (7a) (0.012 g, 0.052 mmol, 1 equiv.) and [Fe] (0.0010 g, 0.02 equiv.). Ferrocene (0.0149 g, 0.080 mmol) was added to the reaction mixture. The $^1$H NMR spectrum of the resulting solution showed that the ratio of the area under the ferrocene proton resonance and the CH group of 1-(4-(pyrrolidin-2-yl)phenyl)ethanone (7b) is 19.05 to 1.00, respectively. The yield of 1-(4-(pyrrolidin-2-yl)phenyl)ethanone (7b) was calculated to be 76%. Product isolation: Reagents: 1-(4-(4-azidobutyl)phenyl)ethenone (7a) (0.030 g, 0.12 mmol, 1 equiv) and [Fe] (0.0021 g, 0.02 equiv). Temperature and time of the reaction were 120° C. and 6 hours, respectively. The product was isolated by sublimation under high vacuum to yield 3-(4-azido-4-methylpentyl)-1-methyl-1H-indole (7b) (0.019 g, 73%). $^1$H NMR (500 MHz, C$_6$D$_6$): δ/ppm 7.70 (d, J=8.3 Hz, 2H), 7.17 (d, J=8.3 Hz, 2H), 3.60 (t, J=7.6 Hz, 1H), 2.84-2.69 (m, 1H), 2.55-2.40 (m, 1H), 1.99 (s, J=3.0 Hz, 3H), 1.76-1.56 (m, 1H), 1.52-1.37 (m, 1H), 1.37-1.13 (m, 2H). $^{13}$C{$^1$H} NMR (126 MHz, C$_6$D$_6$): δ/ppm 196.31, 151.48, 136.40, 128.67, 126.84, 62.15, 47.07, 35.18, 26.22, 25.68. HRMS (ESI$^+$) m/z Calc. 190.1226 [C$_{12}$H$_{15}$NO+H$^+$], Found 190.1225 [M+H]$^+$. Crystallization: The sublimed crystals of 1-(4-(pyrrolidin-2-yl)phenyl)ethanone (7b) were suitable for the diffraction analysis. The solid-state molecular structure is shown in the crystallographic data and solid molecular structure section.

Example 25

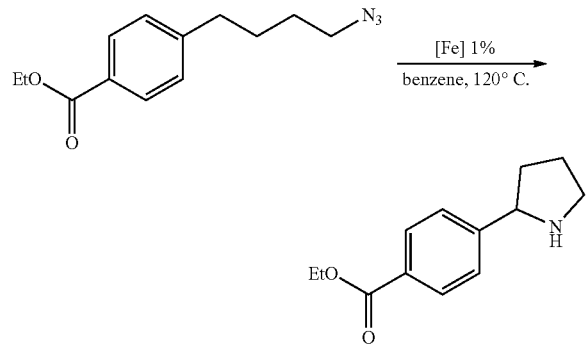

Ethyl 4-(pyrrolidin-2-yl)benzoate (8b): The general procedure for the catalytic formation of N-heterocyclic amines was followed. Temperature and time of the reaction were 120° C. and 12 hours, respectively. Run 1: Reagents: ethyl 4-(4-azidobutyl)benzoate (8a) (0.020 g, 0.081 mmol, 1 equiv) and [Fe] (0.0007 g, 0.01 equiv). Ferrocene (0.0134 g, 0.072 mmol) was added to the reaction mixture. The $^1$H NMR spectrum of the resulting solution showed that the ratio of the area under the ferrocene proton resonance and the CH group of ethyl 4-(pyrrolidin-2-yl)benzoate (8a) is 11.4 to 1.00 respectively. The yield of ethyl 4-(pyrrolidin-2-yl)benzoate (8b) was calculated to be 78%. Run 2: Reagents: ethyl 4-(4-azidobutyl)benzoate (8a) (0.020 g, 0.081 mmol, 1 equiv) and [Fe] (0.0007 g, 0.01 equiv). Ferrocene (0.0106 g, 0.057 mmol) was added to the reaction mixture. The $^1$H NMR spectrum of the resulting solution showed that the ratio of the area under the ferrocene proton resonance and the CH group of ethyl 4-(pyrrolidin-2-yl)benzoate (8b) is 8.30 to 1.00 respectively. The yield of ethyl 4-(pyrrolidin-2-yl)benzoate (8b) was calculated to be 85%. Product isolation: Reagents: ethyl 4-(4-azidobutyl)benzoate (8b) (0.030 g, 0.12 mmol, 1 equiv) and [Fe] (0.0011 g, 0.01 equiv). The product was isolated by sublimation under high vacuum to yield ethyl 4-(pyrrolidin-2-yl)benzoate (8b) (0.019 g, 71%). $^1$H NMR (500 MHz, C$_6$D$_6$): δ/ppm 8.24 (d, J=8.4 Hz, 2H), 7.35 (d, J=8.1 Hz, 2H), 4.16 (q, J=7.1 Hz, 2H), 3.74 (t, J=7.5 Hz, 1H), 2.95-2.84 (m, 1H), 2.68-2.56 (m, 1H), 1.87-1.73 (m, 1H), 1.64-1.49 (m, 1H), 1.49-1.29 (m, 2H), 1.03 (t, J=7.1 Hz, 3H). $^{13}$C{$^1$H} NMR (126 MHz, C$_6$D$_6$): δ/ppm 166.42, 151.54, 130.00, 126.83, 62.16, 60.70, 47.03, 35.15, 25.65, 14.36. HRMS (ESI$^+$) in& Calc. 220.1332 [C$_{13}$H$_{17}$NO$_2$+H$^+$], Found 220.1340 [M+H]$^+$.

Example 26

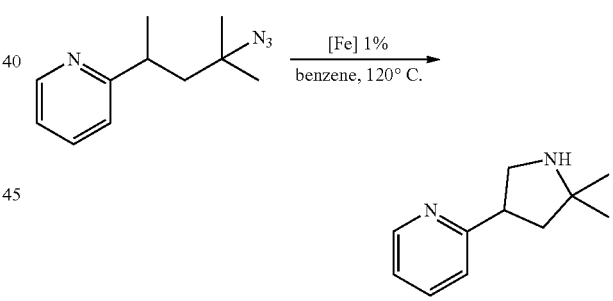

2-(5,5-Dimethylpyrrolidin-3-yl)pyridine (15b): The general procedure for the catalytic formation of N-heterocyclic amines was followed. Product isolation: Reagents: 2-(4-azido-4-methylpentan-2-yl)pyridine (15a) (0.020 g, 0.098 mmol, 1 equiv) and [Fe] (0.0009 g, 0.01 equiv). Temperature and time of the reaction were 120° C. and 48 hours, respectively. 2-(5,5-dimethylpyrrolidin-3-yl)pyridine (15b) was isolated by sublimation to give colorless crystals (Yield=82%, 0.014 g). $^1$H NMR (500 MHz, C$_6$D$_6$): δ/ppm 8.52-8.42 (m, 1H), 7.07-7.01 (m, 1H), 6.74 (d, J=8.6 Hz, 1H), 6.64-6.56 (m, 1H), 3.38-3.24 (m, 3H), 2.05-1.86 (m, 2H), 1.28 (s, 3H), 1.13 (s, 3H). $^{13}$C{$^1$H} NMR (126 MHz, C$_6$D$_6$): δ/ppm 165.03, 149.84, 135.72, 122.10, 121.00, 60.32, 54.17, 49.17, 47.93, 29.73, 29.24. HRMS (ESI$^+$) m/z Calc. 177.1386 [C$_{11}$H$_{16}$N$_2$+H$^+$], Found 177.13906 [M+H]$^+$. Crystallization: 2-(5,5-dimethylpyrrolidin-3-yl)pyridine (15b) was reacted with an equimolar amount of L-(+)- tartaric acid in MeOH for 30 min at room temperature to give a colorless clear solution. The solvent was removed under vacuum and the resulting solid was washed with dichloromethane three times. Crystals suitable for diffraction analysis were obtained by slow evaporation of a MeOH solution of the tartrate salt of the amine. The solid-state molecular structure is shown in the crystallographic data and solid molecular structure section.

Catalyst Recycling

Example 27

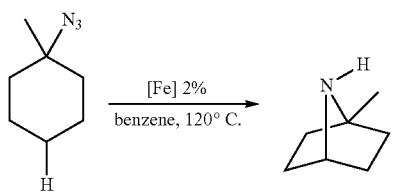

Catalyst recycling for subsequent amination reactions of 1-methyl-1-azidocyclohexane (16a): In a nitrogen-filled glovebox, 1-methyl-1-azidocyclohexane (16a) and [Fe] (0.0020 g, 0.01 equiv) were dissolved in 2 mL of benzene-d6. The reaction mixture was transferred into a J. Young tube and heated at 100° C. for 36 hours. The progression of the reaction was monitored by $^1$H NMR. The product was separated from the catalyst via vacuum transfer. Ferrocene was added to the isolated product in benzene-d6 and the yield was determined by $^1$H NMR. The catalyst was subjected to a new batch of substrate in benzene-d6 for the next cycle of amination (see Table 1).

TABLE 1

Summary of catalyst recycling experiments of 1-methyl-1-azidocyclohexane (16a).

| Experiment | m (substrate) [g] | m (Fc) [g] | Integration Ratio (Fc/substrate) | Yield (%) |
|---|---|---|---|---|
| 1.1 | 0.030 | 0.0180 | 0.48 | 92.2 |
| 1.2 | 0.030 | 0.0162 | 0.43 | 93.3 |
| 1.3 | 0.030 | 0.0139 | 0.38 | 91.9 |
| 1.4 | 0.030 | 0.0176 | 0.51 | 85.7 |
| 1.5 | 0.030 | 0.0091 | 1.11 | 20.5 |
| 2.1 | 0.030 | 0.0078 | 0.21 | 92.6 |
| 2.2 | 0.030 | 0.0089 | 0.24 | 90.8 |
| 2.3 | 0.030 | 0.0090 | 0.25 | 89.1 |
| 2.4 | 0.030 | 0.0100 | 0.29 | 85.4 |
| 3.1 | 0.030 | 0.0040 | 0.10 | 95.4 |
| 3.2 | 0.030 | 0.0070 | 0.19 | 91.2 |
| 3.3 | 0.030 | 0.0236 | 0.65 | 91.2 |
| 3.4 | 0.030 | 0.0110 | 0.37 | 73.4 |

Example 28

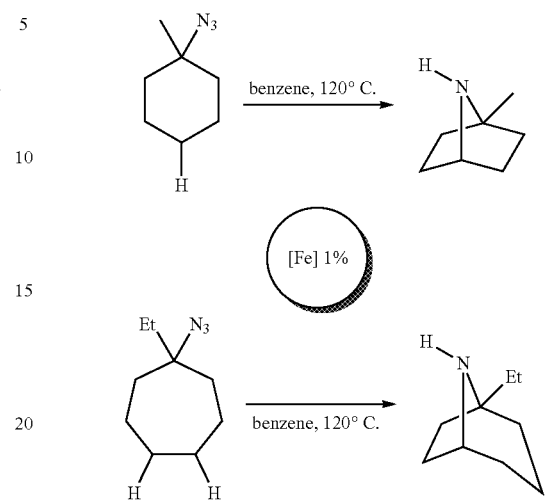

Catalyst recycling for the subsequent amination of 1-methyl-1-azidocyclohexane (16a) and 1-ethyl-1-azidocycloheptane (19a): In a nitrogen-filled glovebox, 1-methyl-1-azidocyclohexane (16a) and [Fe] (0.0020 g, 0.01 equiv) were dissolved in 2 mL of benzene-d6. The reaction mixture was transferred into a J. Young tube and heated at 120° C. for 36 hours. The progression of the reaction was monitored by $^1$H NMR. The product was separated from the catalyst via vacuum transfer. Ferrocene was added to the isolated product in benzene-d6 and the yield of the reaction was determined by NMR. The catalyst was subjected to 1-ethyl-1-azidocycloheptane (19a) in benzene-d6 for the next cycle of amination (see Table 2).

TABLE 2

Summary of catalyst recycling experiments of 1-methyl-1-azidocyclohexane (16a) and 1-ethyl-1-azidocycloheptane (19a).

| Experiment | m (substrate) [g] | m (Fc) [g] | NMR Integration Ratio (Fc/substrate) | Yield (%) |
|---|---|---|---|---|
| 4.1 | 0.03 | 0.008 | 0.22 | 92.7 |
| 4.2 | 0.03 | 0.017 | 0.56 | 89.8 |

Isolation of Intermediates

Example 29

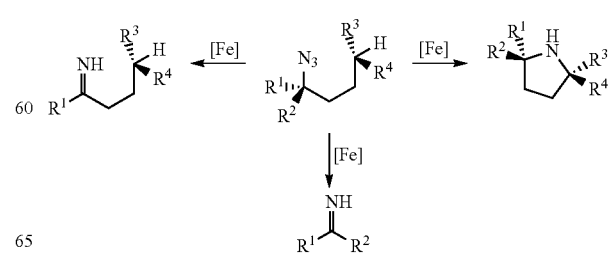

TABLE 3

Prediction of reaction outcome.

| Entry | Substituents at $C^4$-carbon ($R^3$; $R^4$) | Substituents at α-position ($R^1$; $R^2$) | Reaction outcome |
|---|---|---|---|
| 1 | Activated C—H bond $R^3$ or/and $R^4$ = Ar/vinyl groups | $R^1/R^2$ = any functionality | Productive annulation |
| 2 | Any C—H bond $R^3$; $R^4$ = any functionality | $R^1$ or/and $R^2 \neq H$ | Productive annulation |
| 3 | 1°, 2°, 3° C—H bond[a] $R^3$ or/and $R^4$ = alkyls | $R^1$ or/and $R^2$ = H | Imine formation (1,2-H shift) |
| 4 | No hydrogen at $C^4$ | $R^1$ and $R^2 \neq H$ | Imine formation (C—C bond cleavage) |

[a]Reaction with an azide containing a 3° C—H bond resulted in partial (35%) formation of the amine (see Table 7).

Imine formation as a result of a 1,2-H shift: The general catalytic conditions were applied to several azides containing a-hydrogen(s) and unactivated C—H bond(s) at $C^4$ (1-azidopentane, 2-azidopentane, azidocyclohexane). $^1$H NMR analysis of the reaction mixture showed no formation of the desired cyclic amine. The staring material, in most cases, was fully consumed and a mixture of unidentified products was observed, sharing common resonances in the 6-8 ppm region.

It was possible to crystallographically characterize a dimeric iron complex with the imine coordinated directly to the iron center, when 1-phenyl-1-azidobutane was reacted with the catalyst under the described conditions.

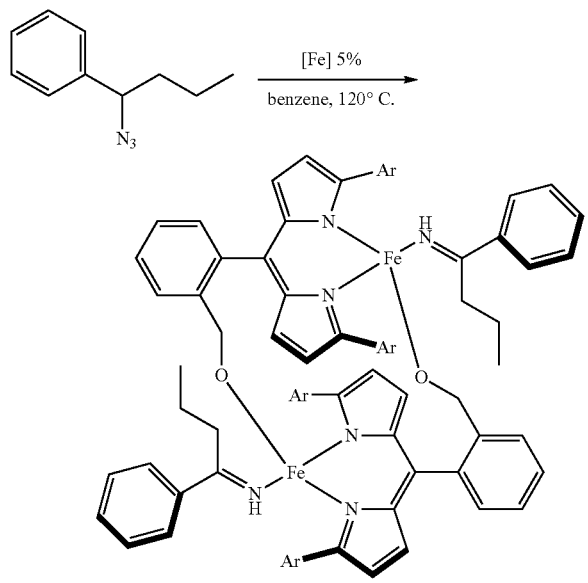

The general procedure for the catalytic reaction was followed. Reagents: 1-phenyl-1-azidobutane (0.03 g, 0.17 mmol, 1 equiv) and [Fe] (0.0031 g, 0.02 equiv). Temperature and time of the reaction were 120° C. and 12 hours, respectively. Crystals of the iron complex were obtained by slow cooling of the reaction mixture. The solid-state molecular structure of the dimeric iron complex is shown in the crystallographic data and solid molecular structure section.

Example 30

Imine formation as a result of a C—C bond cleavage: The catalytic amination of 2-methyl-2-azidopentane (13a) resulted in the formation of the desired pyrrolidine product (13b) in 83% isolated yield. The formation of crystals was observed upon cooling of the reaction mixture. Diffraction analysis revealed that the structure of the isolated compound consists of a dimeric iron complex coordinated by 2-propylimine.

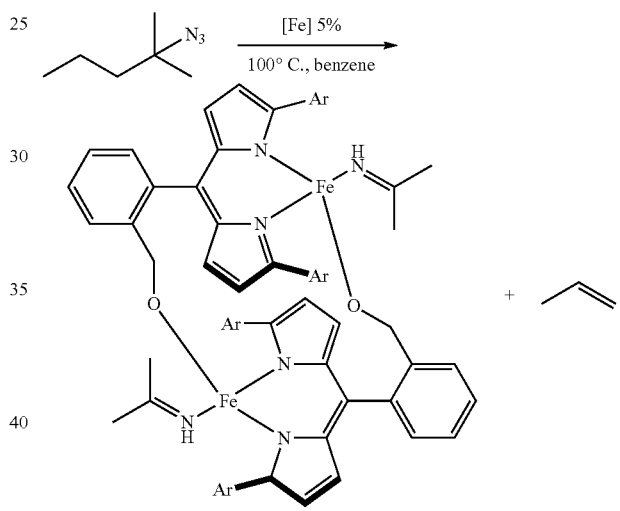

The general procedure for the catalytic formation of N-heterocyclic amines was followed. Reagents: 2-methyl-2-azido-pentane (13a) (0.040 g, 0.33 mmol, 1 equiv) and [Fe] (0.0150 g, 0.05 equiv). Temperature and time of the reaction were 100° C. and 12 hours, respectively. Crystals of the iron complex were obtained by slow cooling of the reaction mixture. The solid-state molecular structure of the dimeric iron complex is shown in the crystallographic data and solid molecular structure section. A high yield of the catalytic reaction suggests that imine formation is a significantly disfavored process compared to C—H bond amination. We hypothesize that coordination of the imine does not inhibit the catalysis. This assumption was independently verified by isolating the crystals from the reaction and re-subjecting them to catalytic conditions, observing comparable catalytic activity to the reactivity of the hexameric complex.

The imine formation most likely occurs as a result of a C—C bond breaking event, resulting in the formation of propene as a by-product if 2-methyl-2-azido-pentane (13a) is used as a substrate. Unfortunately, we were not able to observe or isolate propene since it is formed in small amounts in this reaction. The predicted formation of the alkene as a by-product was observed in the reaction of the catalyst with 3-methyl-3-azidopentane by $^1$H NMR and crystallographically when 1,1,4-trimethyl-1-azidocyclohexane was used as a substrate.

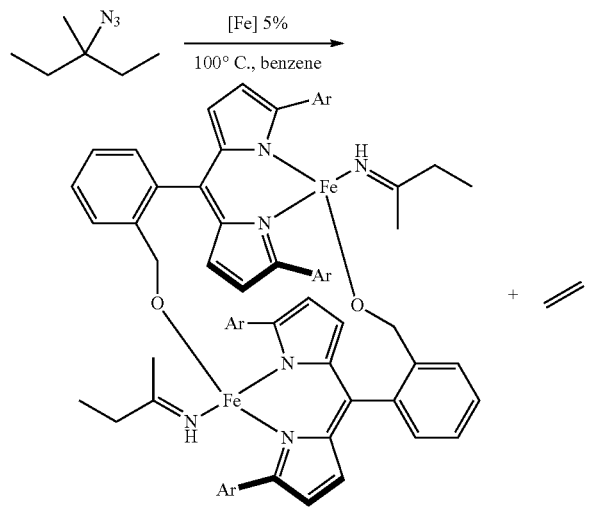

The general procedure for the catalytic formation of N-heterocyclic amines was followed. Reagents: 3-methyl-3-azido pentane (0.02 g, 0.16 mmol, 1 equiv) and [Fe] (0.0071 g, 0.05 equiv). Temperature and time of the reaction were 100° C. and 26 hours, respectively. The formation of desired N-heterocyclic amine was not observed during the course of the reaction. Instead, C—C bond cleavage occurred to give ethylene (observed by $^1$H NMR) and iron(II) 2-butimine complex (characterized by X-ray diffraction) that precipitated out of the reaction mixture (0.0063 g, 80% based on [Fe]). The solid-state molecular structure of the dimeric iron complex is shown in the crystallographic data and solid molecular structure section.

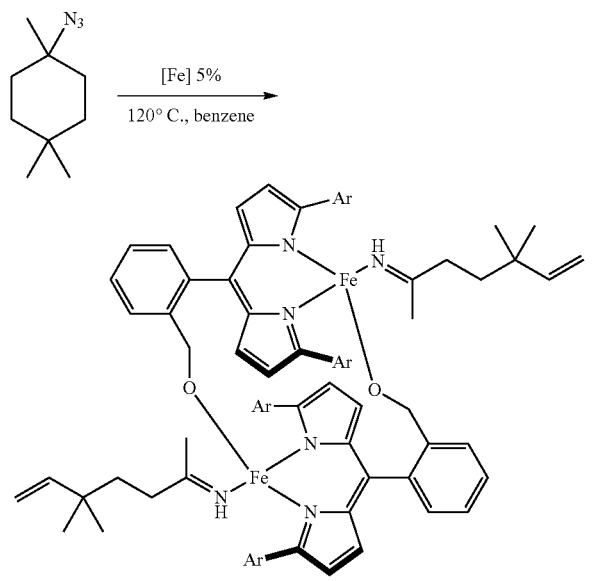

The general procedure for the catalytic formation of N-heterocyclic amines was followed. Reagents: 1,1,4-trimethyl-1-azidocyclohexanes (0.040 g, 0.24 mmol, 1 equiv) and [Fe] (0.0044 g, 0.02 equiv). Temperature and time of the reaction were 100° C. and 26 hours, respectively. When the reaction mixture was cooled, crystals of the dimeric iron complex with 3,3-dimethyl-6-azido-1-heptene coordinated to each iron center were formed (0.0011 g, 45% based on [Fe]). The solid-state molecular structure of the dimeric iron complex is shown in the crystallographic data and solid molecular structure section.

The radical initiated C—C bond breaking was also observed in the case of 1-methylazidocyclopentane as a substrate, but resulted in the formation of ring expanded product, probably due to the stability of 6-membered product. The reaction was catalytic and gave 6-methyl-2,3,4,5-tetrahydropyridine as a major product in 91% conversion with 2 mol % catalyst loading (see Example 16). The solid-state molecular structure of the dimeric iron complex with tetrahydropyridine coordinated to both iron centers is shown in the crystallographic data and solid molecular structure section.

Catalytic Performance of Selected Dimeric Iron Complexes

Example 31

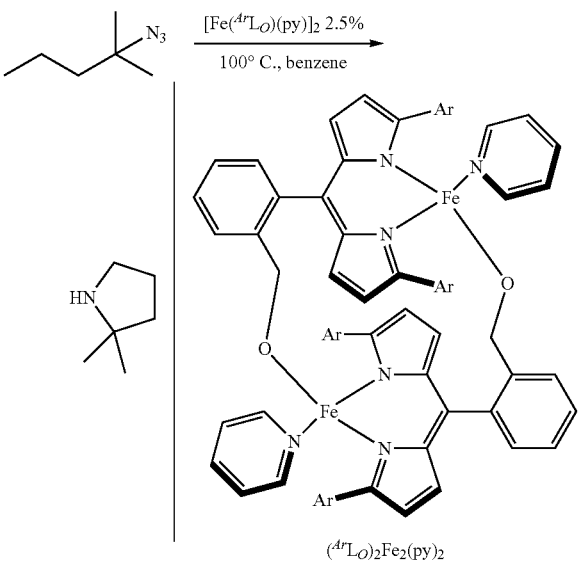

Catalytic amination using $[(^{Ar}L_O)Fe(py)]_2$ (3) as a catalyst: The general procedure for the catalytic formation of N-heterocyclic amines was followed. Reagents: 2-methyl-2-azido-pentane (13a) (0.020 g, 0.16 mmol, 1 equiv) and $[(^{Ar}L_O)Fe(py)]_2$ (3) (0.0079 g, 0.025 equiv). Temperature and time of the reaction were 100° C. and 12 hours, respectively. The yield of 2,2-dimethyl pyrrolidine (13b) after 12 hours of the reaction was estimated relative to the integration of starting azide and is 34%.

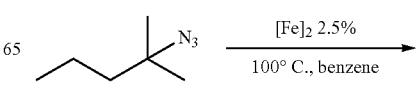

-continued

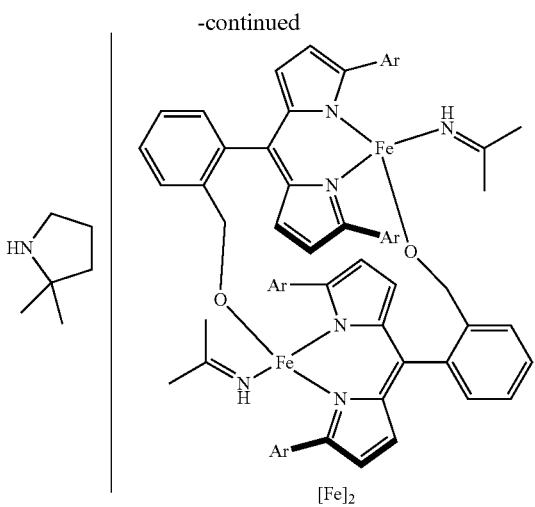

[Fe]$_2$

Catalytic amination using [Fe($^{Ar}$L$_O$)(2-iminopropane)]$_2$ as a catalyst: Crystals of [Fe($^{Ar}$L$_O$)(2-iminopropane)]$_2$ for the catalytic reaction were obtained from the catalytic amination of 2-methyl-2-azidopentane (13a). The general procedure for the catalytic formation of N-heterocyclic amines was followed. Reagents: 2-methyl-2-azido-pentane (13a) (0.010 g, 0.078 mmol, 1 equiv) and [Fe($^{Ar}$LO)(imine)]$_2$ (0.0038 g, 0.025 equiv). Temperature and time of the reaction were 120° C. and 36 hours, respectively. Complete conversion of the starting azide to the product (13b) was observed.

Crystallographic Data and Solid Molecular Structure and X-Ray Diffraction Techniques Example 32

Structures were collected on a Bruker three-circle platform goniometer equipped with an Apex II CCD and an Oxford cryostream cooling device. Radiation was from a graphite fine focus sealed tube Mo Kα (0.71073 Å) source or a Cu Kα (1.54178 Å) source. Crystals were mounted on a cryoloop or glass fiber pin using Paratone N oil. Structures were collected at 100 K. Data was collected as a series of φ and/or ω scans. Data was integrated using SAINT and scaled with either a numerical or multi-scan absorption correction using SADABS. The structures were solved by intrinsic phasing, direct methods or Patterson maps using SHELXS-9752 and refined against F2 on all data by full matrix least squares with SHELXL-97. All non-hydrogen atoms were refined anisotropically. Hydrogen atoms were placed at idealized positions and refined using a riding model. The isotropic displacement parameters of all hydrogen atoms were constrained to be 1.2 times the parameter of the atoms they were linked to (1.5 times for methyl groups). Further details on particular structures are noted below.

[($^{Ar}$L$_O$)Fe]$_6$ (2): R3: r; a=b=c=26.840 Å, α=β=γ=103.23°, V=17497 Å$^3$.

[($^{Ar}$L$_O$)Fe(py)]$_2$ (3): The structure was solved in the triclinic space group P1 with two molecules per unit cell and one molecule in the asymmetric unit. Several ligand phenyl groups as well as the pyridine ligand and a THF solvent molecule were disordered and modeled with similarity restrains and constraints.

[($^{Ar}$L$_O$)Fe((CH$_3$)$_2$C=NH)]$_2$: The structure was solved in the triclinic space group P1 with two molecules per unit cell and one molecule in the asymmetric unit. The crystal is a nonmerohedral twin and was refined using reflections in the hkl4 format created by Cell_now/Twinabs.

[($^{Ar}$L$_O$)Fe((C$_3$H$_7$)(Ph)C=NH)]$_2$: The structure was solved in the triclinic space group P with two molecules per unit cell and one molecule in the asymmetric unit. Several ligand phenyl groups as well as two benzene solvent molecules were disordered and modeled with similarity restrains and constraints. The crystal is a non-merohedral twin and was refined using reflections in the hkl4 format created by Cell_now/Twinabs.

[($^{Ar}$L$_O$) Fe(imine)]$_2$ butane-2-imine: The structure was solved in the monoclinic space group P2$_1$/c with two molecules per unit cell and half a molecule in the asymmetric unit. A benzene solvent molecule was disordered and modeled with similarity restrains and constraints.

[($^{Ar}$L$_O$)Fe(imine)]$_2$ 6-methyltetrahydropyridine: The structure was solved in the triclinic space group P1 with one molecule per unit cell and half a molecule in the asymmetric unit. The 6-methyltetrahydropyridine ligand was disordered and modeled with similarity restrains and constraints.

[($^{Ar}$L$_O$)Fe(imine)]$_2$ 5,5-dimethylhept-6-en-2-imine: The structure was solved in the monoclinic space group P2$_{1/c}$ with two molecules per unit cell and half a molecule in the asymmetric unit. One ligand phenyl group as well as several benzene solvent molecules were disordered and modeled with similarity restrains and constraints.

Octahydroindole tartrate (24b): The structure was solved in the monoclinic space group P2$_1$ with two molecules per unit cell and one molecule in the asymmetric unit.

4-pyrrolidine acetophenone (7b): The structure was solved in the orthorhombic space group Pca2$_1$ with four molecules per unit cell and one molecule in the asymmetric unit.

1-methyl-7-azabicyclo[3.2.1]octane tartrate (17b): The structure was solved in the orthorhombic space group P2$_1$2$_1$2$_1$ with four molecules per unit cell and one molecule in the asymmetric unit. The bicyclic amine showed positional disorder which was modeled with similarity restrains and constraints.

(3R,5R,8R,9S,10S,13R,14S,17R)-17-((R)-4-azido-4-methylpentan-2-yl)-3-methoxy-10,13-dimethylhexadeca-hydro-1H-cyclopenta[a]phenanthrene (25a): The structure was solved in the triclinic space group P1 with two molecules per unit cell and two molecules in the asymmetric unit.

1-methyl-9-azabicyclo[4.2.1]nonane tartrate (20b) and 1-methyl-9-azabicyclo[3.3.1]nonane tartrate (20c): The structure was solved in the orthorhombic space group P2$_1$2$_1$2$_1$ with four molecules per unit cell and one molecule in the asymmetric unit. 1-methyl-9-azabicyclo[4.2.1]nonane tartrate and 1-methyl-9-azabicyclo[3.3.1]nonane tartrate cocrystallize and were refined using a disorder model with similarity restrains and constraints.

2-(5,5-dimethylpyrrolidin-3-yl)pyridine (15b): The structure was solved in the orthorhombic space group P2$_1$2$_1$2$_1$ with four molecules per unit cell and one molecule in the asymmetric unit.

Example 33

TABLE 4

Table of experimental details for single crystal X-ray diffraction studies.[a]

| | [Fe($^{Ar}L_O$)(py)]$_2$ | [Fe($^{Ar}L_O$)((CH$_3$)$_2$C=NH)]$_2$ |
|---|---|---|
| CCDC Deposit Number | 1518638 | 1518640 |
| Chemical Formula | C$_{138}$H$_{98}$Fe$_2$N$_6$O$_2$ | C$_{134}$H$_{102}$Fe$_2$N$_6$O$_2$ |
| Formula Weight | 1983.99 | 1939.98 |
| Space Group (Z) | P$\bar{1}$ (2) | P$\bar{1}$ (2) |
| a (Å) | 13.9431(17) | 14.0315(13) |
| b (Å) | 14.3688(17) | 16.0503(19) |
| c (Å) | 15.2138(19) | 28.917(3) |
| α (deg) | 77.892(3) | 89.199(2) |
| β (deg) | 83.901(3) | 85.3537(19) |
| γ (deg) | 63.713(3) | 87.324(2) |
| Volume (Å$^3$) | 2671.7(6) | 6483.5(13) |
| μ (mm$^{-1}$) | 0.336 | 0.284 |
| T (K) | 100 (2) | 100 (2) |
| R1$^a$ (wR2$^b$) | 0.1068 (0.2728) | 0.0987 (0.2449) |
| Reflections | 9401 | 22704 |
| Radiation type | Mo K\a | Mo K\a |

TABLE 4-continued

Table of experimental details for single crystal X-ray diffraction studies.[a]

| | [Fe($^{Ar}L_O$)((C$_3$H$_7$)(Ph)C=NH)]$_2$ | [Fe($^{Ar}L_O$)(imine)]$_2$ butane-2-imine |
|---|---|---|
| CCDC Deposit Number | 1518639 | 1518642 |
| Chemical Formula | C$_{148}$H$_{114}$Fe$_2$N$_6$O$_2$ | C$_{136}$H$_{106}$Fe$_2$N$_6$O$_2$ |
| Formula Weight | 2120.22 | 1968.03 |
| Space Group (Z) | P$\bar{1}$ (2) | P2$_1$/c (2) |
| a (Å) | 16.7856(12) | 14.2214(12) |
| b (Å) | 20.1063(15) | 16.2330(14) |
| c (Å) | 20.9645(15) | 28.426(3) |
| α (deg) | 69.4654(10) | 90 |
| β (deg) | 86.9307(11) | 94.3541(17) |
| γ (deg) | 67.2757(10) | 90 |
| Volume (Å$^3$) | 6084.0(8) | 6543.4(10) |
| μ (mm$^{-1}$) | 0.299 | 0.282 |
| T (K) | 100 (2) | 100 (2) |
| R1$^a$ (wR2$^b$) | 0.0783 (0.1503) | 0.0440 (0.1058) |
| Reflections | 21524 | 11500 |
| Radiation type | Mo K\a | Mo K\a |

$^a$R1 = [Σw(Fo − Fc)$^2$/ΣwFo$^2$]$^{1/2}$;
$^b$wR2 = [Σ[w(Fo2 − Fc2)2]/Σw(Fo$^2$)$^2$]$^{1/2}$], w = 1/[σ$^2$(Fo$^2$) + (aP)$^2$ + bP], where P = [max(Fo$^2$, 0) + 2(Fc$^2$)]/3

Example 34

TABLE 5

Table of experimental details for single crystal X-ray diffraction studies.

| | [($^{Ar}L_O$)Fe(imine)]$_2$ 6-methyltetrahydropyridine | [($^{Ar}L_O$)Fe(imine)]$_2$ 5,5-dimethylhept-6-en-2-imine |
|---|---|---|
| CCDC Number | 1518643 | 1518644 |
| Moiety Formula | C$_{140}$H$_{110}$Fe$_2$N$_6$O$_2$ | C$_{146}$H$_{126}$Fe$_2$N$_6$O$_2$ |
| FW | 2018.74 | 2108.29 |
| Crystal System | triclinic | monoclinic |
| Space Group (Z) | P$\bar{1}$ (1) | P2$_1$/c (2) |
| a (Å) | 11.488(1) | 14.1237(18) |
| b (Å) | 16.2039(14) | 18.914(2) |
| c (Å) | 17.9728(15) | 30.648(4) |
| α (°) | 100.4413(14) | 90 |
| β (°) | 106.8973(14) | 92.067(2) |
| γ (°) | 104.2797(14) | 90 |
| Volume (Å$^3$) | 2984.7(4) | 8181.8(17) |
| μ (mm$^{-1}$) | 0.304 | 0.232 |
| T (K) | 100 (2) | 100 (2) |
| R1 (wR2) | 0.0465 (0.1218) | 0.0993 (0.2820) |
| Reflections | 10599 | 14626 |
| Radiation type | Mo K\a | Mo K\a |

| | Octahydroindole tartrate | 4-pyrrolidine acetophenone |
|---|---|---|
| CCDC Number | 1518645 | 1518646 |
| Moiety Formula | [C$_{11}$H$_{22}$N][C$_4$H$_5$O$_6$] | C$_{12}$H$_{15}$NO |
| FW | 317.37 | 189.25 |
| Crystal System | monoclinic | monoclinic |
| Space Group (Z) | P2$_1$ (2) | Pca2$_1$ (4) |
| a (Å) | 7.1025(3) | 15.6331(7) |
| b (Å) | 10.5673(5) | 11.9190(5) |
| c (Å) | 12.1466(5) | 5.3501(2) |
| α (°) | 90 | 90 |
| β (°) | 100.205(2) | 90 |
| γ (°) | 90 | 90 |
| Volume (Å$^3$) | 897.23(7) | 996.89(7) |
| μ (mm$^{-1}$) | 0.886 | 0.080 |
| T (K) | 100 (2) | 100 (2) |
| R1 (wR2) | 0.0212 (0.0547) | 0.0334 (0.0804) |
| Reflections | 2998 | 1759 |
| Radiation type | Cu K\a | Mo K\a |

Example 35

TABLE 6

Table of experimental details for single crystal X-ray diffraction studies.

| | 1-methyl-7-azabicyclo[3.2.1]octane tartrate | (3R,5R,8R,9S,10S,13R,14S,17R)-17-((R)-4-azido-4-methylpentan-2-yl)-3-methoxy-10,13-dimethylhexadecahydro-1H-cyclopenta[α]phenanthrene |
|---|---|---|
| CCDC Number | 1518641 | 1518648 |
| Moiety Formula | [C$_7$H$_{13}$N][C$_4$H$_5$O$_6$] | C$_{26}$H$_{45}$N$_3$O |
| FW | 261.27 | 415.66 |
| Crystal System | monocline | monocline |
| Space Group (Z) | P2$_1$2$_1$2$_1$ (4) | P1 (2) |
| a (Å) | 9.151(2) | 7.5238(4) |
| b (Å) | 10.559(3) | 9.3126(4) |
| c (Å) | 14.443(4) | 17.6937(8) |
| α (°) | 90 | 103.284(2) |
| β (°) | 90 | 90.742(2) |
| γ (°) | 90 | 93.845(2) |
| Volume (Å$^3$) | 1395.6(6) | 1203.33(10) |
| μ (mm$^{-1}$) | 0.105 | 415.65 |
| T (K) | 100 (2) | 100 (2) |
| R1 (wR2) | 0.0488 (0.1237) | 0.0844 (0.2634) |
| Reflections | 2462 | 7302 |
| Radiation type | Mo K\a | Cu K\a |

| | 1-methyl-9-azabicyclo[4.2.1]nonane tartrate and 1-methyl-9-azabicyclo[3.3.1]nonane tartrate | 2-(5,5-dimethylpyrrolidin-3-yl)pyridine |
|---|---|---|
| CCDC Number | 1518649 | 1518647 |
| Moiety Formula | [C$_9$H$_{18}$N][C$_4$H$_5$O$_6$] | C$_{11}$H$_{16}$N$_2$ |
| FW | 289.32 | 176.26 |
| Crystal System | monocline | monocline |
| Spare Group (Z) | P2$_1$2$_1$2$_1$ (4) | P2$_1$2$_1$2$_1$ (4) |
| a (Å) | 7.0899(4) | 5.926(2) |
| b (Å) | 11.7489(6) | 7.313(3) |
| c (Å) | 18.2955(10) | 23.381(9) |
| α (°) | 90 | 90 |
| β (°) | 90 | 90 |
| γ (°) | 90 | 90 |
| Volume (Å$^3$) | 1523.99(14) | 1013.3(7) |
| μ (mm$^{-1}$) | 0.042 | 0.069 |
| T (K) | 100 (2) | 100 (2) |
| R1 (wR2) | 0.0457 (0.1084) | 0.0558 (0.1614) |
| Reflections | 2625 | 1799 |
| Radiation type | Synchrotron | Mo K\a |

Example 36

TABLE 7

Catalytic annulation results to form mono- and polycyclic N-heterocycles.

| | Substrate | | Product | Yield (%), t |
|---|---|---|---|---|
| 4a | [structure: (S)-hex-5-en-1-yl azide] | 4b | [structure: 2-vinylpyrrolidine] | 80 (66)[a] 1.5 h |
| 5a | [structure: (S)-4-phenylbutyl azide] | 5b | [structure: 2-phenylpyrrolidine] | 90 (78)[a] 1.5 h |

TABLE 7-continued

Catalytic annulation results to form mono- and polycyclic N-heterocycles.

| | Substrate | | Product | Yield (%), t |
|---|---|---|---|---|
| 6a | (structure: PhCH(O-CH2CH2-N3)) | 6b | 2-phenyl-oxazolidine | 94[b], 48 h |
| 7a | (structure: 4-acetylphenyl-CH(H)-CH2CH2-CH2-N3) | 7b | 2-(4-acetylphenyl)pyrrolidine | 79 (78)[e], 6 h |
| 8a | (structure: 4-(ethoxycarbonyl)phenyl-CH(H)-CH2CH2-CH2-N3) | 8b | 2-(4-ethoxycarbonylphenyl)pyrrolidine | 82 (71)[d], 12 h |
| 9a | (structure: Me-CH(Me)-CH2CH2CH2-N3) | 9b | 2,2-dimethylpyrrolidine | 92 conv[a], 12 h, 35 |
| | | 9c | (Me)2CH-CH2CH2-CH=NH | 57 |
| 10a | (structure: Me-CH(Me)-CH2CH2-C(Me)2-N3) | 10b | 2,2,5,5-tetramethylpyrrolidine | 97 (92)[d], 24 h |
| 11a | (N-methylindol-3-yl-CH(H)-CH2CH2-C(Me)2-N3) | 11b | 3-(5,5-dimethylpyrrolidin-2-yl)-N-methylindole | 90 (84)[e], 24 h |
| 12a | (structure: Me-CH(H)-CH2CH2-C(Me)2-N3) | 12b | 2,2,5-trimethylpyrrolidine | 91 (92)[b], 72 h |
| 13a | (structure: CH3-CH2CH2-C(Me)2-N3) | 13b | 2,2-dimethylpyrrolidine | 91 (83)[c], 12 h |

TABLE 7-continued

Catalytic annulation results to form mono- and polycyclic N-heterocycles.

| | Substrate | | Product | Yield (%), t |
|---|---|---|---|---|
| 14a | (structure) | 14b | (structure) | 74 (71)[c] 48 h |
| 15a | (structure) | 15b | (structure) | (82)[c] 48 h |
| 16a | (structure) | 16b | (structure) | 92 (92)[e] 24 h |
| 17a | (structure) | 17b | (structure) | 95 (91)[b] 36 h |
| 18a | (structure) | 18b | (structure) | 95 (92)[e] 48 h |
| 19a | (structure) | 19b | (structure) | 78[e] 48 h |
| 20a | (structure) | 20b | (structure) | 82 (80) conv[e] 24 h 27 |
| | | 20c | (structure) | 56 |

TABLE 7-continued

Catalytic annulation results to form mono- and polycyclic N-heterocycles.

| | Substrate | | Product | Yield (%), t |
|---|---|---|---|---|
| 21a | | 21b | | 92 (88)[b] 24 h |
| 22a | | 22b | | 94 (90)[d] 36 h |
| 23a | | 23b | | 54[e] 48 h |
| 24a | | 24b | | 85 (77)[e] 48 h |
| 25a | | 25b | | (73)[e] 36 h |

*Catalyst loading is reported per Fe center in 2. Yields reported as $^1$H NMR yield using ferrocene as an internal standard unless otherwise noted and averaged over multiple runs. Isolated yields provided in parentheses. Conditions (T, [2]): 100° C., 1%;[a] 100° C., 2%;[b] 100° C., 5%;[c] 120° C., 1%;[d] 120° C., 2%.[e]

Example 37

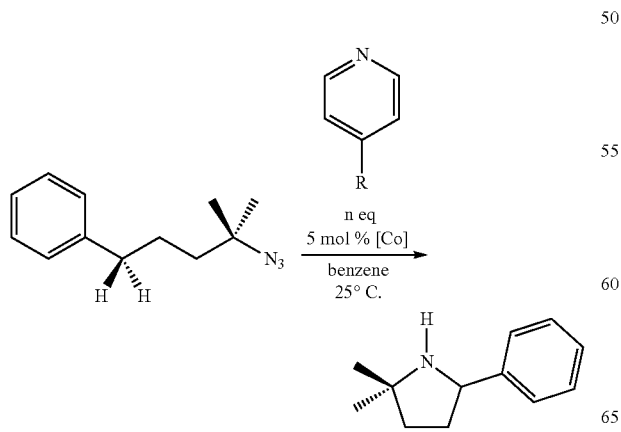

TABLE 8

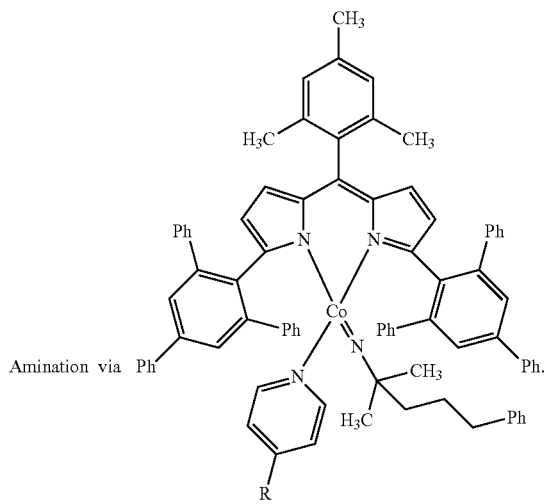

Amination via

| T (° C.) | pyr | R | yld (%) | $k_H/k_R$ |
|---|---|---|---|---|
| 25 | — | | 6.7 | |
| 80 | — | | 31 | |
| 25 | 20 | H | 90 | |
| 25 | 100 | H | 93 | |
| 25 | 5 | H | 36 | 1 |
| 25 | 5 | $^t$Bu | 89 | 1.7 |
| 25 | 5 | NMe$_2$ | 91 | 3.1 |
| 25 | 5 | CF$_3$ | 20 | 0.4 |

Example 38

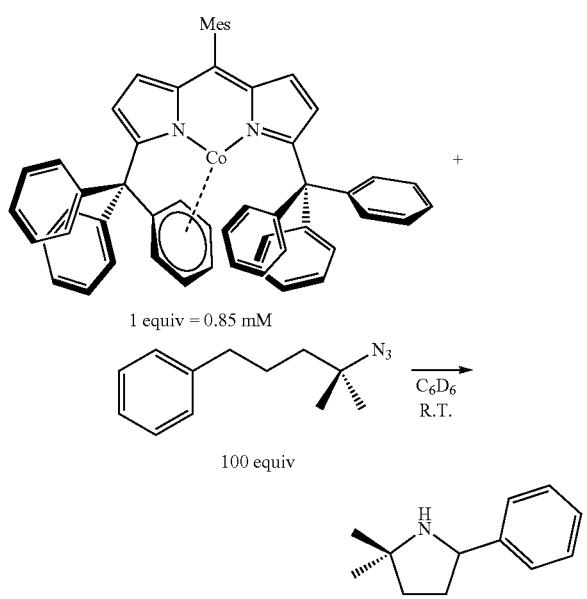

Example 39

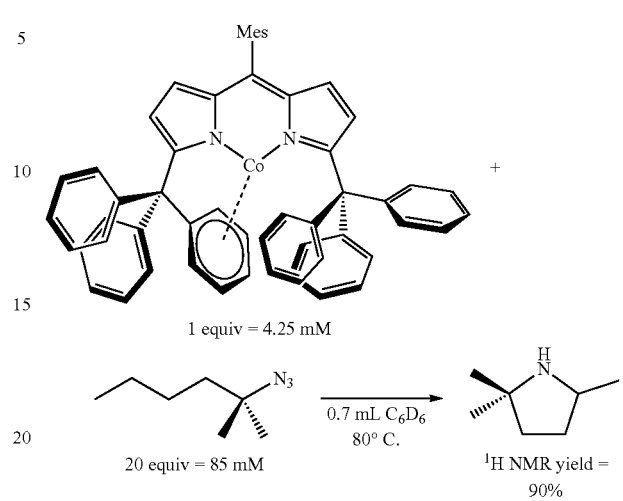

Example 40

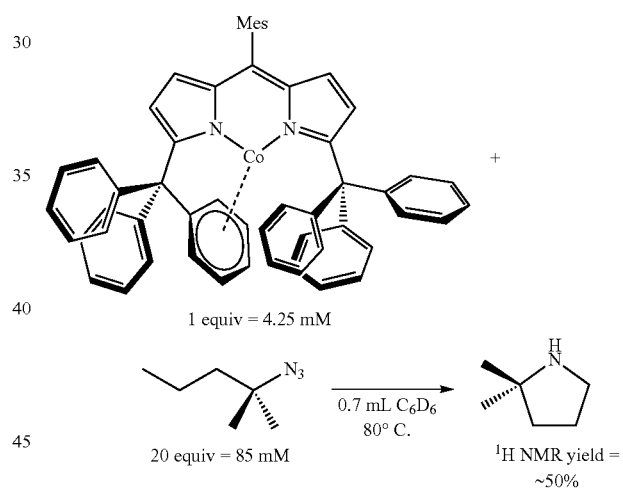

RESULTS AND DISCUSSION

Catalysts were targeted using a dianionic, tridentate dipyrrin ligand framework ($^{Ar}L_O$)H (1) (FIG. 1) (26). Alteration of the dipyrrin via installation of a benzylic alcohol at the meso-aryl ligand bridgehead provides the second anionic anchor meant to supplant the chloride ancillary in the first generation catalyst ($^{Ad}L$)FeCl(OEt$_2$) (23). Metallation of the ligand was effected thermally (80° C.) in benzene using a dibasic iron precursor (Fe$_2$(N(SiMe$_3$)$_2$)$_4$) (27), which deprotonates the ligand with concomitant iron installation to afford a microcrystalline solid that precipitates from the solution upon cooling. Although the benzylic alkoxide linkage cannot coordinate the dipyrrin-bound iron center directly, the alkoxide can bind an adjacent metal center resulting in a hexameric, ferrous wheel [($^{Ar}L_O$)Fe]$_6$ (2) (FIG. 1). The iron's primary coordination sphere maintains ideal trigonal symmetry, reflected in the observed $^{57}$Fe Mössbauer spectrum (δ: 0.69 mm/s, |ΔE$_Q$|: 0.75 mm/s), consistent with other trigonally coordinated, high-spin (dipyrrin)iron complexes reported (24). While the parent complex 2 is sparingly soluble, heating 2 in the presence of coordinating molecules induces dissociation into a soluble dimer where the iron centers are now tetrahedrally coordinated with a bound solvent (or substrate) completing the coordination sphere. For example, exposure of 2 to pyridine with mild heating affords [($^{ArO}$L)Fe(py)]$_2$ (3) as evidenced by solid-state molecular structure determination (FIG. 1) and $^{57}$Fe Mössbauer (δ: 0.90 mm/s, |ΔE$_Q$|: 2.18 mm/s). The thermally induced dissolution is facilitated by the high spin nature of [($^{ArO}$L)Fe]$_n$ which enables alkoxide lability. Furthermore, the weak C—H bonds of the alkoxide methylene unit are directed within the dimeric unit of 3, preventing deleterious oxidation that would lead to catalyst decomposition.

To assess the catalytic properties of 2, we assayed the annulation activity using a variety of azide substrates prepared from azidation of alkyl halides, alcohols (28), or carboxylic acids (29). In an example reaction, a benzene solution of 6-azido-hexene (4a) was added to a 1 mol % loading of 2 (per mole of iron) in an evacuated sealed reaction tube. No reaction occurred over one hour at room temperature owing to the insolubility of hexameric precatalyst 2 at room temperature. Heating the reaction solution to 100° C. resulted in dissociation of 2 yielding a deep purple-pink solution indicative of catalyst dissolution. After 1.5 h, complete consumption of substrate was observed by $^1$H NMR, and the pyrrolidine 4b was obtained in good yield (80% 1H NMR, 66% isolated, Table 1) after vacuum transfer and solvent evaporation. Lower reaction temperatures (60-80° C.) limit catalyst solubility and result in diminished annulated product with increasing amounts of undesired thermal decomposition of the azide substrate. Thus, catalytic amination is favored at elevated temperature with respect to thermal decomposition of the azide substrate. Of note, precatalyst 2 undergoes 80 turnovers as compared to ($^{Ad}$L)FeCl(OEt$_2$) (7.2 TON) (23) without requiring the addition of Boc$_2$O to sequester the secondary amine product. Furthermore, the re-aggregation of 2 permits facile product separation from catalyst by vacuum transfer or sublimation, avoiding a chromatographic separation step. Application of these reaction conditions to a range of substrates containing benzylic C—H bonds and a variety of chemical functionalities common to bioactive scaffolds (i.e., amines 5b-8b, ethers 6b, ketones 7b, esters 8b) affords annulated products in good isolated yields (71-78%, results presented in Table 7). These results demonstrate the catalytic viability of precatalyst 2 and its tolerance to Lewis basic functionalities.

Figure 3:
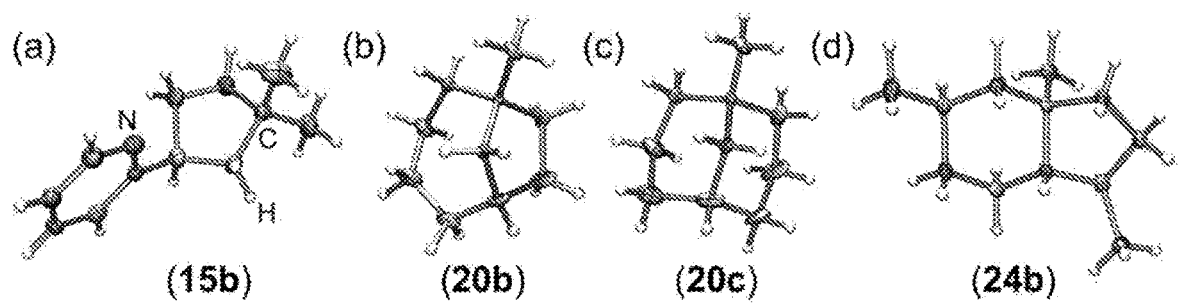
FIG. 3 shows the solid-state molecular structures of annulation products 2-(5,5-dimethylpyrrolidin-3-yl)pyridine 15b arising from primary C—H bond amination (a); protonated cations of 1-methyl-9-azabicyclo[4.2.1]nonane 20b (b), 1-methyl-9-azabicyclo[3.3.1]nonane 20c (c), and (3S,3aS,6R,7aR)-3,6,7a-trimethyloctahydro-1H-indole 24b (d).
Figure 4:
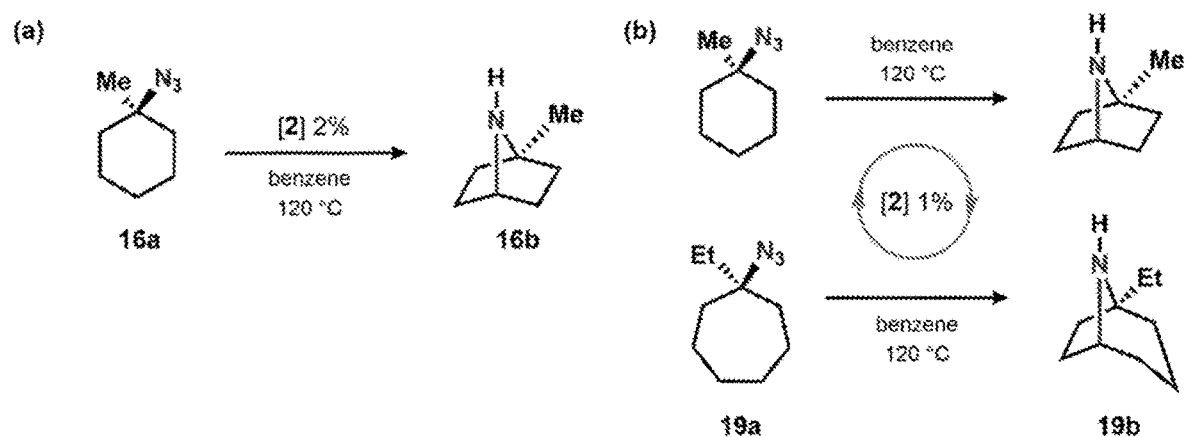
FIG. 4 shows the catalyst recycling experiments of (a) 1-methyl-1-azidocyclohexane (16a) and (b) 16a followed by 1-ethyl-1-azidocycloheptane (19a).
Figure 5:
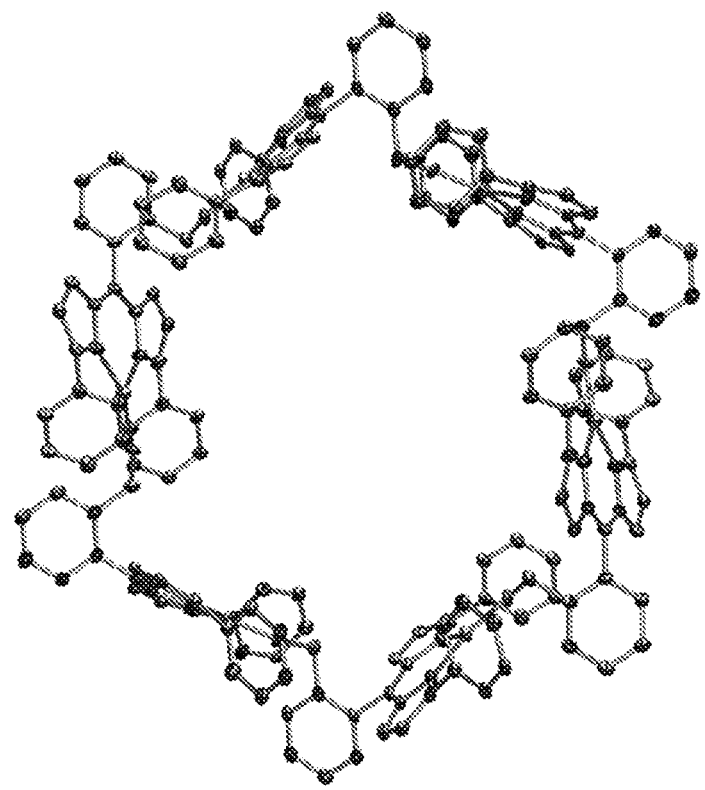
FIG. 5 shows the solid-state molecular structure for $[(^{Ar}L_O)Fe]_6$ (2) with thermal ellipsoids at 40% probability level. Hydrogen atoms, solvent molecules, disorder, the second molecule in the unit cell and part of the ligand are omitted for clarity.
Figure 6:
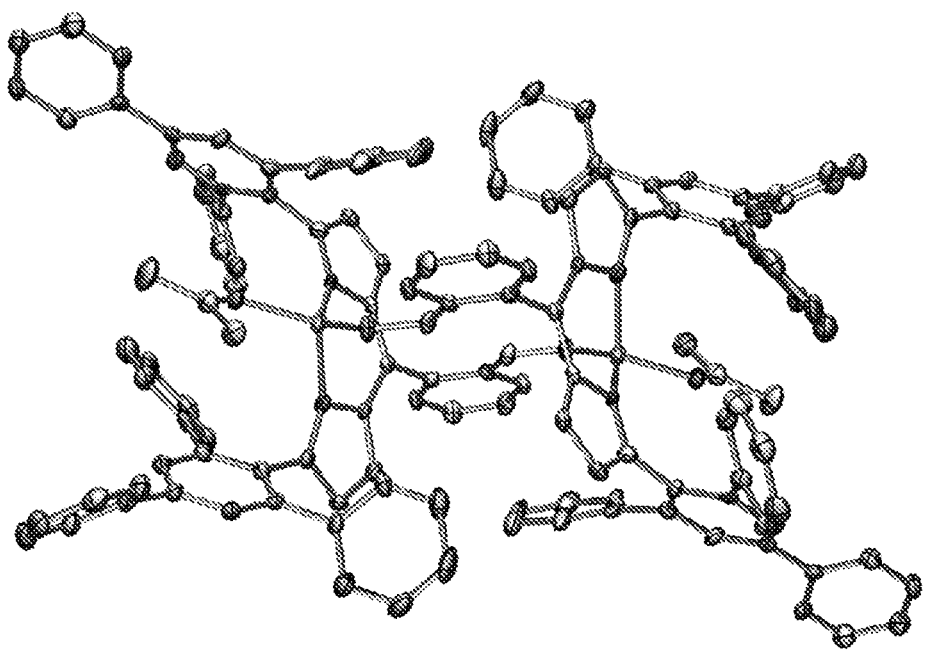
FIG. 6 shows the solid-state molecular structure for $[(^{Ar}L_O)Fe((CH_3)_2C=NH)]_2$ with thermal ellipsoids at 50% probability level. Hydrogen atoms, solvent molecules, disorder and the second molecule in the unit cell are omitted for clarity.
Figure 7:
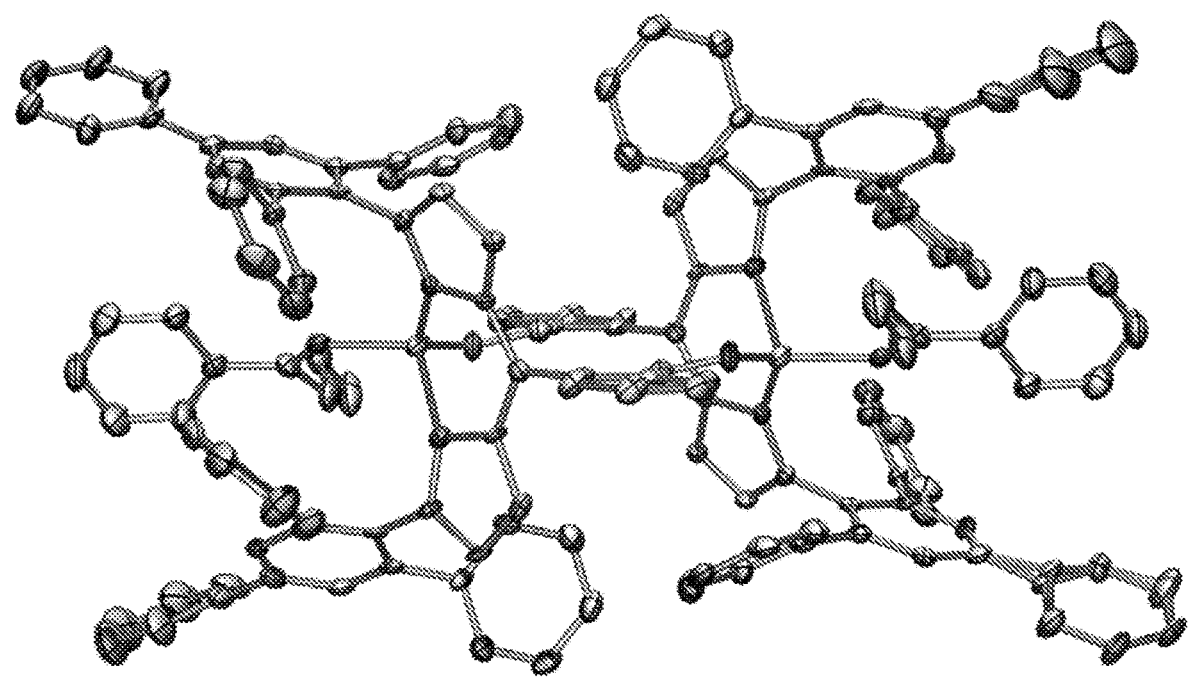
FIG. 7 shows the solid-state molecular structure for $[(^{Ar}L_O)Fe((C_3H_7)(Ph)C=NH)]_2$ with thermal ellipsoids at 50% probability level. Hydrogen atoms, solvent molecules, disorder and the second molecule in the unit cell are omitted for clarity.
Figure 8:
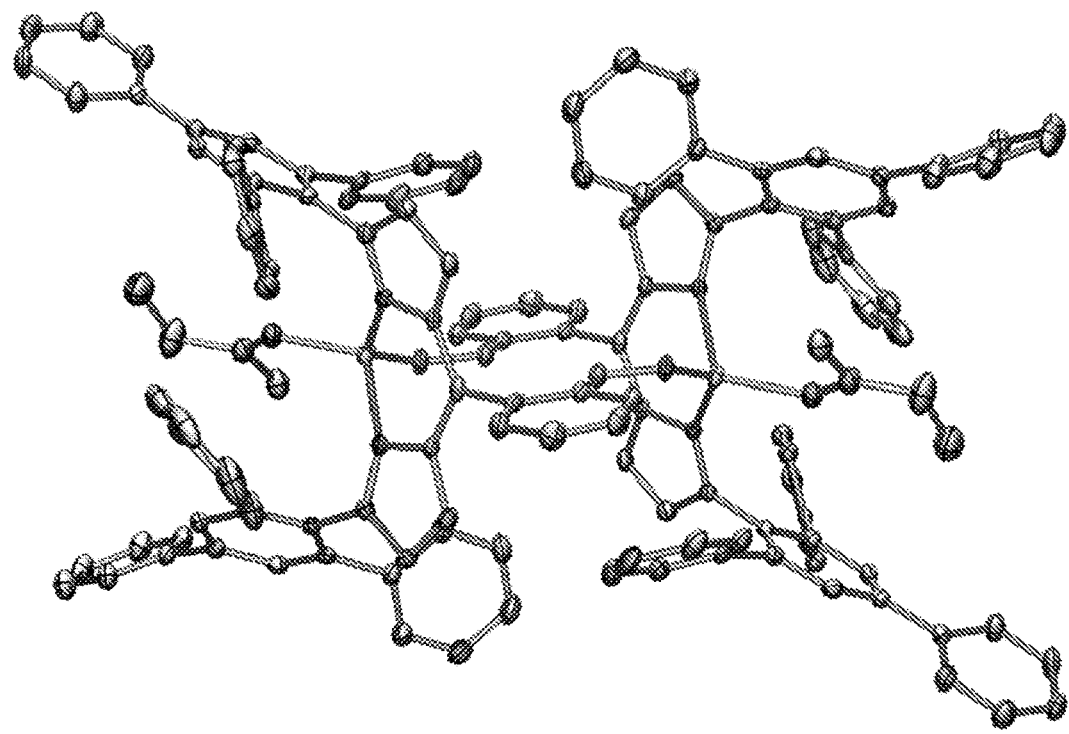
FIG. 8 shows the solid-state molecular structure for [($^{Ar}L_O$)Fe(imine)]$_2$ (imine=butane-2-imine) with thermal ellipsoids at 50% probability level. Hydrogen atoms, solvent molecules, disorder and the second molecule in the unit cell are omitted for clarity.
Figure 9:
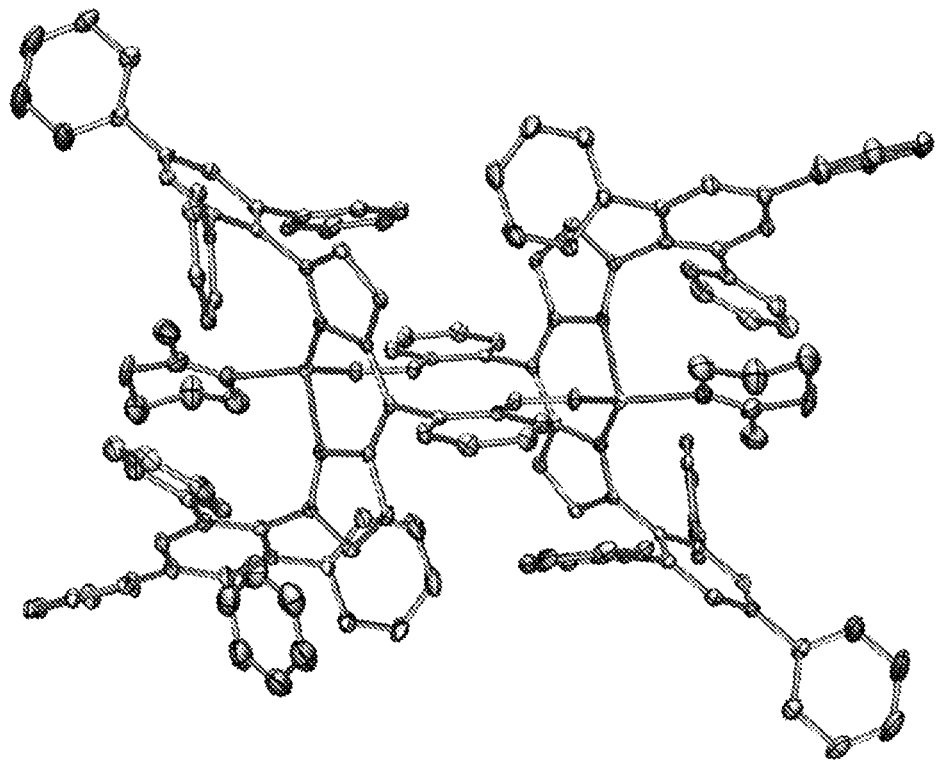
FIG. 9 shows the solid-state molecular structure for [($^{Ar}L_O$)Fe(imine)]$_2$ (imine=6-methyl tetrahydropyridine) with thermal ellipsoids at 50% probability level. Hydrogen atoms, solvent molecules, disorder and the second molecule in the unit cell are omitted for clarity.
Figure 10:
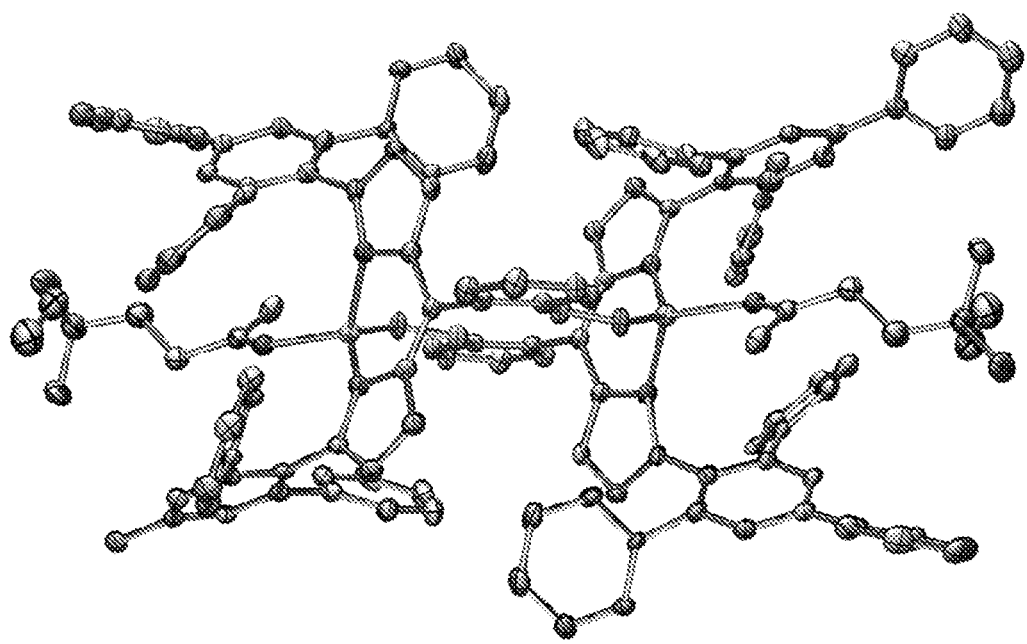
FIG. 10 shows the solid-state molecular structure for [($^{Ar}L_O$)Fe(imine)]$_2$ (imine=5,5-dimethylhept-6-en-2-imine) with thermal ellipsoids at 50% probability level. Hydrogen atoms, solvent molecules, disorder and the second molecule in the unit cell are omitted for clarity.
Figure 11:
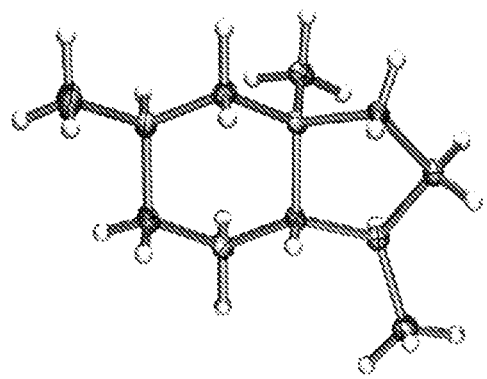
FIG. 11 shows the solid-state molecular structure for octahydroindole tartrate (24b) with thermal ellipsoids at 50% probability level. Solvent molecules, and counterion are omitted for clarity.
Figure 12:
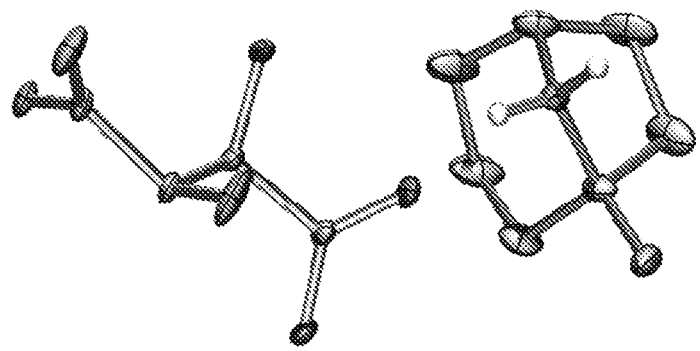
FIG. 12 shows the solid-state molecular structure for 1-methyl-7-azabicyclo[3.2.1]octane tartrate (17b) with thermal ellipsoids at 30% probability level. Hydrogen atoms and disorder are omitted for clarity.
Figure 13:
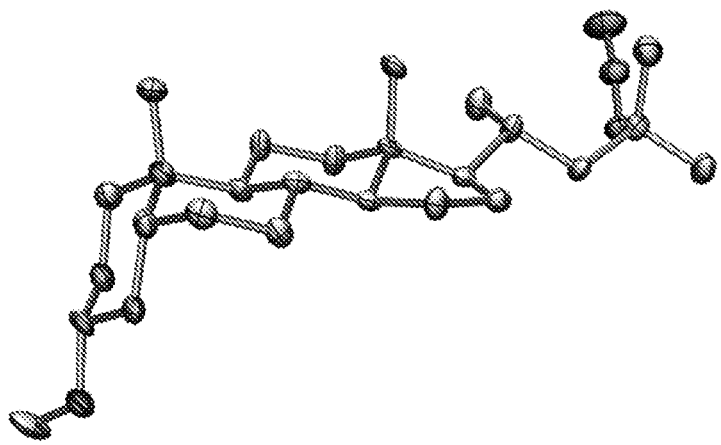
FIG. 13 shows the solid-state molecular structure for (3R,5R,8R,9S,10S,13R,14S,17R)-17-((R)-4-azido-4-methylpentan-2-yl)-3-methoxy-10,13-dimethylhexadecahydro-1H-cyclopenta[α]phenanthrene (25a) with thermal ellipsoids at 50% probability level. Hydrogen atoms and the second molecule in the unit cell are omitted for clarity.
Figure 14:
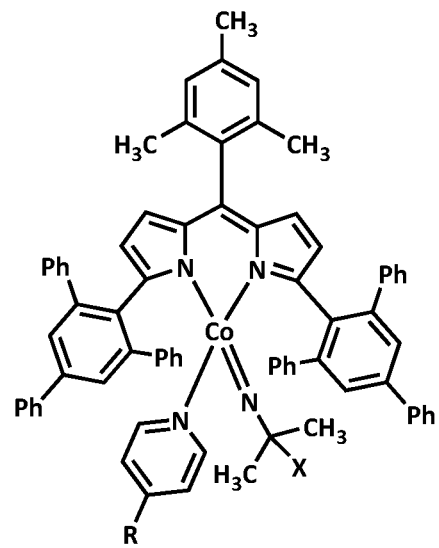
FIG. 14 shows the structures for cobalt-based amination catalysts (2-IIa-2-IIc).
Figure 15:
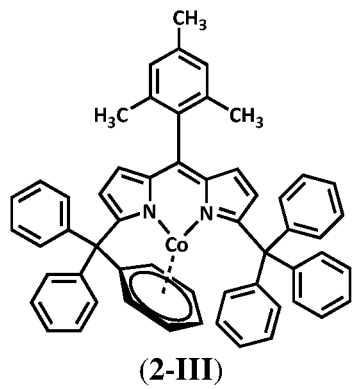
FIG. 15 shows the structure for cobalt-based amination catalyst (2-III).
Figure 16:
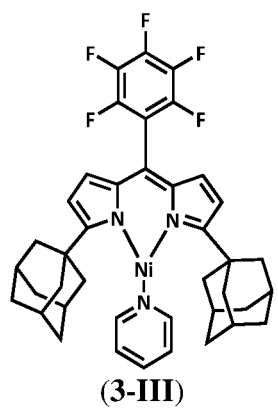
FIG. 16 shows the structure for nickel-based amination catalyst (3-III).
Figure 17:
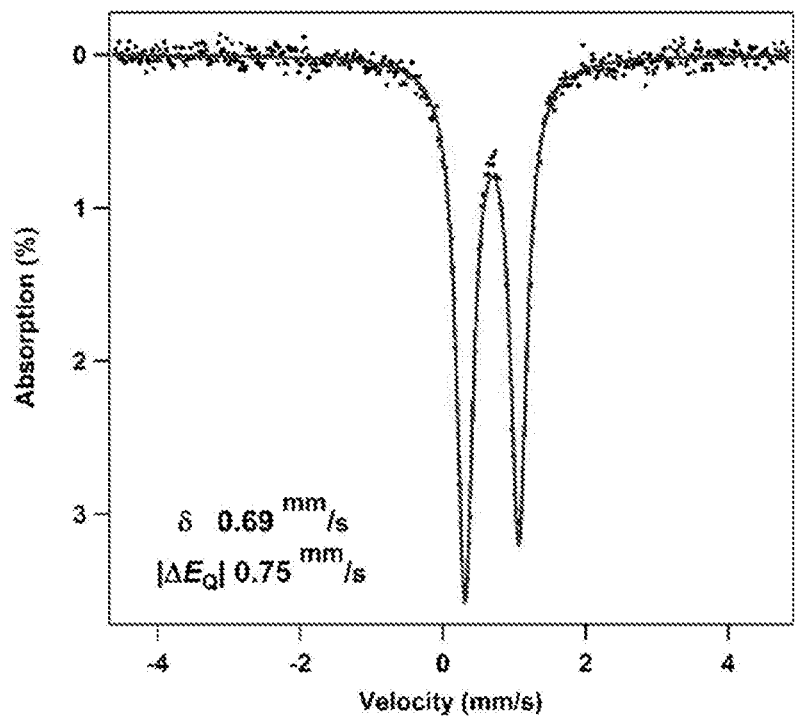
FIG. 17 shows the zero-field $^{57}$Fe Mossbauer spectrum of [Fe($^{Ar}$LO)]$_6$. Isomer shift and quadrupole splitting are reported relative to Fe foil at room temperature. Data (black dots) and fit (black line) using listed parameters.
Figure 18:
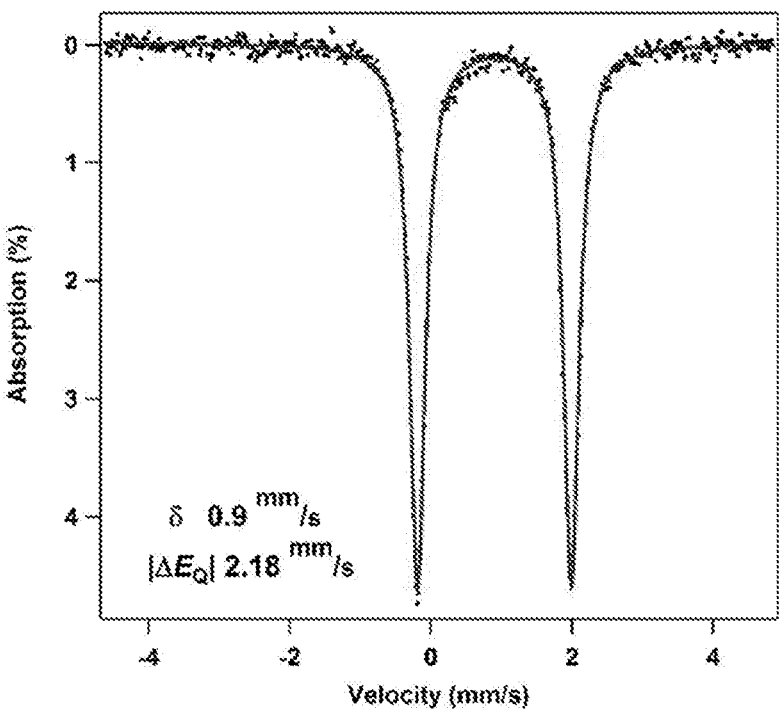
FIG. 18 shows the zero-field $^{57}$Fe Mössbauer spectrum of [Fe($^{Ar}L_O$)(py)]$_2$. Isomer shift and quadrupole splitting are reported relative to Fe foil at room temperature. Data (black dots) and fit (black line) using listed parameters.
Figure 19:
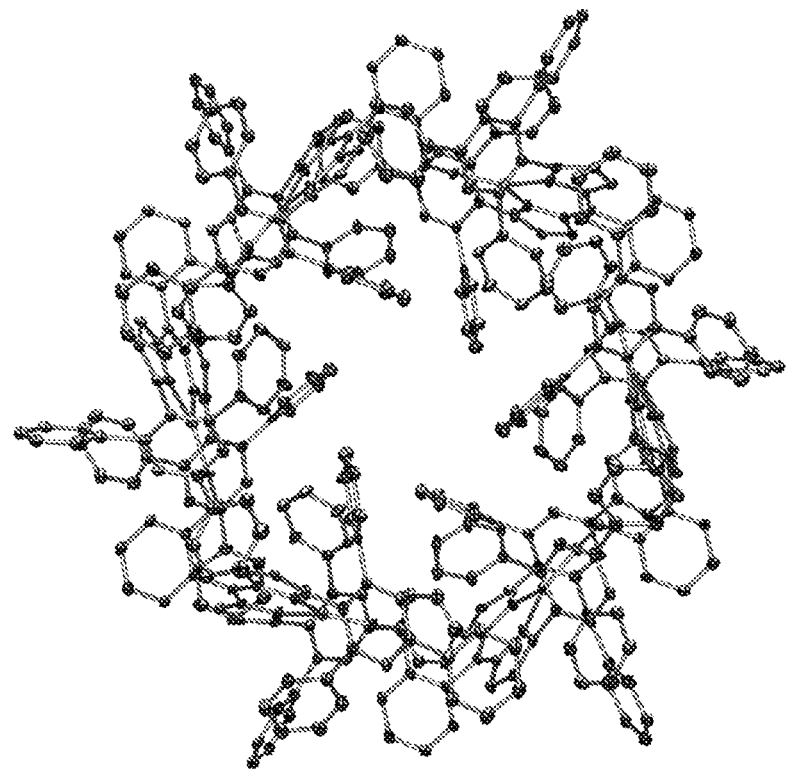
FIG. 19 shows the solid-state molecular structure for [($^{Ar}L_O$)Fe]$_6$ (2) with thermal ellipsoids at 30% probability level. Hydrogen atoms, solvent molecules, disorder, the second molecule in the unit cell and part of the ligand are omitted for clarity.
Figure 20:
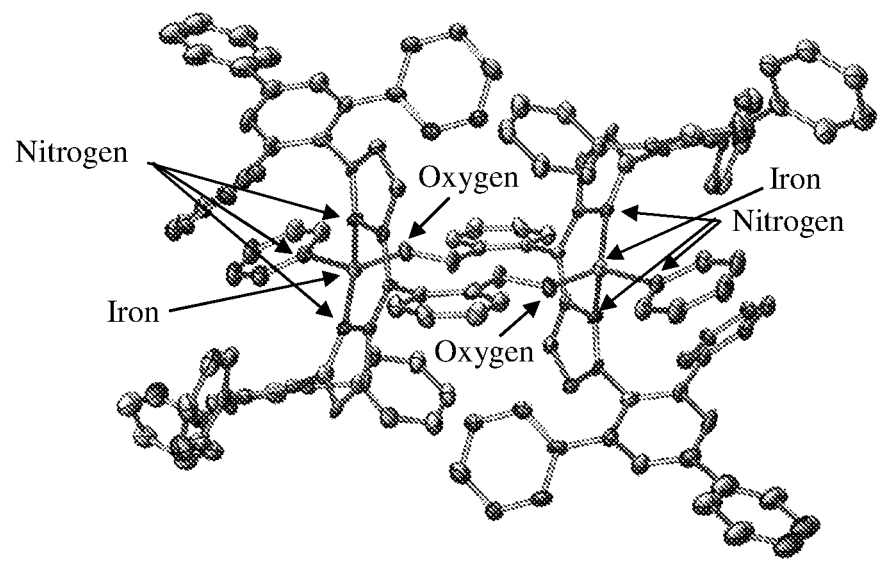
FIG. 20 shows the solid-state molecular structure for [Fe($^{Ar}L_O$)(py)]$_2$ with thermal ellipsoids at 30% probability level. Hydrogen atoms, solvent molecules, disorder and the second molecule in the unit cell are omitted for clarity. Iron, nitrogen, and oxygen=labelled, carbon=remaining gray atoms.
Figure 21:
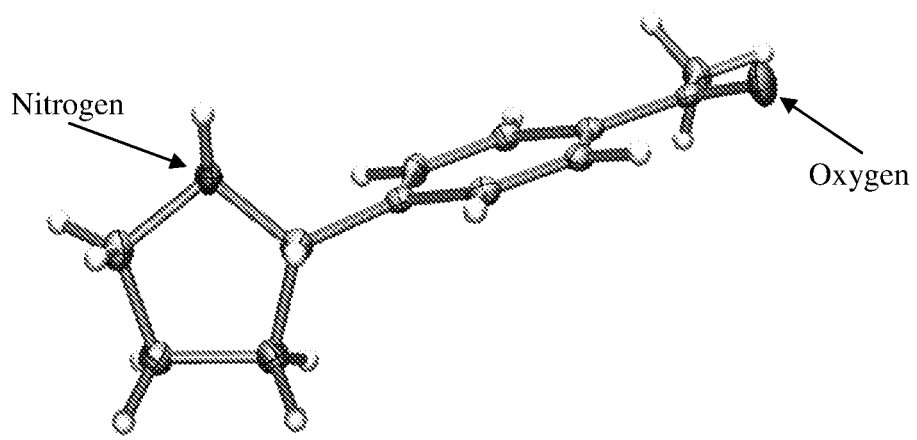
FIG. 21 shows the solid-state molecular structure for 4-pyrrolidine acetophenone with thermal ellipsoids at 50% probability level. Nitrogen and oxygen=labelled, carbon=remaining gray atoms, hydrogen=white.
Figure 22:
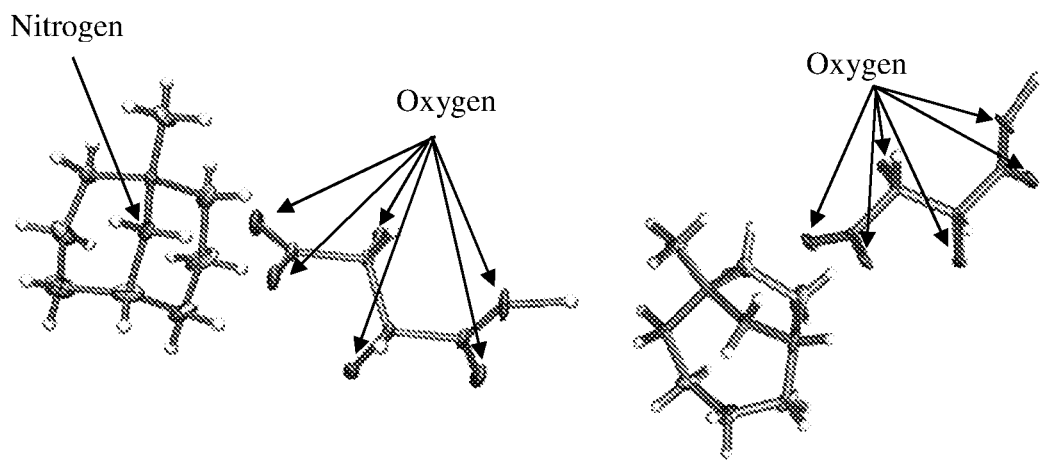
FIG. 22 shows the solid-state molecular structure for 1-methyl-9-azabicyclo[4.2.1]nonane tartrate and 1-methyl-9-azabicyclo[3.3.1]nonane tartrate with thermal ellipsoids at 30% probability level. Nitrogen and oxygen=labelled, carbon=remaining gray atoms, hydrogen=white.
Figure 23:
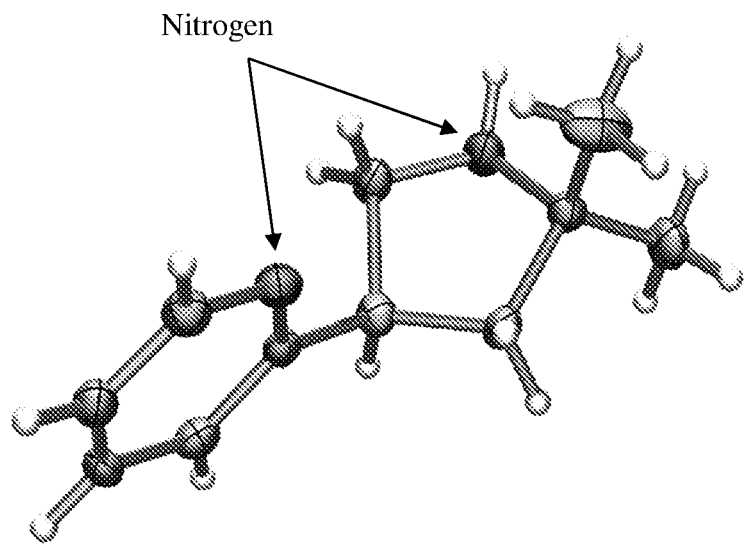
FIG. 23 shows the solid-state molecular structure for 2-(5,5-dimethylpyrrolidin-3-yl)pyridine with thermal ellipsoids at 40% probability level. Nitrogen=labelled, carbon=gray, hydrogen=white.
Figure 24:
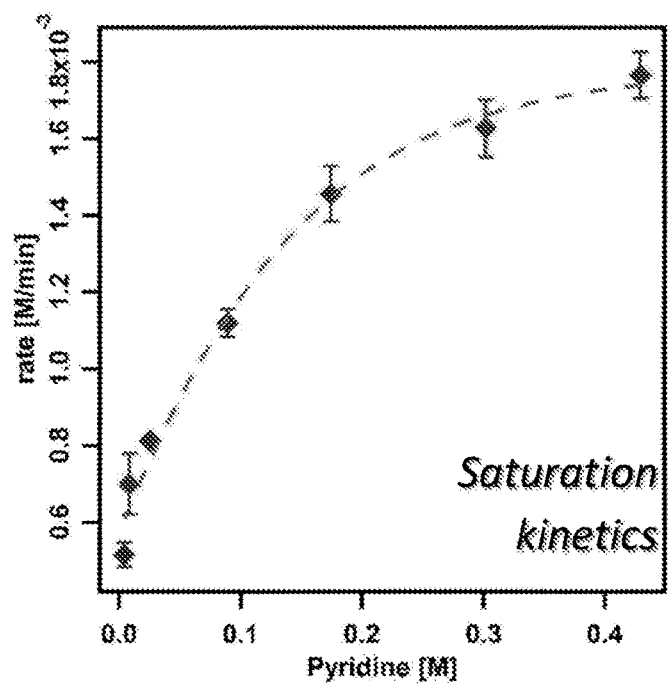
FIG. 24 shows the saturation curve for the saturation kinetics data shown in Example 37.
Figure 25A:
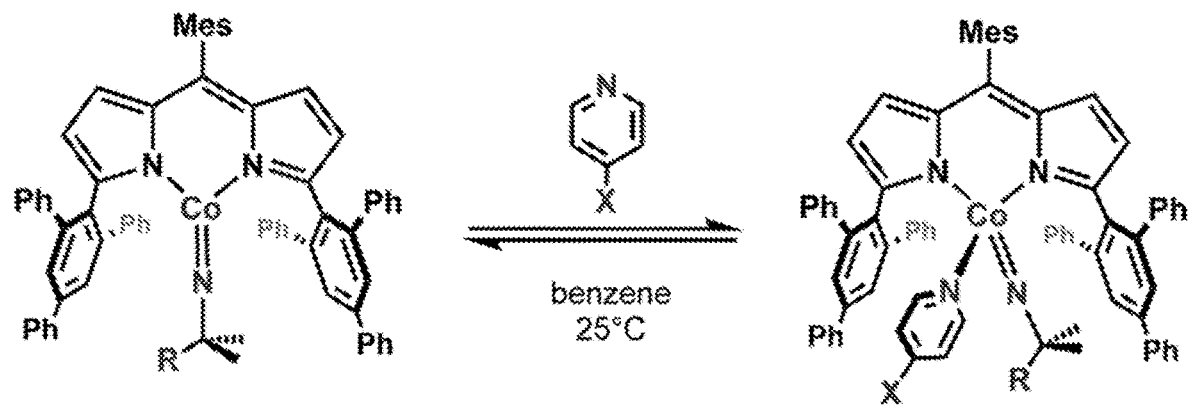
FIG. 25A shows pyridine activation of cobalt imido complex to form 2-IIa-2-IIc and derivatives.
Figure 25B:
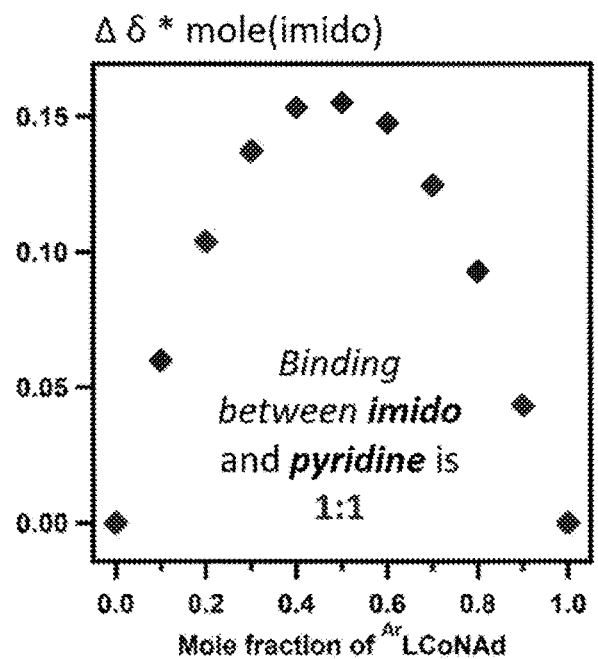
FIG. 25B shows that the binding between the cobalt imido complex and pyridine is 1:1.
Figure 26:
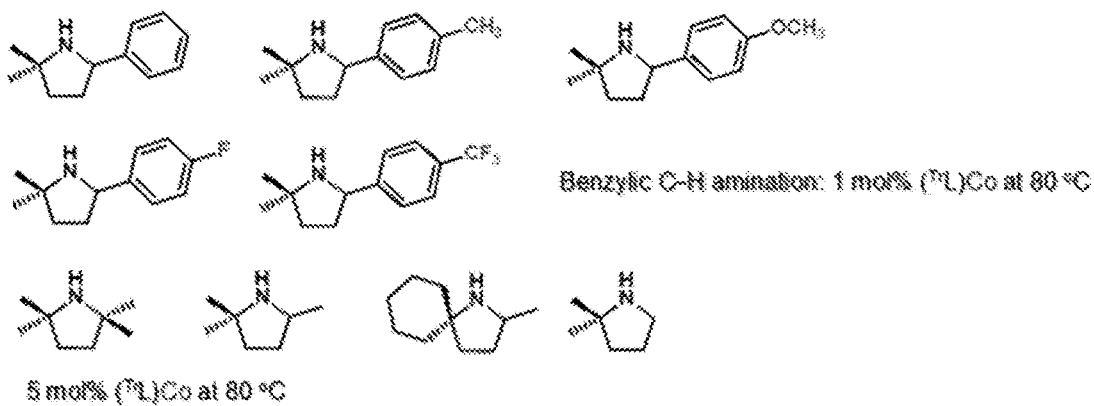
FIG. 26 shows the amination products that can be formed with compound 2-III.
Figure 27:
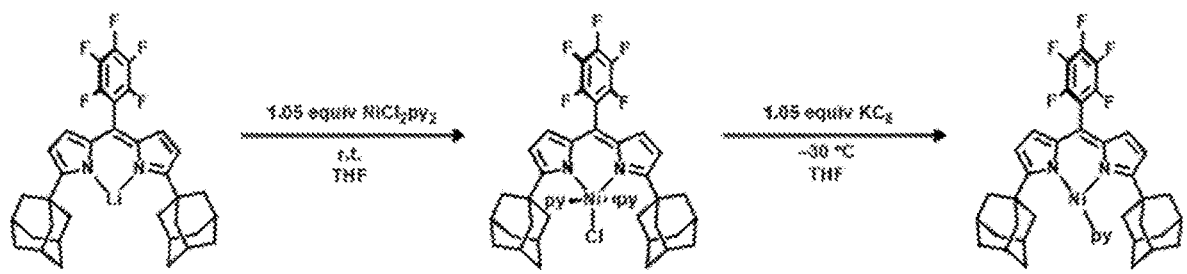
FIG. 27 shows the synthesis of compound 3-III.
Figure 28:
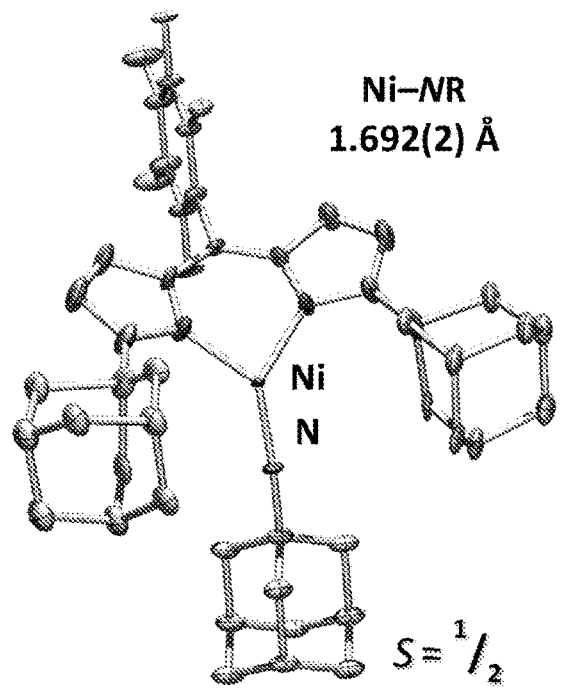
FIG. 28 shows the crystal structure of adamantylamine derivative of compound 3-III.
Figure 29:
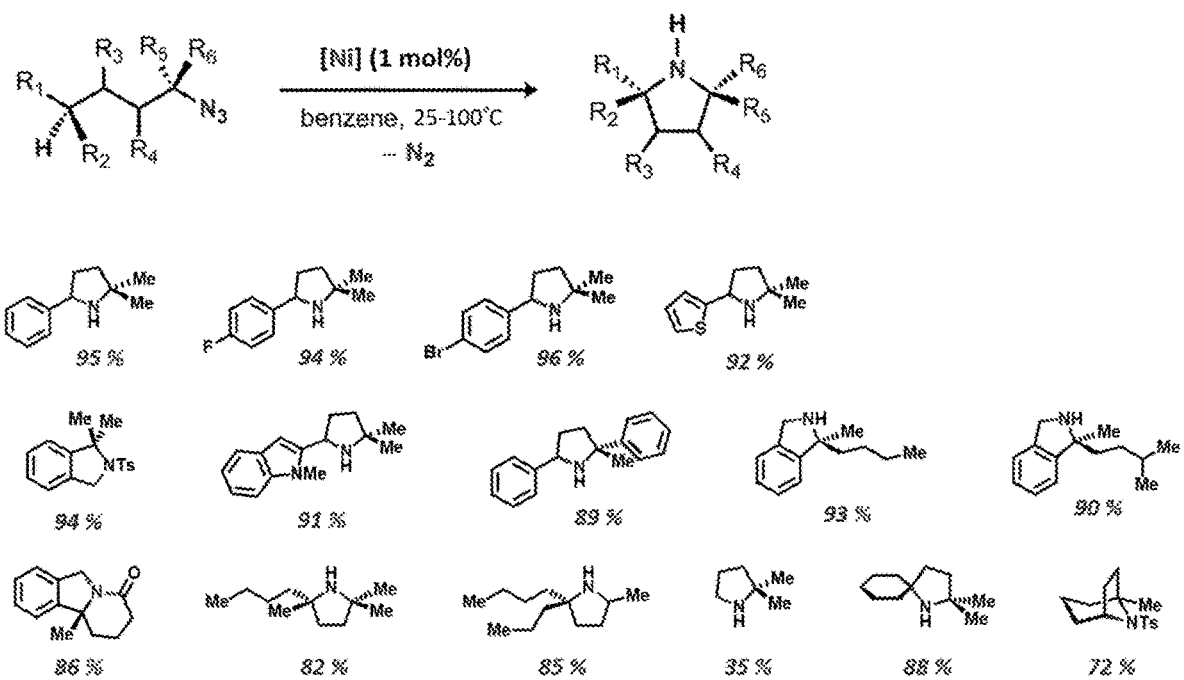
FIG. 29 shows the amination products that can be formed with compound 3-III.

The activity and selectivity of 2 were further tested towards functionalization of unactivated C—H bonds. Though challenging due to their high bond dissociation energies, these substrates attractive targets due to the abundance of these bonds in organic scaffolds. Heating a mixture of 2 (1 mol %) and 1-azido-4-methylpentane (9a) resulted in complete consumption of the azide and formation of the desired product 2,2-dimethylpyrrolidine (9b, 35%) and an undesired 5-methylhexane-1-imine (9c, 57%) potentially arising from α-H migration (30). The formation of imine side products was found to be dependent on the strength of the C—H bond being activated and was observed with other azides containing methylene units adjacent to the azido functionality. To eliminate this unwanted side reaction, α-gem-dialkyl substituted substrates containing tertiary (10a), secondary (12a), and primary (13a-15a) target C—H bonds (bond dissociation energies: 90-103 kcal/mol) were tested to give selective formation of annulated products in excellent isolated yields (71-92%) using only 1-5 mol % catalyst loadings (Table 7, 10b-15b). Substrates 11a and 15a contain indole and pyridine functionalities, respectively, are also tolerated in the catalysis, cyclizing to the respective pyrrolidine products in excellent isolated yields (82-84%). The five membered ring containing products were exclusively formed in the catalytic process, despite the ability of the catalyst to activate the whole spectrum of C—H bonds, highlighting the remarkable chemoselectivity of the catalyst. For example, cleavage of the doubly activated benzylic, tertiary C—H bond in 15a could potentially yield the four-membered azetidine heterocycle, but the pyrrolidine product 15b is exclusively formed resulting upon primary C—H bond functionalization (FIG. 3).

The observed reactivity, selectivity, functional group tolerance, and protocol simplicity for product isolation makes the catalytic system based on 2 a powerful annulation strategy that can be applied for the synthesis of nitrogen-containing heterocycles of greater complexity than simple pyrrolidines (e.g., polycyclic heteroamines). In particular, substituted bicyclic, spiro, and fused heterocycles are common motifs in various pharmaceutical and bioactive molecules (31-32), and thus, are attractive targets for the utilization of direct C—H amination processes. Bicyclic N-heterocycles based on [2.2.1], [3.2.1], and [3.3.1] rings in the core structure are part of large families of highly potent biologically and synthetically derived alkaloids such as ecgonine, cocaine, granisetron, and adaline (32-34). Heating a solution of 1-azido-1-methylcyclohexane (16a) with 2 mol % of 2 at 120° C. cleanly forms 1-methyl-7-azabicyclo[2.2.1]heptane (16b), isolable by vacuum transfer to afford a colorless oil in excellent yield (92%, Table 7). Expanding the azide ring size gives access to various tropane scaffolds. For example, applying the same reaction conditions to the cycloheptane-derived azide 17a affords the corresponding 1-methyl-8-azabicyclo[3.2.1]octane (17b) in high yield (91%, Table 7). Increasing the size of the substrate alkyl substituents on the azide-bearing carbon (18a, 19a) is also tolerated, though longer reaction times (48 h) are required to consume the azide (18b 92%; 19b 78%) owing to the increased substrate steric demands. Catalytic amination of 1-azido-1-methylcyclooctane (20a) results in the formation of two products in a 1:2 ratio in an overall 80% isolated yield, corresponding to two structural isomers, the [4.2.1] and [3.3.1] bicycles. Crystallographic analysis on crystals grown from tartaric acid addition to the product revealed the symmetrical 1-methyl-9-azabicyclo[3.3.1]nonane (20c) being the major component (56%) and the statistically favored 1-methyl-9-azabicyclo[4.2.1]nonane (20b) being a minor product (27%). (FIG. 3). Further demonstrating the robustness of the catalytic amination reaction, cyclization of 1-azido-1-methylcyclooctane (20a) was performed utilizing 0.5 g of substrate without a decrease in yield. Subjecting 1-azido-1-methylcyclopentane (22a) to the catalytic conditions did not furnish the anticipated 1-methyl-5-azabicyclo[2.1.1]hexane, rather the ring-expanded tetrahydropyridine product (22b, 91%) was exclusively obtained. The unexpected product potentially arises from C—C bond cleavage from the iminyl intermediate followed by radical recombination outcompeting the difficult amination reaction to produce a strained azetidine-pyrrolidine tropane.

The methodology was extended further to the synthesis of more elaborate fused heterocyclic products. Selective formation of 2,2-dimethyl-1-azaspiro[4.5]decane (22b) in 90% isolated yield was observed when (3-azido-3-methylbutyl)cyclohexane (22a) was heated with 2 (1 mol %), demonstrating remarkable selectivity towards the generation of the azaspiro compound (23). Fused aromatic heterocycles can also be generated, highlighted by the formation of 1,1-dimethylisoindoline (23b) in 56% yield upon treatment of azide 23a with 2 (2 mol %). The diminished yield is attributable to the formation of unidentified side products. Lastly, we adapted the established protocol to the elaboration of natural product derived substrates. Subjecting (1R, 2S,5R)-1-azido-2-isopropyl-1,5-dimethylcyclohexane 24a, derived from naturally occurring l-menthone (35-36), to the amination protocol yielded (3S,3aS,6R,7aR)-3,6,7a-trimethyloctahydro-1H-indole (24b) as the major product (77%), isolated by vacuum transfer as a single enantiomer (as determined by crystallographic analysis of the tartaric acid conjugate, FIG. 3). We reason the octahydroindole product arising from selective activation of an isopropyl primary C—H bond (over 3 other accessible C—H bonds) is a result of the favored cyclohexane chair conformation with the substrate methyl, azido, and isopropyl functional groups locked into equatorial positions, orienting the azide and isopropyl methyl substituent proximally. To assess if the annulation protocols could be extended to larger, more complex substrates, the litocholic acid (37) derived azide 25a was evaluated. The reaction mixture showed complete consumption of the starting azide after 48 hours. The structure of the product 25b was determined by $^1$H NMR, identifying three new resonances that were assigned to the hydrogens of pyrrolidine ring arising from chemoselective activation of primary C—H bond of the methyl group over the weaker tertiary C—H bond at the base of the D ring of the steroid. Thus, the remarkable activity and selectivity of 2 towards amination of 25a indicates that the sterically encumbered nature of the catalyst does not restrict amination of complex and heavily functionalized substrates and emphasizes the potency of 2 for a predictable functionalization of the molecules in the late stages of a synthesis.

The mechanism of catalytic action for 2 is proposed to closely mirror its predecessor ($^{Ad}$L)FeCl(OEt$_2$) (23) following dissociation of 2 into a catalytically active dimeric form akin to the formation of 3 in the presence of pyridine. The thermally induced dissolution, likely enhanced by ligation of azido substrates, is facilitated by the high spin nature of [($^{Ar}$L$_O$)Fe]$_n$ which enables alkoxide lability, likely facilitated by dipyrrin tautomerization to the bispyrrolicbenzofuran. In the presumed active catalyst dimeric form, the weak C—H bonds of the alkoxide methylene unit are directed within the dimeric unit, preventing deleterious oxidation that would lead to catalyst deactivation. Subsequent extrusion of dinitrogen from a bound azide to yield an iminyl radical likely leads to a stepwise (H-atom abstraction, radical rebound) (38) or concerted nitrene insertion (39) into substrate C—H bonds to drive the annulation reaction. A common side reaction observed in the annulation catalysis is substrate imine fragmentation arising from C—C bond homolysis (see FIG. S186-190), suggesting the intermediacy of iminyl radicals (24-25). Product expulsion from the dimer is facilitated by the steric demands of the encumbered dipyrrin ligand, as well as the reduced electrophilicity of the iron catalyst (40). Substitution of the alkoxide ligand for the halide in ($^{Ad}$L)FeCl(OEt$_2$) (23) leads to a substantial cathodic shifting of the iron center, resulting in diminished Lewis acidic character. Lastly, the ligand lability which affords the catalytically active dimer also permits thermally induced catalyst re-aggregation upon cooling following substrate consumption. This permits catalyst recycling with negligible loss in catalytic efficacy over multiple runs as evidenced by the annulation of 1-methyl-1-azidocyclohexane (16a) (Table 1). Catalyst recycling was performed by subjecting catalyst to substrate in deuterated benzene and heated to 100° C. for 36 h while monitoring the reaction progression by $^1$H NMR. The product was separated from the catalyst via vacuum transfer. Ferrocene was added to the isolated product in benzene-d6 and the yield was determined by $^1$H NMR. The catalyst was subjected to a new batch of substrate in benzene-d6 for the next cycle of amination. Catalyst recycling increases the overall yields of annulated product significantly (TON: 175-192) and can be applied to catalyzing different substrates without loss of efficacy (1-methyl-1-azidocyclohexane 16a and 1-ethyl-1-azidocycloheptane 19a in Table 2).

REFERENCES

1) J. F. Hartwig, J. Am. Chem. Soc. 138, 2 (2016).
2) J. F. Hartwig, M. A. Larsen, ACS Cent. Sci. 2, 281 (2016).
3) H. M. L. Davies, D. Morton, J. Org. Chem. 81, 343 (2016).
4) P. H. Dixneuf, H. Doucet, C—H Bond Activation and Catalytic Functionalization I. Top. Organomet. Chem. 55, 1 (2016).
5) R. Shang, L. Ilies, E. Nakamura, Chem. Rev. 117, 9086 (2017).
6) S. D. Roughley, A. M. Jordan, J. Med. Chem. 54, 3451 (2011).
7) P. R. Ortiz de Montellano; Ed. Cytochrome P450: Structure, Mechanism, and Biochemistry, 4th ed.; Kluwer Academic/Plenum Publishers: New York, 2005.
8) J. T. Groves, J. Inorg. Biochem. 100, 434 (2006).
9) D. P. Galonic, E. W. Barr, C. T. Walsh, M. J. Bollinger, C. Krebs, Nat. Chem. Bio. 3, 113, (2007).
10) R. T. Gephart III, C. L. McMullin, N. G. Sapiezynski, E. S. Jang, M. J. B. Aguila, T. R. Cundari, T. H. Warren, J. Am. Chem. Soc. 134, 17350 (2012).
11) W. Liu, X. Huang, M.-J. Cheng, R. J. Nielsen, W. A. Goddard III, J. T. Groves, Science 337, 1322 (2012).
12) A. Sharma, J. F. Hartwig, Nature 517, 600 (2015).
13) W. Zhang, F. Wang, S. D. McCann, D. Wang, P. Chen, S. S. Stahl, G. Liu, Science 353, 1014 (2016).
14) M. S. Chen, M. C. White, Science 318, 783 (2007).
15) M. S. Chen, M. C. White, Science 327, 566 (2010).
16) J. B. C. Mack, J. D. Gipson, J. Du Bois, M. S. Sigman, J. Am. Chem. Soc. 139, 9503 (2017).
17) V. Lyaskovskyy, A. I. Olivos Suarez, H. Lu, H. Jiang, X. P. Zhang, B. de Bruin, J. Am. Chem. Soc. 133, 12264 (2011).
18) A. Varela-Alvarez, T. Yang, H. Hennings, K. P. Kornecki, S. N. Macmillan, K. M. Lancaster, J. B. C. Mack, J. Du Bois, J. F. Berry, D. G. Musaev, J. Am. Chem. Soc. 136, 2327 (2016).
19) H. M. L. Davies, J. R. Manning, Nature 451, 417 (2008).
20) N. Jana, C. Kong, C. Jones, T. G. Driver, J. Am. Chem. Soc. 138, 13271 (2016).
21) B. Bagh, D. L. J. Broere, V. Sinha, P. F. Kuijpers, J. P. van Leest, B. de Bruin, S. Demeshko, M A. Siegler, J. I. van der Vlugt, J. Am. Chem. Soc. 139, 5117 (2017).
22) S. Wiese, Y. M. Badiei, R. T. Gephart, S. Mossin, M. S. Varonka, M. M. Melzer, K. Meyer, T. R. Cundari, T. H. Warren, Angew. Chem. Int. Ed. 49, 8850 (2010).
23) E. T. Hennessey, T. A. Betley, Science 340, 591 (2013).
24) E. R. King, E. T. Hennessey, T. A. Betley, J. Am. Chem. Soc. 133, 8293 (2011).
25) D. A. Iovan, T. A. Betley, J. Am. Chem. Soc. 138, 1983 (2016).
26) Materials, methods, and X-ray diffraction details are described herein.
27) R. A. Anderson, K. Faegri Jr., J. C. Green, A. Haaland, M. F. Lappert, W. P. Leung, K. Rypdal, Inorg. Chem. 27, 1782 (1988).
28) M. Dryzhakov, M. Hellal, E. Wolf, F. C. Falk, J. Moran, J. Am. Chem. Soc. 137, 9555 (2015).
29) C. Liu, X. Wang, Z. Li, L. Cui, C. Li, J. Am. Chem. Soc. 137, 9820 (2015).
30) M. J. B. Aguila, Y. M. Badiei, T. H. Warren, J. Am. Chem. Soc. 135, 9399 (2013).

31) E. Vitaku, D. T. Smith, J. T. Njardarson, *J. Med. Chem.* 57, 10257 (2014).
32) D. O'Hagan, *Nat. Prod. Rep.* 17, 435 (2000).
33) A. G. King, J. Meinwald, *Chem. Rev.* 96, 1105 (1996).
34) G. Grynkiewiscz, M. Gadzikowska, *Pharmacol. Rep.* 60, 439 (2008).
35) M. Moriya, *J. Chem. Soc. Trans.* 39, 77 (1881).
36) J. Read, *Chem. Rev.* 7, 1, (1930).
37) A. A. Goldberg, V. R. Richard, P. Kyryakov, S. D. Bourque, A. Beach, M. T. Burstein, A. Glebov, O. Koupaki, T. Boukh-Viner, C. Gregg, M. Juneau, A. M. English, D. Y. Thomas, V. I. Titorenko, *Aging* 2, 393 (2010).
38) J. T. Groves, R. C. Haushalter, M. Nakamura, T. E. Nemo, B. J. Evans, *J. Am. Chem. Soc.* 103, 2884 (1981).
39) M. E. Harvey, D. G. Masaev, J. Du Bois, *J. Am. Chem. Soc.* 133, 17207 (2011).
40) C. Kleinlein, S.-L. Zheng, T. A. Betley, *Inorg. Chem.* 56, 5892 (2017).

EQUIVALENTS AND SCOPE

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (I):

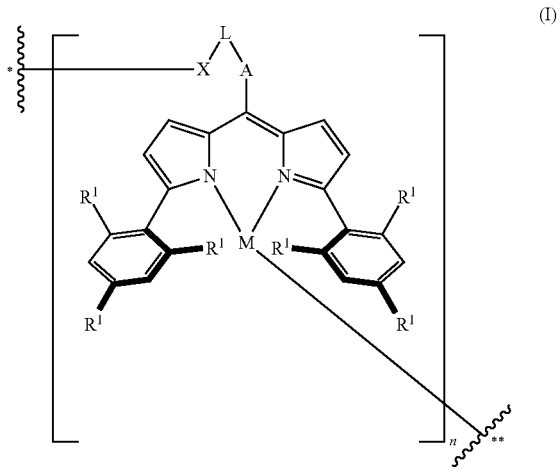

or a salt thereof,
wherein:
   each $R^1$ independently is branched or unbranched, substituted or unsubstituted, cyclic or acyclic aliphatic; branched or unbranched, substituted or unsubstituted, cyclic or acyclic heteroaliphatic; substituted or unsubstituted aryl; or substituted or unsubstituted heteroaryl;
   A is substituted or unsubstituted arylene; or substituted or unsubstituted heteroarylene;
   L is branched or unbranched, substituted or unsubstituted, cyclic or acyclic aliphatic; or branched or unbranched, substituted or unsubstituted, cyclic or acyclic heteroaliphatic;
   X is S, O, or $NR_X$, wherein $R_X$ is hydrogen; nitrogen protecting group; branched or unbranched, substituted or unsubstituted, cyclic or acyclic aliphatic; branched or unbranched, substituted or unsubstituted, cyclic or acyclic heteroaliphatic; substituted or unsubstituted arylene; or substituted or unsubstituted heteroarylene;
   M is a transition metal; and
   n is an integer between 2 and 10, inclusive;
wherein the atom X labeled "*" of one monomer is bonded to the transition metal M labeled "**" of another monomer.

2. The compound of claim 1, or a salt thereof, wherein the compound is of formula:

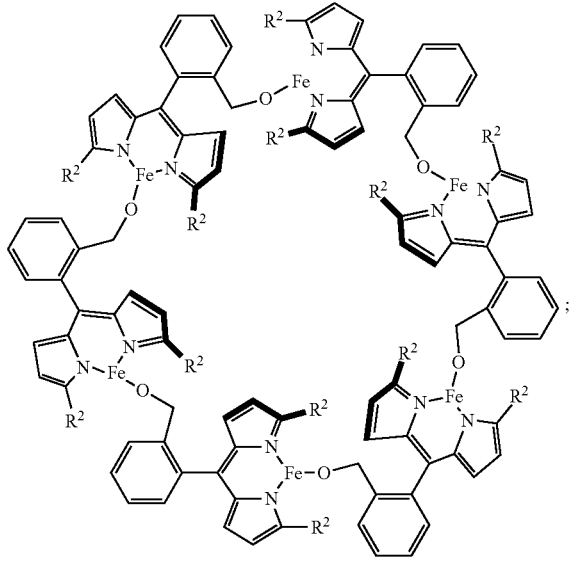

and
each R² is of the formula

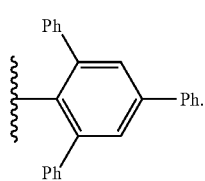 [SMILES: *c1c(-c2ccccc2)cc(-c2ccccc2)cc1-c1ccccc1]

3. The compound of claim 1, or a salt thereof, wherein the compound is of formula:

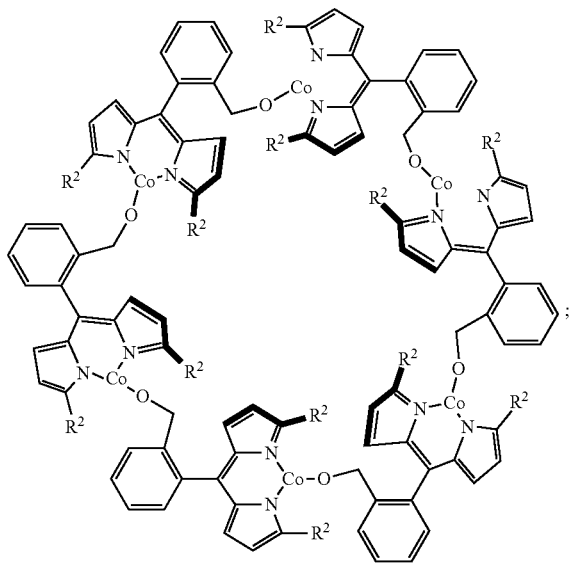

and
each R² is of the formula

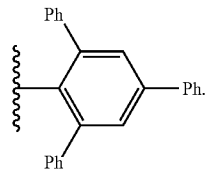 [SMILES: *c1c(-c2ccccc2)cc(-c2ccccc2)cc1-c1ccccc1]

4. The compound of claim 1, or a salt thereof, wherein the compound is of formula:

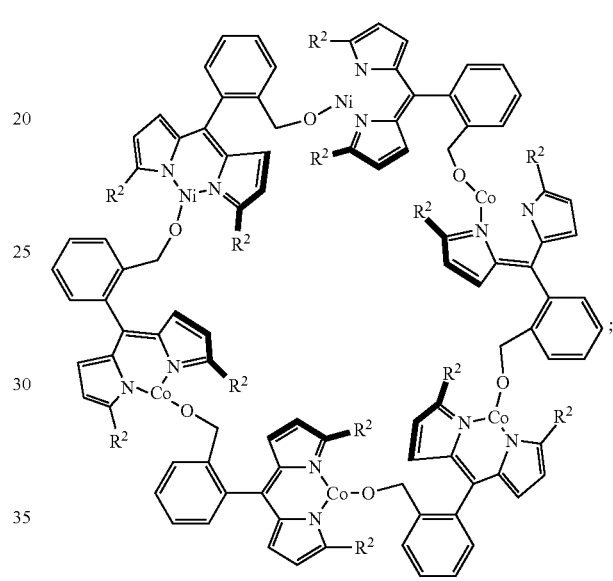

and
each R² is of the formula

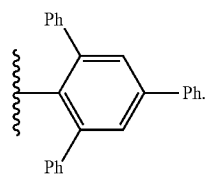 [SMILES: *c1c(-c2ccccc2)cc(-c2ccccc2)cc1-c1ccccc1]

5. A method of preparing a compound of Formula (IV):

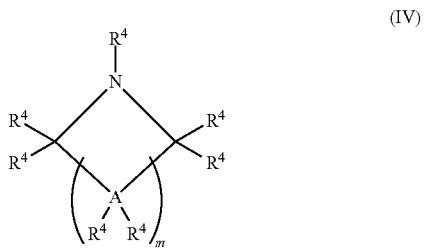

or a salt thereof, comprising:
reacting an azide of Formula (IV-a) with a compound of claim 1, or a salt thereof, to produce a cyclic amine of Formula (IV);

wherein:
an azide of Formula (IV-a) is of formula

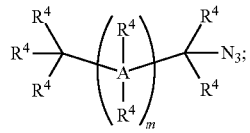
(IV-a)

each $R^4$ independently is hydrogen; branched or unbranched, substituted or unsubstituted, cyclic or acyclic aliphatic; branched or unbranched, substituted or unsubstituted, cyclic or acyclic heteroaliphatic; substituted or unsubstituted aryl; substituted or unsubstituted heteroaryl; two $R^4$ bonded to the same atom are taken together to form an oxo group or a cyclic aliphatic or cyclic heteroaliphatic moiety; two $R^4$ bonded to different atoms are taken together to form a cyclic aliphatic, cyclic heteroaliphatic, arylene, or heteroarylene moiety; two $R^4$ bonded to two adjacent atoms are replaced with a π bond between the two adjacent atoms; or absent;

m is an integer between 2 and 8, inclusive;

each A independently is C, S, O, or N.

6. The method of claim 5, wherein the azide of Formula (IV-a) is selected from the group consisting of:

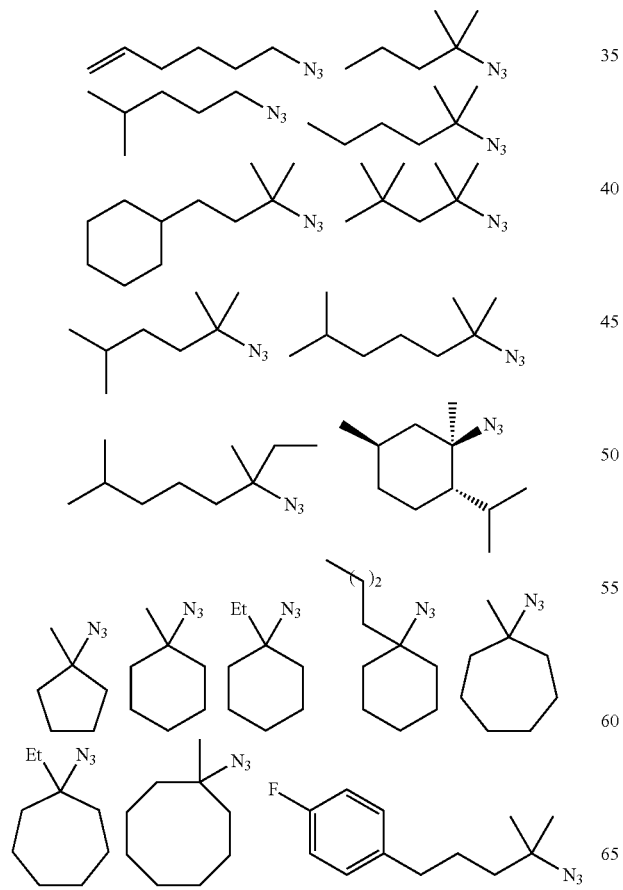

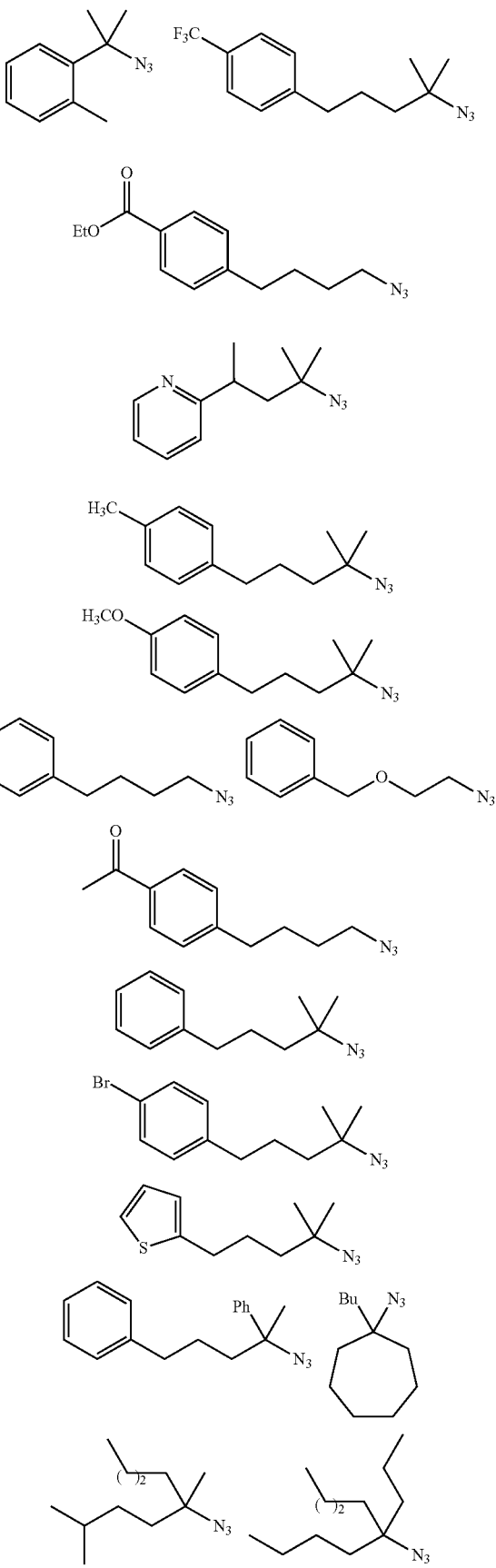

-continued

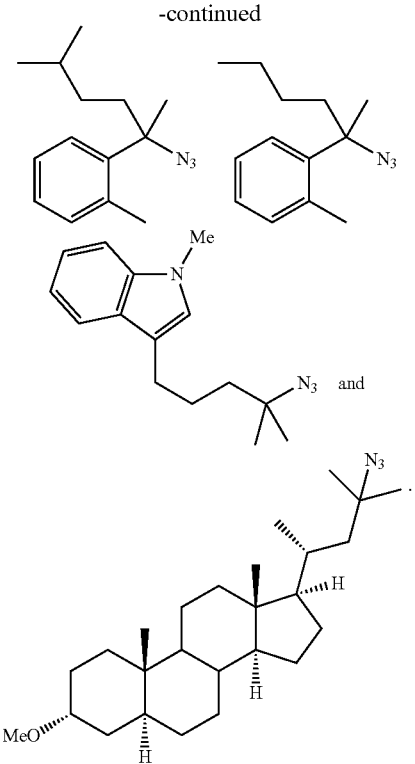

7. A method of preparing a compound of claim 1, or a salt thereof, comprising:
reacting a compound of Formula (I-a):

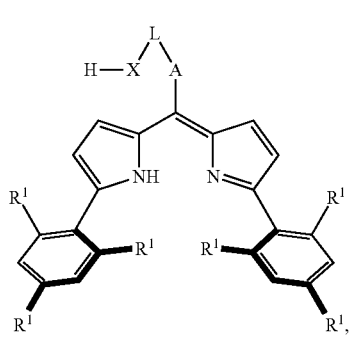
(I-a)

or a salt thereof, with an organometallic iron compound to produce a compound of claim 1, or a salt thereof, wherein:
each $R^1$ independently is branched or unbranched, substituted or unsubstituted, cyclic or acyclic aliphatic; branched or unbranched, substituted or unsubstituted, cyclic or acyclic heteroaliphatic; substituted or unsubstituted aryl; or substituted or unsubstituted heteroaryl;
A is substituted or unsubstituted arylene; or substituted or unsubstituted heteroarylene;
L is branched or unbranched, substituted or unsubstituted, cyclic or acyclic aliphatic; or branched or unbranched, substituted or unsubstituted, cyclic or acyclic heteroaliphatic; and
X is S, O, or $NR_X$, wherein $R_X$ is hydrogen; nitrogen protecting group; branched or unbranched, substituted or unsubstituted, cyclic or acyclic aliphatic; branched or unbranched, substituted or unsubstituted, cyclic or acyclic heteroaliphatic; substituted or unsubstituted arylene; or substituted or unsubstituted heteroarylene.

8. A kit comprising:
a) a compound of claim 1, or a salt thereof, in a first container;
b) an azide of Formula (IV-a) in a second container,

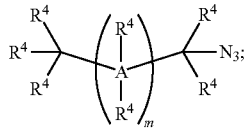
(IV-a)

wherein:
each $R^4$ independently is hydrogen; branched or unbranched, substituted or unsubstituted, cyclic or acyclic aliphatic; branched or unbranched, substituted or unsubstituted, cyclic or acyclic heteroaliphatic; substituted or unsubstituted aryl; substituted or unsubstituted heteroaryl; two $R^4$ bonded to the same atom are taken together to form an oxo group or a cyclic aliphatic or cyclic heteroaliphatic moiety; two $R^4$ bonded to different atoms are taken together to form a cyclic aliphatic, cyclic heteroaliphatic, arylene, or heteroarylene moiety; two $R^4$ bonded to two adjacent atoms are replaced with a π bond between the two atom; or absent;
m is an integer between 2 and 8, inclusive;
each A independently is C, S, O, or N;
c) optionally, one or more solvents; and
d) optionally, instructions for use.

9. A compound of Formula (I-a):

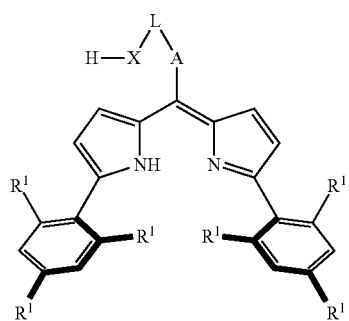
(I-a)

or a salt thereof,
wherein:
each $R^1$ independently is branched or unbranched, substituted or unsubstituted, cyclic or acyclic aliphatic; branched or unbranched, substituted or unsubstituted, cyclic or acyclic heteroaliphatic; substituted or unsubstituted aryl; or substituted or unsubstituted heteroaryl;
A is substituted or unsubstituted arylene; or substituted or unsubstituted heteroarylene;
L is branched or unbranched, substituted or unsubstituted, cyclic or acyclic aliphatic; or branched or unbranched, substituted or unsubstituted, cyclic or acyclic heteroaliphatic; and
X is S, O, or $NR_X$, wherein $R_X$ is hydrogen; nitrogen protecting group; branched or unbranched, substituted or unsubstituted, cyclic or acyclic aliphatic;

branched or unbranched, substituted or unsubstituted, cyclic or acyclic heteroaliphatic; substituted or unsubstituted arylene; or substituted or unsubstituted heteroarylene.

10. The compound of claim 9, or a salt thereof, wherein the compound is of the formula:

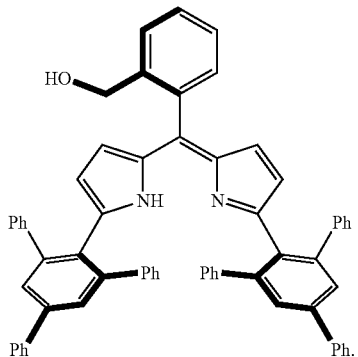

11. A kit comprising:
a) a compound of claim 9, or a salt thereof, in a first container;
b) an organometallic compound in a second container;
c) optionally, one or more solvents; and
d) optionally, instructions for use.

12. A compound of Formula (II):

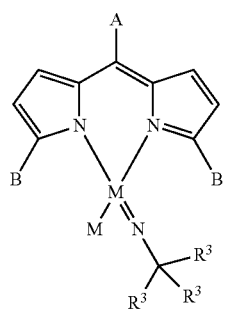

(II)

or a salt thereof,
wherein:
each $R^3$ independently is hydrogen; branched or unbranched, substituted or unsubstituted, cyclic or acyclic aliphatic; branched or unbranched, substituted or unsubstituted, cyclic or acyclic heteroaliphatic; substituted or unsubstituted aryl; substituted or unsubstituted heteroaryl; —$SR_X$ or —$OR_X$, wherein $R_X$ is hydrogen; oxygen protecting group; sulfur protecting group; branched or unbranched, substituted or unsubstituted, cyclic or acyclic aliphatic; branched or unbranched, substituted or unsubstituted, cyclic or acyclic heteroaliphatic; substituted or unsubstituted aryl; or substituted or unsubstituted heteroaryl; or —$N(R_X)_2$, wherein each $R_X$ independently is hydrogen; nitrogen protecting group; branched or unbranched, substituted or unsubstituted, cyclic or acyclic aliphatic; branched or unbranched, substituted or unsubstituted, cyclic or acyclic heteroaliphatic; substituted or unsubstituted aryl; or substituted or unsubstituted heteroaryl;

A is substituted or unsubstituted aryl; or substituted or unsubstituted heteroaryl;

each B independently is branched or unbranched, substituted or unsubstituted, cyclic or acyclic aliphatic; branched or unbranched, substituted or unsubstituted, cyclic or acyclic heteroaliphatic; substituted or unsubstituted aryl; or substituted or unsubstituted heteroaryl;

$X^1$ is a substituted or unsubstituted, cyclic or acyclic heteroaliphatic; or substituted or unsubstituted heteroarylene; and M is a transition metal.

13. The compound of claim 12, or a salt thereof, wherein the compound is selected from the group consisting of:

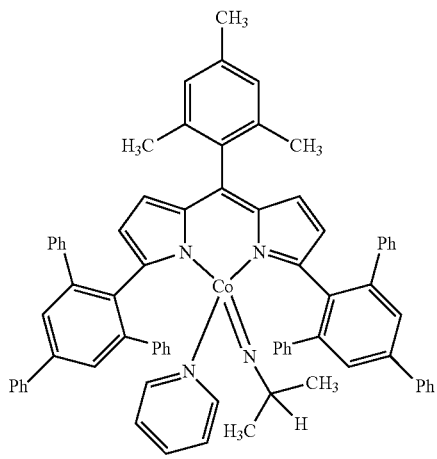

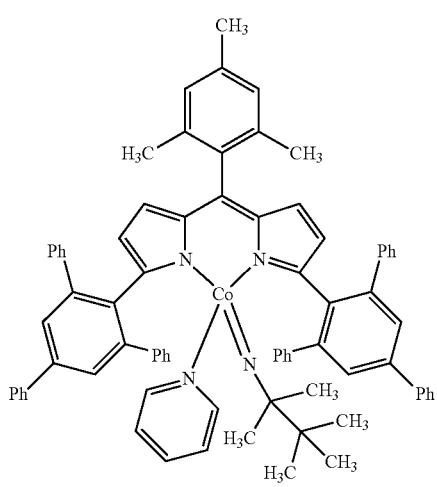

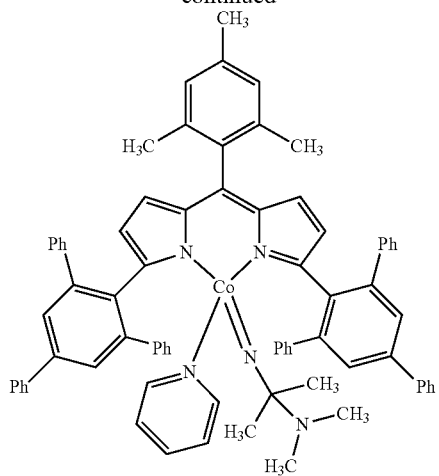
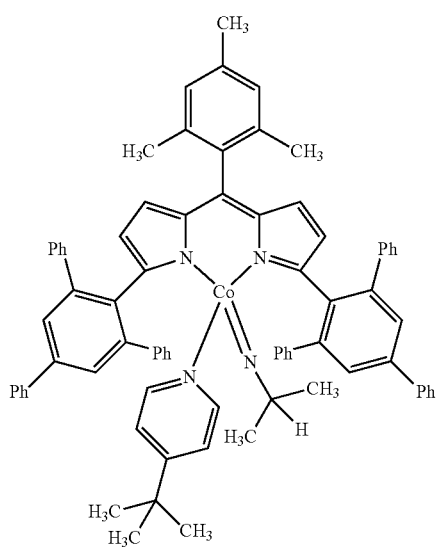
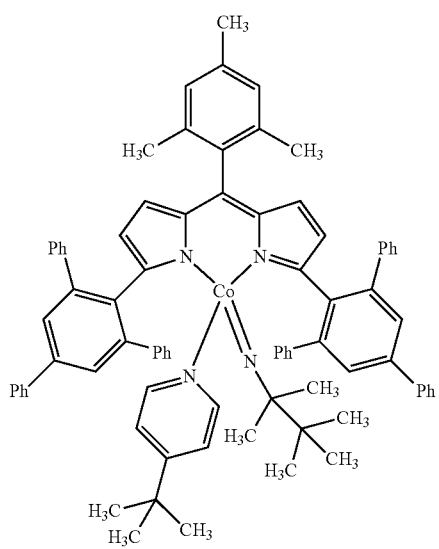
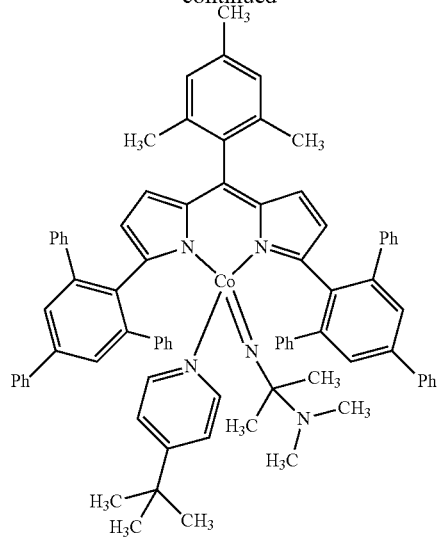
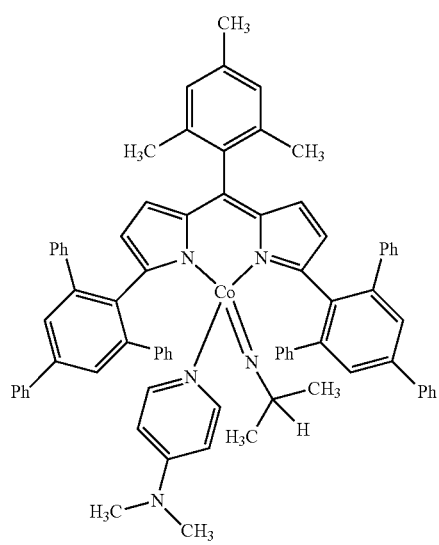
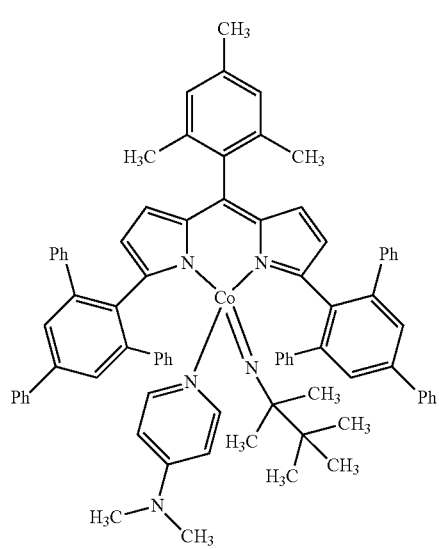

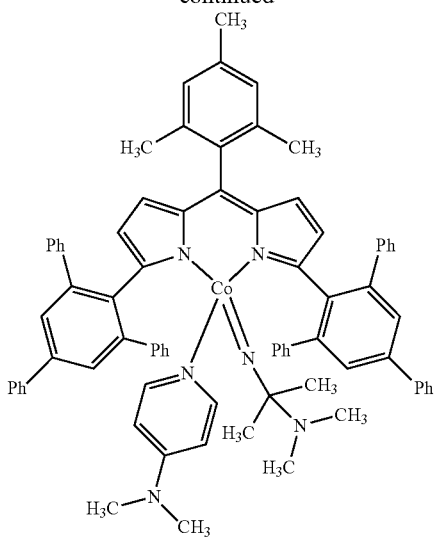

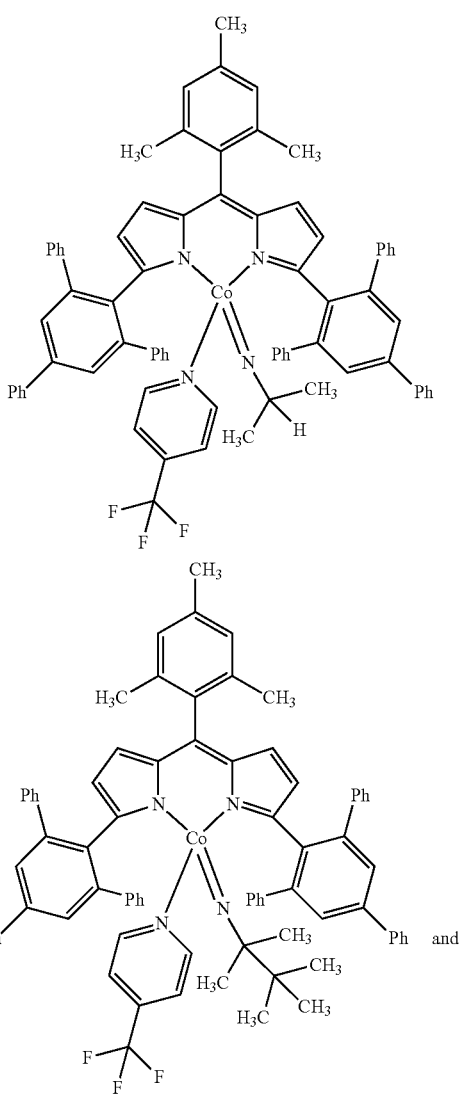

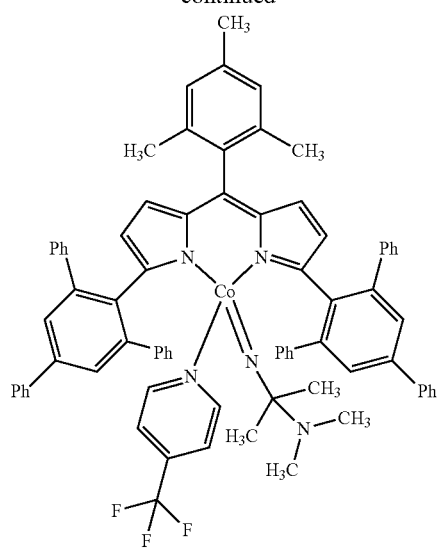

or a salt thereof.

14. A method of preparing a compound of Formula (IV):

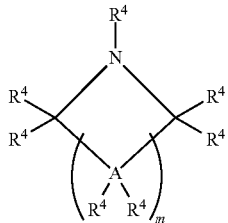

(IV)

or a salt thereof, comprising:
reacting an azide of Formula (IV-a) with a compound of claim 12, or a salt thereof, to produce a cyclic amine of Formula (IV);
wherein:
an azide of Formula (IV-a) is of formula

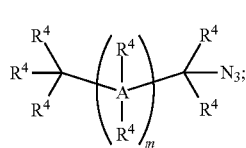

(IV-a)

each $R^4$ independently is hydrogen; branched or unbranched, substituted or unsubstituted, cyclic or acyclic aliphatic; branched or unbranched, substituted or unsubstituted, cyclic or acyclic heteroaliphatic; substituted or unsubstituted aryl; substituted or unsubstituted heteroaryl; two $R^4$ bonded to the same atom are taken together to form an oxo group or a cyclic aliphatic or cyclic heteroaliphatic moiety; two $R^4$ bonded to different atoms are taken together to form a cyclic aliphatic, cyclic heteroaliphatic, arylene, or heteroarylene moiety; two $R^4$ bonded to two adjacent atoms are replaced with a π bond between the two adjacent atoms; or absent;

m is an integer between 2 and 8, inclusive;

each A independently is C, S, O, or N.

15. A kit comprising:
a) a compound of claim 12, or a salt thereof, in a first container;
b) an azide of Formula (IV-a) in a second container,

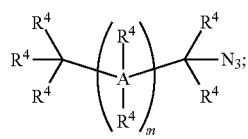

(IV-a)

wherein:
each $R^4$ independently is hydrogen; branched or unbranched, substituted or unsubstituted, cyclic or acyclic aliphatic; branched or unbranched, substituted or unsubstituted, cyclic or acyclic heteroaliphatic; substituted or unsubstituted aryl; substituted or unsubstituted heteroaryl; two $R^4$ bonded to the same atom are taken together to form an oxo group or a cyclic aliphatic or cyclic heteroaliphatic moiety; two $R^4$ bonded to different atoms are taken together to form a cyclic aliphatic, cyclic heteroaliphatic, arylene, or heteroarylene moiety; two $R^4$ bonded to two adjacent atoms are replaced with a π bond between the two atom; or absent;

m is an integer between 2 and 8, inclusive;

each A independently is C, S, O, or N;

c) optionally, one or more solvents; and
d) optionally, instructions for use.

16. A compound of Formula (III):

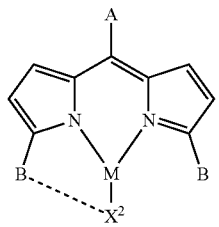

(III)

or a salt thereof,
wherein:
A is substituted or unsubstituted aryl; or substituted or unsubstituted heteroaryl;
each B independently is branched or unbranched, substituted or unsubstituted, cyclic or acyclic aliphatic; branched or unbranched, substituted or unsubstituted, cyclic or acyclic heteroaliphatic; substituted or unsubstituted aryl; or substituted or unsubstituted heteroaryl;
$X^2$ is branched or unbranched, substituted or unsubstituted, cyclic or acyclic heteroaliphatic; substituted or unsubstituted aryl; or substituted or unsubstituted heteroaryl;
... is a bond or absent; and
M is a transition metal.

17. The compound of claim 16, or a salt thereof, wherein the compound is of the formula:

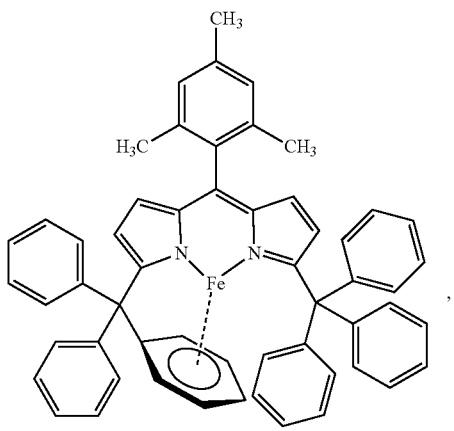

,

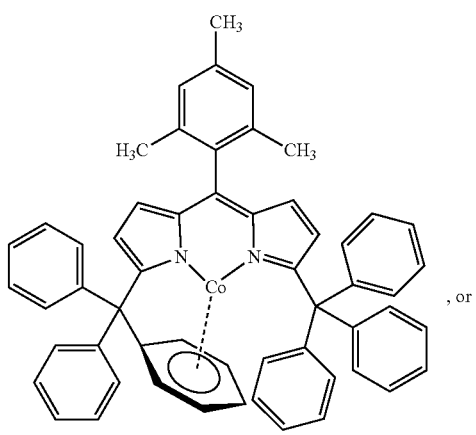

, or

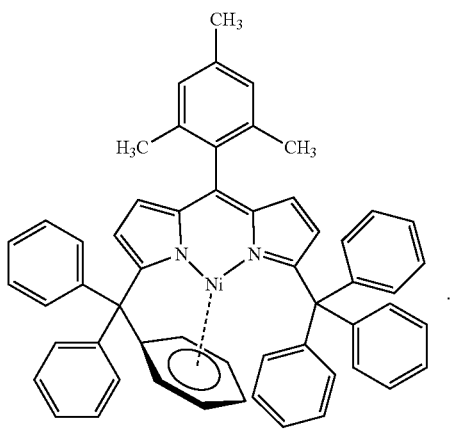

.

18. The compound of claim 16, wherein the compound is of the formula:

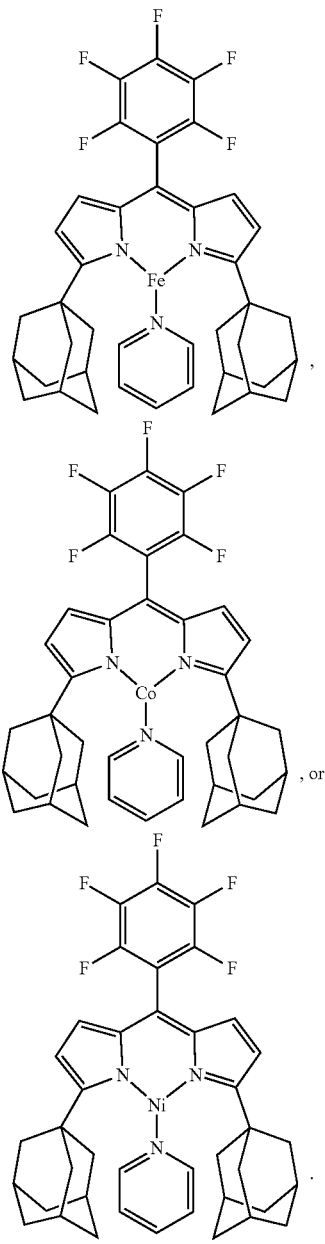

, or

19. A method of preparing a compound of Formula (IV):

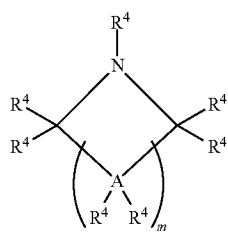

(IV)

or a salt thereof, comprising:
reacting an azide of Formula (IV-a) with a compound of claim 16, or a salt thereof, to produce a cyclic amine of Formula (IV);
wherein:
an azide of Formula (IV-a) is of formula

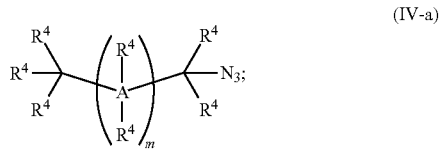

(IV-a)

each $R^4$ independently is hydrogen; branched or unbranched, substituted or unsubstituted, cyclic or acyclic aliphatic; branched or unbranched, substituted or unsubstituted, cyclic or acyclic heteroaliphatic; substituted or unsubstituted aryl; substituted or unsubstituted heteroaryl; two $R^4$ bonded to the same atom are taken together to form an oxo group or a cyclic aliphatic or cyclic heteroaliphatic moiety; two $R^4$ bonded to different atoms are taken together to form a cyclic aliphatic, cyclic heteroaliphatic, arylene, or heteroarylene moiety; two $R^4$ bonded to two adjacent atoms are replaced with a π bond between the two adjacent atoms; or absent;
m is an integer between 2 and 8, inclusive;
each A independently is C, S, O, or N.

20. A kit comprising:
a) a compound of claim 16, or a salt thereof, in a first container;
b) an azide of Formula (IV-a) in a second container,

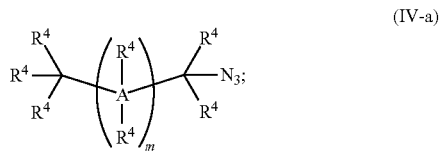

(IV-a)

wherein:
each $R^4$ independently is hydrogen; branched or unbranched, substituted or unsubstituted, cyclic or acyclic aliphatic; branched or unbranched, substituted or unsubstituted, cyclic or acyclic heteroaliphatic; substituted or unsubstituted aryl; substituted or unsubstituted heteroaryl; two $R^4$ bonded to the same atom are taken together to form an oxo group or a cyclic aliphatic or cyclic heteroaliphatic moiety; two $R^4$ bonded to different atoms are taken together to form a cyclic aliphatic, cyclic heteroaliphatic, arylene, or heteroarylene moiety; two $R^4$ bonded to two adjacent atoms are replaced with a π bond between the two atom; or absent;
m is an integer between 2 and 8, inclusive;
each A independently is C, S, O, or N;
c) optionally, one or more solvents; and
d) optionally, instructions for use.

* * * * *

UNITED STATES PATENT AND TRADEMARK OFFICE
CERTIFICATE OF CORRECTION

PATENT NO. : 11,918,984 B2
APPLICATION NO. : 17/276855
DATED : March 5, 2024
INVENTOR(S) : Theodore Alexander Betley et al.

It is certified that error appears in the above-identified patent and that said Letters Patent is hereby corrected as shown below:

In the Specification

At Column 1, Lines 15-17, please change the sentence:
"This invention was made with government support under GM-115815 awarded by the National Institutes of Health. The government has certain rights in the invention."
To:
--This invention was made with government support under GM115815 awarded by National Institutes of Health (NIH). The government has certain rights in this invention.--

In the Claims

In Claim 4, at Column 102, Lines 17-38, the formula:

Signed and Sealed this
Twenty-fifth Day of June, 2024

Katherine Kelly Vidal
*Director of the United States Patent and Trademark Office*

CERTIFICATE OF CORRECTION (continued)
U.S. Pat. No. 11,918,984 B2

In Claim 12, at Column 107, Lines 34-45, the formula:

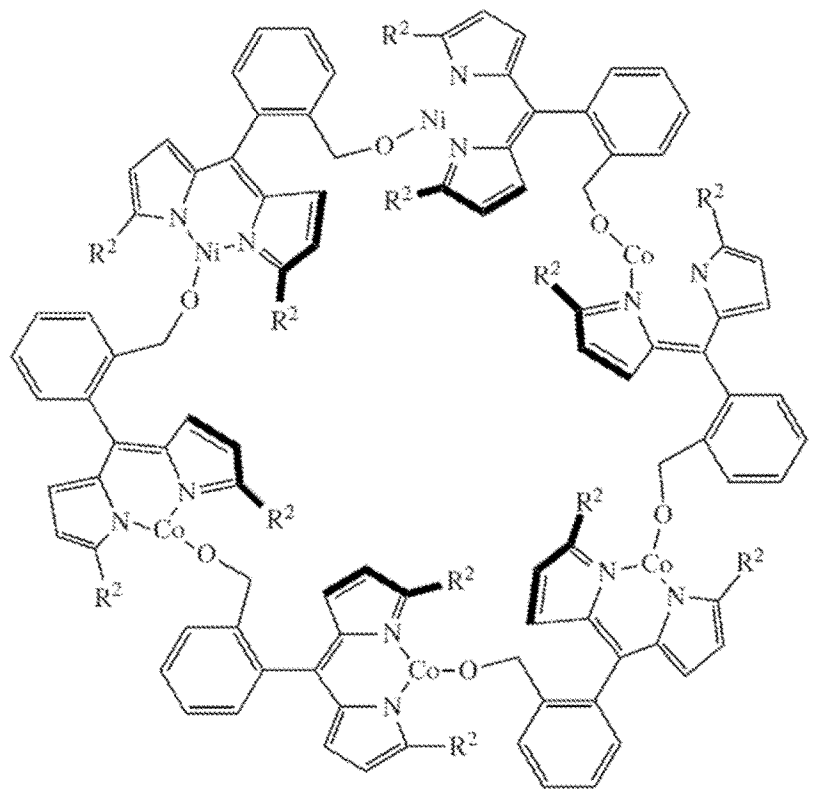

Should be replaced with the formula:

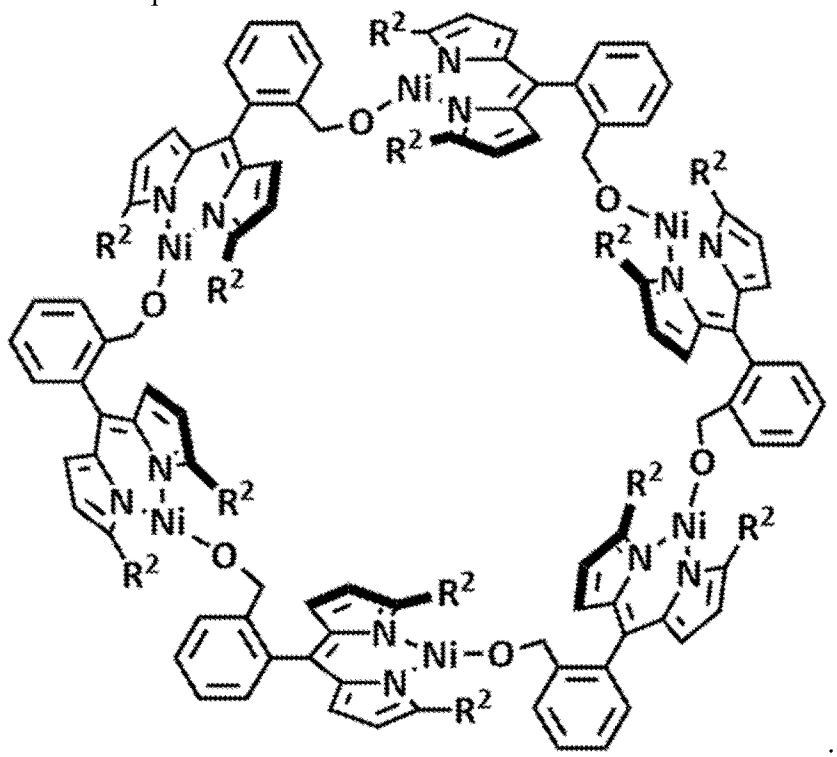

CERTIFICATE OF CORRECTION (continued)
U.S. Pat. No. 11,918,984 B2

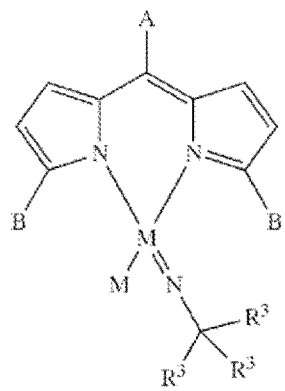

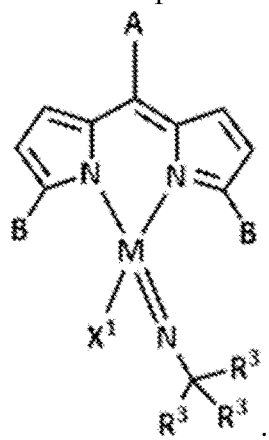

Should be replaced with the formula: